US012344643B2

(12) United States Patent
LaBelle et al.

(10) Patent No.: US 12,344,643 B2
(45) Date of Patent: Jul. 1, 2025

(54) COMPOSITIONS AND METHODS FOR INHIBITION OF FOXP3

(71) Applicants: The University of Chicago, Chicago, IL (US); Dana-Farber Cancer Institute, Inc., Boston, MA (US)

(72) Inventors: James LaBelle, Chicago, IL (US); Rachel Eclov, Chicago, IL (US); Gregory Bird, Boston, MA (US); Loren D. Walensky, Boston, MA (US)

(73) Assignees: The University of Chicago, Chicago, IL (US); Dana-Farber Cancer Institute, Inc., Boston, MA (US)

( * ) Notice: Subject to any disclaimer, the term of this patent is extended or adjusted under 35 U.S.C. 154(b) by 287 days.

(21) Appl. No.: 16/464,590

(22) PCT Filed: Dec. 7, 2017

(86) PCT No.: PCT/US2017/065147
§ 371 (c)(1),
(2) Date: May 28, 2019

(87) PCT Pub. No.: WO2018/106937
PCT Pub. Date: Jun. 14, 2018

(65) Prior Publication Data
US 2021/0094990 A1  Apr. 1, 2021

Related U.S. Application Data

(60) Provisional application No. 62/431,147, filed on Dec. 7, 2016.

(51) Int. Cl.
*C07K 14/47* (2006.01)
*A61K 38/00* (2006.01)
*C07K 1/107* (2006.01)
*C07K 14/73* (2006.01)

(52) U.S. Cl.
CPC ........ *C07K 14/4713* (2013.01); *C07K 1/1077* (2013.01); *C07K 14/70514* (2013.01); *A61K 38/00* (2013.01)

(58) Field of Classification Search
None
See application file for complete search history.

(56) References Cited

U.S. PATENT DOCUMENTS

| | | |
|---|---|---|
| 5,446,090 A | 8/1995 | Harris |
| 6,348,558 B1 | 2/2002 | Harris et al. |
| 7,723,468 B2 | 5/2010 | Daffre et al. |
| 8,889,632 B2 | 11/2014 | Bernal et al. |
| 2005/0250680 A1 | 11/2005 | Walensky et al. |
| 2010/0286057 A1 | 11/2010 | Walensky et al. |
| 2012/0141527 A1 | 6/2012 | Walensky et al. |
| 2012/0164066 A1 | 6/2012 | Greene et al. |
| 2012/0172285 A1 | 7/2012 | Walensky et al. |
| 2014/0370042 A1 | 12/2014 | Walensky et al. |

FOREIGN PATENT DOCUMENTS

| | | |
|---|---|---|
| WO | WO 93/06868 | 4/1993 |
| WO | WO 94/08629 | 4/1994 |
| WO | WO 94/09056 | 4/1994 |
| WO | WO 96/26754 | 9/1996 |
| WO | WO 99/14259 | 3/1999 |
| WO | WO 99/34833 | 7/1999 |
| WO | WO 2008/121767 | 10/2008 |
| WO | WO 2009/108261 | 9/2009 |
| WO | WO 2010/060112 | 5/2010 |
| WO | WO 2010/068684 | 6/2010 |
| WO | WO 2010/148335 | 12/2010 |

OTHER PUBLICATIONS

Song et al. "Structural and Biological Features of FOXP3 Dimerization Relevant to Regulatory T Cell Function" Cell Reports 1:665-675. (Year: 2012).*
Walensky L and Bird G "Hydrocarbon-Stapled Peptides: Principles, Practice, and Progress" J. Med. Chem. 57:6275-6288. (Year: 2014).*
Atkins et al., High-dose recombinant interleukin 2 therapy for patients with metastatic melanoma: analysis of 270 patients treated between 1985 and 1993. J Clin Oncol. Jul. 1999;17(7):2105-16.
Balandina et al., Functional defect of regulatory CD4(+)CD25+ T cells in the thymus of patients with autoimmune myasthenia gravis. Blood. Jan. 15, 2005;105(2):735-41.
Bandukwala et al., Structure of a domain-swapped FOXP3 dimer on DNA and its function in regulatory T cells. Immunity. Apr. 22, 2011;34(4):479-91.
Bates et al., Quantification of regulatory T cells enables the identification of high-risk breast cancer patients and those at risk of late relapse. J Clin Oncol. Dec. 1, 2006;24(34):5373-80.
Beeley. Peptidomimetics and small-molecule drug design: towards improved bioavailability and in vivo stability. Trends Biotechnol. Jun. 1994;12(6):213-6.
Bennett et al., The immune dysregulation, polyendocrinopathy, enteropathy, X-linked syndrome (IPEX) is caused by mutations of FOXP3. Nat Genet. Jan. 2001;27(1):20-1.
Bird et al., Chemical synthesis of hydrocarbon-stapled peptides for protein interaction research and therapeutic targeting. Curr Protoc Chem Biol. Sep. 1, 2011;3(3):99-117.
Bird et al., Biophysical determinants for cellular uptake of hydrocarbon-stapled peptide helices. Nat Chem Biol. Oct. 2016;12(10):845-52.
Bird et al., Distinct BimBH3 (BimSAHB) stapled peptides for structural and cellular studies. ACS Chem Biol. Mar. 21, 2014;9(3):831-7.

(Continued)

*Primary Examiner* — Sudhakar Katakam
*Assistant Examiner* — Zachary J Miknis
(74) *Attorney, Agent, or Firm* — David W. Staple; Casimir Jones, S.C.

(57) ABSTRACT

Provided herein are peptide-based therapeutics that target FOXP3 and methods of use thereof to decrease the immunosuppressive effects of Tregs and inhibit immune dysregulation, while sparring inhibition of activated cytotoxic T cells, for example, in the context of anti-tumor immune responses, autoimmunity, inflammatory conditions, etc.

13 Claims, 25 Drawing Sheets
Specification includes a Sequence Listing.

(56) References Cited

OTHER PUBLICATIONS

Bird et al., Hydrocarbon double-stapling remedies the proteolytic instability of a lengthy peptide therapeutic. Proc Natl Acad Sci U S A. Aug. 10, 2010;107(32):14093-8.
Bird et al., Mucosal delivery of a double-stapled RSV peptide prevents nasopulmonary infection. J Clin Invest. May 2014;124(5):2113-24.
Bird et al., Synthesis and biophysical characterization of stabilized alpha-helices of BCL-2 domains. Methods Enzymol. 2008;446:369-86.
Blackwell et al., Highly Efficient Synthesis of Covalently Cross-Linked Peptide Helices by Ring-Closing Metathesis. Angew Chem Int Ed Engl. Dec. 17, 1998;37(23):3281-3284.
Blackwell et al., Ring-closing metathesis of olefinic peptides: design, synthesis, and structural characterization of macrocyclic helical peptides. J Org Chem. Aug. 10, 2001;66(16):5291-302.
Bottger et al., Identification of novel mdm2 binding peptides by phage display. Oncogene. Nov. 21, 1996;13(10):2141-7.
Bottger et al., Molecular characterization of the hdm2-p53 interaction. J Mol Biol. Jun. 27, 1997;269(5):744-56.
Brinckerhoff et al., Terminal modifications inhibit proteolytic degradation of an immunogenic MART-1(27-35) peptide: implications for peptide vaccines. Int J Cancer. Oct. 29, 1999;83(3):326-34.
Brunel et al., Synthesis of constrained helical peptides by thioether ligation: application to analogs of gp41. Chem Commun (Camb). May 28, 2005;(20):2552-4.
Colombo et al., Regulatory-T-cell inhibition versus depletion: the right choice in cancer immunotherapy. Nat Rev Cancer. Nov. 2007;7(11):880-7.
Curiel et al., Specific recruitment of regulatory T cells in ovarian carcinoma fosters immune privilege and predicts reduced survival. Nat Med. Sep. 2004;10(9):942-9.
Dannull et al., Enhancement of vaccine-mediated antitumor immunity in cancer patients after depletion of regulatory T cells. J Clin Invest. Dec. 2005;115(12):3623-33.
Dasgupta et al., N-terminal acylation of somatostatin analog with long chain fatty acids enhances its stability and anti-proliferative activity in human breast adenocarcinoma cells. Biol Pharm Bull. Jan. 2002;25(1):29-36.
Doronina et al., Development of potent monoclonal antibody auristatin conjugates for cancer therapy. Nat Biotechnol. Jul. 2003;21(7):778-84.
Duijkers et al., Single dose pharmacokinetics and effects on follicular growth and serum hormones of a long-acting recombinant FSH preparation (FSH-CTP) in healthy pituitary-suppressed females. Hum Reprod. Aug. 2002;17(8):1987-93.
Edwards et al., Cellular Uptake and Ultrastructural Localization Underlie the Pro-apoptotic Activity of a Hydrocarbon-stapled BIM BH3 Peptide. ACS Chem Biol. Sep. 18, 2015;10(9):2149-57.
Ellman et al., Biosynthetic method for introducing unnatural amino acids site-specifically into proteins. Methods Enzymol. 1991;202:301-36.
Fieser and M. Fieser, Fieser and Fieser's Reagents for Organic Synthesis, John Wiley and Sons. 1994. TOC only. 54 pages.
Floss et al., Elastin-like polypeptides revolutionize recombinant protein expression and their biomedical application. Trends Biotechnol. Jan. 2010;28(1):37-45.
Fontenot et al., Foxp3 programs the development and function of CD4+CD25+ regulatory T cells. Nat Immunol. Apr. 2003;4(4):330-6.
Fyfe et al., Results of treatment of 255 patients with metastatic renal cell carcinoma who received high-dose recombinant interleukin-2 therapy. J Clin Oncol. Mar. 1995;13(3):688-96.
Galande et al., Potent inhibitors of LXXLL-based protein-protein interactions. Chembiochem. Nov. 2005;6(11):1991-8.
Gentilucci et al., Chemical modifications designed to improve peptide stability: incorporation of non-natural amino acids, pseudo-peptide bonds, and cyclization. Curr Pharm Des. 2010;16(28):3185-203.
Georgiadis et al., Polysialic acids: potential in improving the stability and pharmacokinetics of proteins and other therapeutics. Cell Mol Life Sci. Dec. 2000;57(13-14):1964-9.
Green et al., N-terminal His(7)-modification of glucagon-like peptide-1(7-36) amide generates dipeptidyl peptidase IV-stable analogues with potent antihyperglycaemic activity. J Endocrinol. Mar. 2004;180(3):379-88.
Greene et al., Protective Groups in Organic Synthesis, 3d. Ed., John Wiley and Sons. 1999. TOC only. 3 pages.
Haney et al., Promoting peptide α-helix formation with dynamic covalent oxime side-chain cross-links. Chem Commun (Camb). Oct. 21, 2011;47(39):10915-7.
Harris, Somatostatin and somatostatin analogues: pharmacokinetics and pharmacodynamic effects. Gut. 1994;35(3 Suppl):S1-4.
Hodgson et al., The synthesis of peptides and proteins containing non-natural amino acids. Chem Soc Rev. Sep. 10, 2004;33(7):422-30.
International Search Report and Written Opinion for PCT/US17/65147. Mailed May 1, 2018. 15 pages.
Jackson et al., General approach to the synthesis of short .alpha.— helical peptides. J. Am. Chem. Soc. 1991, 113:9391-9392.
Jacobsen et al., Stapling of a 3(10)-helix with click chemistry. J Org Chem. Mar. 4, 2011;76(5):1228-38.
Judice et al., Inhibition of HIV type 1 infectivity by constrained alpha-helical peptides: implications for the viral fusion mechanism. Proc Natl Acad Sci U S A. Dec. 9, 1997;94(25):13426-30.
Katz et al., Mantle cell lymphoma in cyclin D1 transgenic mice with Bim-deficient B cells. Blood. Feb. 6, 2014;123(6):884-93.
Kawamoto et al., Design of triazole-stapled BCL9 α-helical peptides to target the β-catenin/B-cell CLL/lymphoma 9 (BCL9) protein-protein interaction. J Med Chem. Feb. 9, 2012;55(3):1137-46.
Kieber-Emmons et al., Therapeutic peptides and peptidomimetics. Curr Opin Biotechnol. Aug. 1997;8(4):435-41.
Kim et al., Introduction of all-hydrocarbon i,i+3 staples into alpha-helices via ring-closing olefin metathesis. Org Lett. Jul. 2, 2010;12(13):3046-9.
Koreth et al., Interleukin-2 and regulatory T cells in graft-versus-host disease. N Engl J Med. Dec. 1, 2011;365(22):2055-66.
Krebs et al., Enantioselective synthesis of non-natural aromatic alpha-amino acids. Chemistry. Jan. 23, 2004;10(2):544-53.
Kumita et al., Photo-control of helix content in a short peptide. Proc Natl Acad Sci U S A. Apr. 11, 2000;97(8):3803-8.
Labelle et al., A stapled BIM peptide overcomes apoptotic resistance in hematologic cancers. J Clin Invest. Jun. 2012;122(6):2018-31.
Larock, Comprehensive Organic Transformations, VCH Publishers. 1989. TOC only. 21 pages.
Lau et al., Functionalised staple linkages for modulating the cellular activity of stapled peptides. Chem. Sci., 2014. 5:1804-1809.
Leduc et al., Helix-stabilized cyclic peptides as selective inhibitors of steroid receptor-coactivator interactions. Proc Natl Acad Sci U S A. Sep. 30, 2003;100(20):11273-8.
Li et al., FOXP3 ensembles in T-cell regulation. Immunol Rev. Aug. 2006;212:99-113.
Lozano et al., Inhibition of FOXP3/NFAT Interaction Enhances T Cell Function after TCR Stimulation. J Immunol. Oct. 1, 2015;195(7):3180-9.
Madden et al., Facile synthesis of stapled, structurally reinforced peptide helices via a photoinduced intramolecular 1,3-dipolar cycloaddition reaction. Chem Commun (Camb). Oct. 7, 2009;(37):5588-90.
Madden et al., Synthesis of cell-permeable stapled peptide dual inhibitors of the p53-Mdm2/Mdmx interactions via photoinduced cycloaddition. Bioorg Med Chem Lett. Mar. 1, 2011;21(5):1472-5.
Missirlis et al., Mechanisms of peptide amphiphile internalization by SJSA-1 cells in vitro. Biochemistry. Apr. 21, 2009;48(15):3304-14.
Missirlis et al., The non-peptidic part determines the internalization mechanism and intracellular trafficking of peptide amphiphiles. PLoS One. 2013;8(1):e54611. 10 pages.
Moore. Designing peptide mimetics. Trends Pharmacol Sci. Apr. 1994;15(4):124-9.

(56) References Cited

OTHER PUBLICATIONS

Noren et al., A general method for site-specific incorporation of unnatural amino acids into proteins. Science. Apr. 14, 1989;244(4901):182-8.
Partial Supplementrary European Search for PCT/US2017065147. Mailed Jun. 7, 2020. 14 pages.
PASUT. Polymers for Protein Conjugation. Polymers 2014, 6, 160-178.
Phelan et al., A General Method for Constraining Short Peptides to an α-Helical Conformation. J. Am. Chem. Soc. 1997, 119, 3, 455-460.
Powell et al., Peptide stability in drug development. II. Effect of single amino acid substitution and glycosylation on peptide reactivity in human serum. Pharm Res. Sep. 1993;10(9):1268-73.
Schafmeister et al., An All-Hydrocarbon Cross-Linking System for Enhancing the Helicity and Metabolic Stability of Peptides. J. Am. Chem. Soc. 2000;122(24):5891-5892.
Schellenberger et al., A recombinant polypeptide extends the in vivo half-life of peptides and proteins in a tunable manner. Nat Biotechnol. Dec. 2009;27(12):1186-90.
Schlapschy et al., Fusion of a recombinant antibody fragment with a homo-amino-acid polymer: effects on biophysical properties and prolonged plasma half-life. Protein Eng Des Sel. Jun. 2007;20(6):273-84.
Schlapschy et al., PASylation: a biological alternative to PEGylation for extending the plasma half-life of pharmaceutically active proteins. Protein Eng Des Sel. Aug. 2013;26(8):489-501.
Shepherd et al., Single turn peptide alpha helices with exceptional stability in water. J Am Chem Soc. Mar. 9, 2005;127(9):2974-83.
Sia et al., Short constrained peptides that inhibit HIV-1 entry. Proc Natl Acad Sci U S A. Nov. 12, 2002;99(23):14664-9.
Song et al., Structural and biological features of FOXP3 dimerization relevant to regulatory T cell function. Cell Rep. Jun. 28, 2012;1(6):665-75.
Spokoyny et al., A perfluoroaryl-cysteine S(N)Ar chemistry approach to unprotected peptide stapling. J Am Chem Soc. Apr. 24, 2013;135(16):5946-9.
Supplementary European Search Report for PCT/US2017065147. Mailed Oct. 27, 2020. 11 pages.
Tomalia et al., Starburst Dendrimers: Molecular-Level Control of Size, Shape, Surface Chemistry, Topology, and Flexibility from Atoms to Macroscopic Matter. Angew. Chem. Int. Ed. Engl. 1990. 29:138-175.
Verdine et al., Stapled peptides for intracellular drug targets. Methods Enzymol. 2012;503:3-33.
Vonderheide et al., A Translational Bridge t Cancer Immunotherapy. Immun Res. 2003; 27/2-3:341-355.
Walensky et al., Activation of apoptosis in vivo by a hydrocarbon-stapled BH3 helix. Science. Sep. 3, 2004;305(5689):1466-70.
Walensky et al., Hydrocarbon-stapled peptides: principles, practice, and progress. J Med Chem. Aug. 14, 2014;57(15):6275-88.
Wan et al., Regulatory T-cell functions are subverted and converted owing to attenuated Foxp3 expression. Nature. Feb. 15, 2007;445(7129):766-70.
White et al., Replacing amino acids in translation: expanding chemical diversity with non-natural variants. Methods. Mar. 15, 2013;60(1):70-4.
Williams et al., Asymmetric synthesis of monosubstituted and alpha, alpha-disubstituted alpha-amino acids via diastereoselective glycine enolate alkylations. J. Am. Chem. Soc. 1991, 113, 24, 9276-9286.
Williams et al., Efficient Asymmetric Synthesis Of N-tert-Butoxycarbonyl α-aminoacids USING 4-tert-Butoxycarbonyl-5,6-Diphenylmorpholin-2-One: (R)-(N-tert-Butoxycarbonyl)Allylglycine. Org. Synth. 2003, 80:31.
Wu et al., FOXP3 controls regulatory T cell function through cooperation with NFAT. Cell. Jul. 28, 2006;126(2):375-87.
Zhang et al., Lymphopenia and interleukin-2 therapy alter homeostasis of CD4+CD25+ regulatory T cells. Nat Med. Nov. 2005;11(11):1238-43.
Zheng et al., Genome-wide analysis of Foxp3 target genes in developing and mature regulatory T cells. Nature. Feb. 22, 2007;445(7130):936-40.
Zhou et al., Structural aspects of the FOXP3 regulatory complex as an immunopharmacological target. Int Immunopharmacol. May 2009;9(5):518-20.

* cited by examiner

FIG. 3A
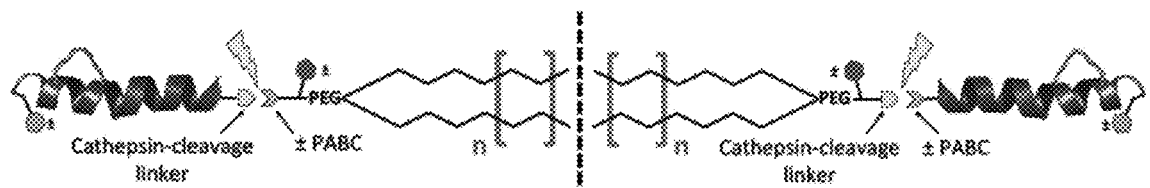
Peptide without cathepsin site | Peptide with cathepsin site + PABC
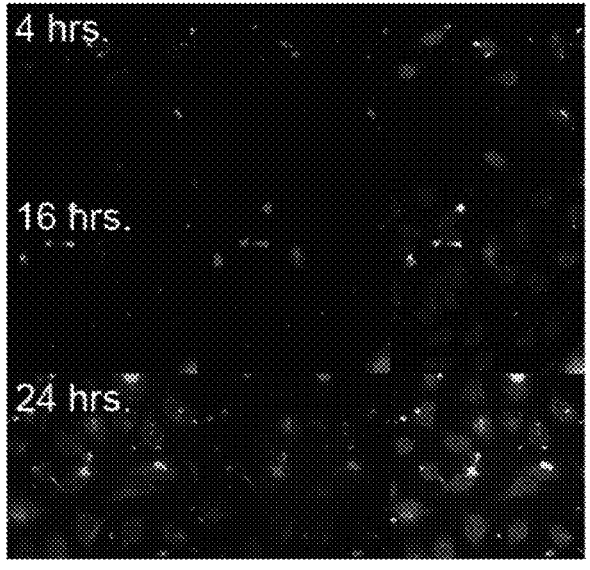 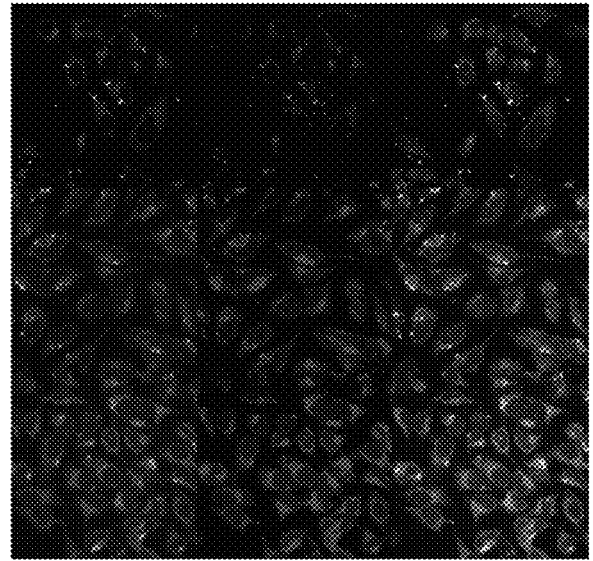
Peptide  Tail  Overlay with Nucleus      Peptide  Tail  Overlay with Nucleus
FIG. 3B FIG. 4A
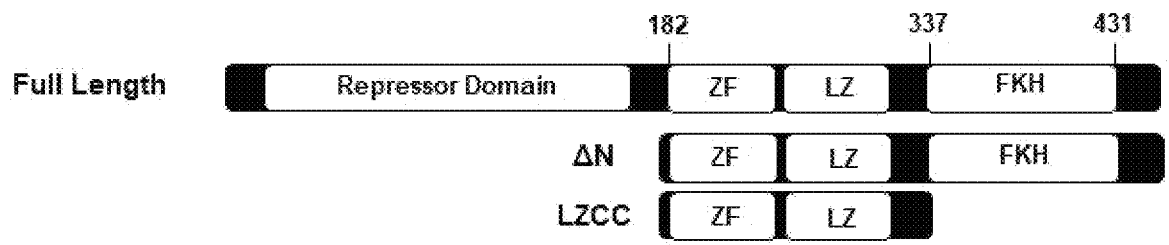
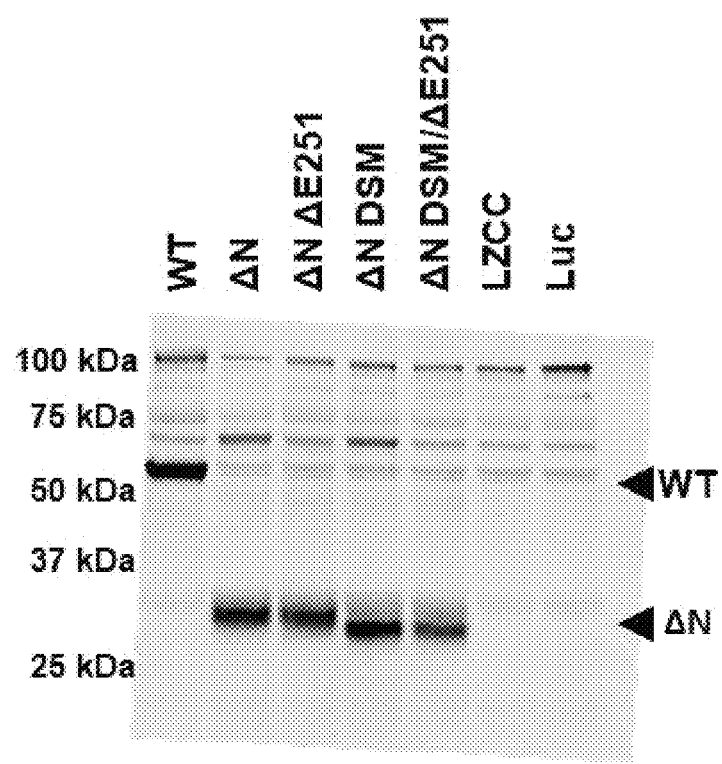
FIG. 4B

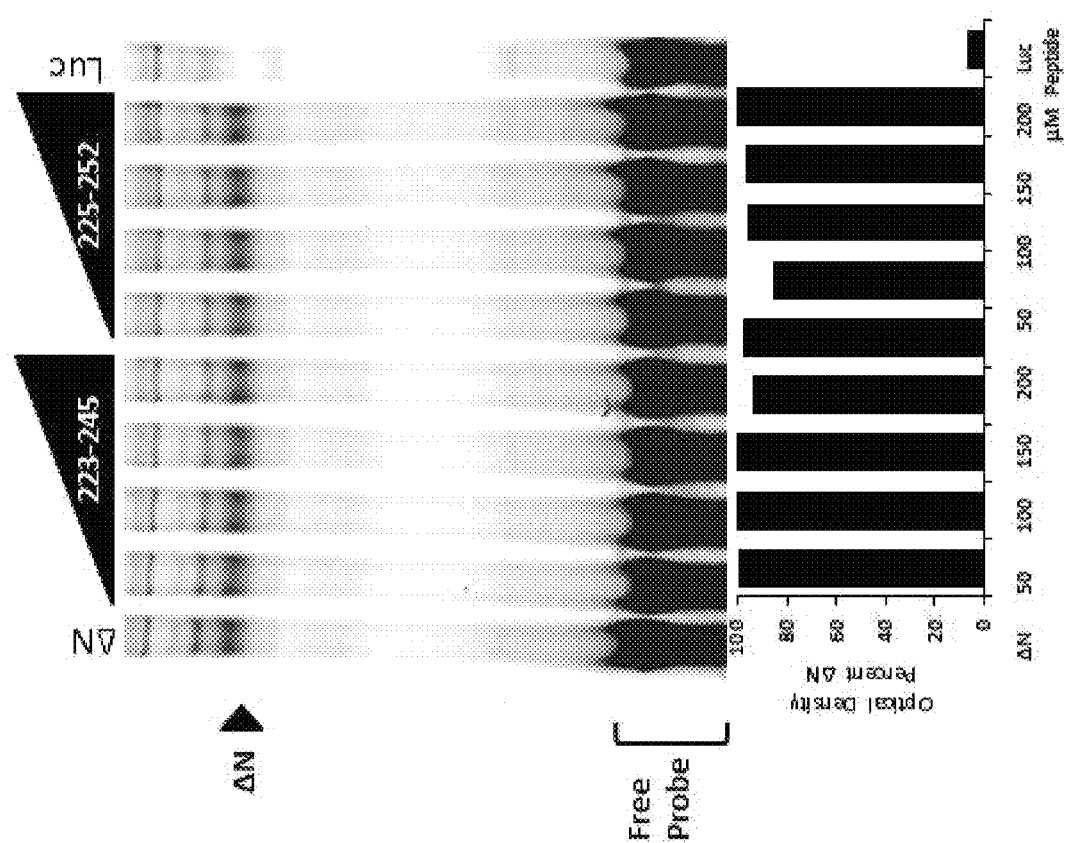

COMPOSITIONS AND METHODS FOR
INHIBITION OF FOXP3

CROSS-REFERENCE TO RELATED APPLICATIONS

The present invention is a § 371 National Entry of PCT/US2017/065147, filed Dec. 7, 2017, which claims priority to U.S. Provisional Patent Application Ser. No. 62/431,147, filed Dec. 7, 2016, each of which is incorporated by reference in its entirety.

SEQUENCE LISTING

The text of the computer readable sequence listing filed herewith, titled "35105-252_SEQUENCE_LISTING", created Feb. 2, 2023, having a file size of 43,379 bytes, is hereby incorporated by reference in its entirety.

FIELD

Provided herein are peptide-based therapeutics that target FOXP3 and methods of use thereof to decrease the immunosuppressive effects of Tregs and inhibit immune dysregulation, while sparring inhibition of activated cytotoxic T cells, for example, in the context of anti-tumor immune responses, autoimmunity, inflammatory conditions, etc.

BACKGROUND

Inhibition of protein:protein interactions (PPIs) has classically centered on using small molecules for inhibition. Small molecules are best at targeting PPIs with defined "hot spot" binding pockets or concentrated binding foci and often fail to target proteins with large, diffuse interfaces (>800 Å2) where binding is the summation of many geographically distinct low-affinity interactions. Thus 90% of human gene products have been historically "undruggable" by small molecules. This is exemplified by there being only one FDA-approved small molecule capable of targeting one of the estimated 650,000 PPIs within the human interactome. Many PPIs, particularly those within transcription factors (TFs), remain challenging to target because of their often large, geographically complex, dynamic, and relatively flat surfaces. Additionally, from a pharmacologic perspective, conventional methods used to target TF activity traditionally fail to achieve high levels of specificity due to reliance on disrupting upstream cell-signaling nodes rather than direct dissociation of critical TF PPIs. This is in large part because of difficulties correlating TF structural data to rational drug design.

Regulatory T cells (Tregs), a population of suppressive $CD4^+$ T cells, are critical for the maintenance of immune tolerance to self-antigens and control of immune responses to foreign agents, including infectious organisms and alloantigens. Recent developments in cancer immunotherapy exploit the ability of T cells to target tumor-associated antigens to clear malignant cells by endogenous or exogenous immune activation. The normal tolerizing function of Tregs is known to prohibit effective anti-tumor T cell-mediated killing, and their presence predicts reduced survival in cancer patients.

Tregs co-express high levels of the IL-2 receptor (CD25) and depend on the transcriptional regulatory protein FOXP3 (Fontenot et al. Nature immunology 4, 330-336 (2003); incorporated by reference in its entirety). Tregs are critical for establishing and maintaining immune homeostasis. FOXP3 is crucial for Treg ontogeny and without it, complete loss of T regulatory function occurs (Bennett, C. L. et al. Nat Genet 27, 20-21 (2001); incorporated by reference in its entirety). The normal tolerizing function of Tregs also prohibits effective anti-tumor T cell-mediated killing and the presence of Tregs in cancer patients predicts reduced survival (Bates, G. J. et al. J Clin Oncol 24, 5373-5380(2006); Curiel, T. J. et al. Nature medicine 10, 942-949 (2004); incorporated by reference in their entireties). Treg depletion through targeting surface expressed CD25 has shown modest improvement in anti-tumor T cell-mediated responses (Dannull, J. et al. J Clin Invest 115, 3623-3633 (2005); incorporated by reference in its entirety). However, there exists a narrow window of opportunity for Treg depletion based on CD25 expression. Activated T cells quickly upregulate CD25 expression and thereby, deletion using anti-CD25 mAbs coincidentally depletes newly activated anti-tumor T cells (Colombo, & Piconese. Nature reviews. Cancer 7, 880-887 (2007); incorporated by reference in its entirety). Alternatively, infusion of high-dose IL-2 has been used in combination with tumor vaccines in the hopes of stimulating tumor immunity; unfortunately, only modest responses have been measured and significant side effects are common (Atkins, et al. J Clin Oncol 17, 2105-2116 (1999); Fyfe et al. J Clin Oncol 13, 688-696 (1995); incorporated by reference in their entireties). Conversely, low-dose IL-2 increases Treg numbers, thereby causing a dominant-negative anti-tumor effect (Koreth et al. The New England journal of medicine 365, 2055-2066 (2011); Zhang, et al. Nature medicine 11, 1238-1243 (2005); incorporated by reference in their entireties).

The field lacks technologies for depleting Tregs in patients without concomitant depletion of activated tumor-specific T cells.

SUMMARY

Provided herein are peptide-based therapeutics that target FOXP3 and methods of use thereof to decrease the immunosuppressive effects of Tregs and inhibit immune dysregulation, while sparring inhibition of activated cytotoxic T cells, for example, in the context of anti-tumor immune responses, autoimmunity, inflammatory conditions, etc.

In some embodiments, provided herein are compositions comprising stapled alpha helical (SAH) peptides of FOXP3's leucine zipper domain. In some embodiments, provided herein are peptide amphiphiles (PAs) displaying SAH peptide of FOXP3's leucine zipper domain. In some embodiments, the SAH peptide of FOXP3's leucine zipper domain is cathepsin cleavable from the peptide amphiphile.

In some embodiments, provided herein are compositions comprising stapled alpha helical (SAH) peptides of FOXP3's NFAT interface domain. In some embodiments, provided herein are peptide amphiphiles (PAs) displaying SAH peptide of FOXP3's NFAT interface domain. In some embodiments, the SAH peptide of FOXP3's NFAT interface domain is cathepsin cleavable from the peptide amphiphile.

In some embodiments, provided herein are methods of inhibiting FOXP3 function, comprising administering the SAH peptides and/or PAs described herein to a cell or subject. In some embodiments, methods are provided for the treatment of cancer and/or autoimmune disease comprising administering a composition described herein to a cell or subject.

In some embodiments, provided herein are SAH peptides that mimic the functionality of the FOXP3 leucine zipper domain or NFAT interface domain. In some embodiments, the SAH peptide inhibits oligomerization (homo- and hetero-oligomerization) of FOXP3.

In some embodiments, the SAH peptide comprises at least 50% (50%, 55%, 60%, 65%, 70%, 75%, 80%, 85%, 90%, 95%, 99%, or ranges therebetween) sequence similarity (e.g., conservative or semi-conservative) but less than 100% sequence identity to SEQ ID NO: 1. In some embodiments, the SAH peptide comprises at least 70% (e.g., 70%, 75%, 80%, 85%, 90%, 95%, 99%, or ranges therebetween) sequence similarity (e.g., conservative or semi-conservative) to one of SEQ ID NOS: 2-32. In some embodiments, the SAH peptide comprises at least 70% (e.g., 70%, 75%, 8-%, 85%, 90%, 95%, 99%, or ranges therebetween) sequence identity to one of SEQ ID NOS: 2-32. In some embodiments, the SAH peptide comprises or consists of a sequence of all or a portion (e.g., at least 8, 10, 12, 14, 16, 18, and/or 20 amino acids) of one of SEQ ID NOS: 2-64 (e.g., SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64). In some embodiments, the peptide comprises 1-5 (e.g., 1, 2, 3, 4, 5, or ranges therebetween) hydrocarbon staples. In some embodiments, the hydrocarbon staple(s) stabilize the alpha helical character or the peptide. In some embodiments, the hydrocarbon staple(s) are selected from i to i+4 and i to i+7 staples. In some embodiments, the SAH peptide comprises one or more non-natural amino acids, modified amino acids, amino acid analogs, and/or peptoid amino acids.

In some embodiments, the SAH peptide comprises at least 50% (50%, 55%, 60%, 65%, 70%, 75%, 80%, 85%, 90%, 95%, 99%, or ranges therebetween) sequence similarity (e.g., conservative or semi-conservative) but less than 100% sequence identity to SEQ ID NO: 66. In some embodiments, the SAH peptide comprises at least 70% (e.g., 70%, 75%, 80%, 85%, 90%, 95%, 99%, or ranges therebetween) sequence similarity (e.g., conservative or semi-conservative) to one of SEQ ID NOS: 2-32. In some embodiments, the peptide comprises 1-5 (e.g., 1, 2, 3, 4, 5, or ranges therebetween) hydrocarbon staples. In some embodiments, the hydrocarbon staple(s) stabilize the alpha helical character or the peptide. In some embodiments, the hydrocarbon staple(s) are selected from i to i+4 and i to i+7 staples. In some embodiments, the SAH peptide comprises one or more non-natural amino acids, modified amino acids, amino acid analogs, and/or peptoid amino acids.

In some embodiments, provided herein are internally cross-linked peptides/polypeptides comprising the amino acid sequence: $E_0F_0G_0$ $A_1B_1C_1D_1E_1F_1G_1$ $A_2B_2C_2D_2E_2F_2G_2$ $A_3B_3C_3D_3E_3F_3G_3$ $A_4B_4C_4D_4E_4F_4G_4$ $A_5B_5C_5D_5E_5F_5G_5A_6B_6C_6$ (SEQ ID NO: 65), wherein: $E_0$ is His, or any amino acid (e.g., any of the 20 naturally occurring amino acids, or analog thereof), $F_0$ is Leu or Ala, or a conservative amino acid substitution, $G_0$ is Leu, or any amino acid, $A_1$ is Asp, or a conservative amino acid substitution, $B_1$ is Glu, or a conservative amino acid substitution, $C_1$ is Lys or Arg, or a conservative amino acid substitution, $D_1$ is Gly or Ser, or a conservative amino acid substitution, $E_1$ is Arg or Lys or Thr, or any amino acid, $F_1$ is Ala, or a conservative amino acid substitution, $G_1$ is Gln, or any amino acid, $A_2$ is Cys, or a conservative amino acid substitution, $B_2$ is Leu or Arg, or any amino acid, $C_2$ is Leu or Val, or a conservative amino acid substitution, $D_2$ is Gln, or a conservative amino acid substitution, $E_2$ is Arg or Met, or any amino acid, $F_2$ is Glu or Gln, or a conservative amino acid substitution, $G_2$ is Met or Val, or any amino acid, $A_3$ is Val, or a conservative amino acid substitution, $B_3$ is Gln, or any amino acid, $C_3$ is Ser or Gln, or a conservative amino acid substitution, $D_3$ is Leu, or a conservative amino acid substitution, $E_3$ is Glu, or a conservative amino acid substitution, $F_3$ is Gln or Leu, or a conservative amino acid substitution, $G_3$ is Gln, or a conservative amino acid substitution, $A_4$ is Leu, or a conservative amino acid substitution, $B_4$ is Val or Glu or Ala or Ser, or any amino acid, $C_4$ is Leu or Lys, or a conservative amino acid substitution, $D_4$ is Glu or Asp, or a conservative amino acid substitution, $E_4$ is Lys or Arg, or a conservative amino acid substitution, $F_4$ is Glu, or any amino acid, $G_4$ is Lys or Arg, or a conservative amino acid substitution, $A_5$ is Leu, or a conservative amino acid substitution, $B_5$ is Ser or Gly or Gln, or any amino acid, $C_5$ is Ala, or any amino acid, $D_5$ is Met, or a conservative amino acid substitution, $E_5$ is Gln or Met, or any amino acid, $F_5$ is Ala or Thr, or any amino acid, $G_5$ is His, or any amino acid, $A_6$ is Leu, or a conservative amino acid substitution, $B_6$ is Ala or His, or any amino acid, $C_6$ is Gly or Val or Met, or any amino acid, wherein the side chains of at least two amino acids separated by two, three, or six amino acids are replaced by an internal cross-link.

In some embodiments, provided herein are internally cross-linked peptides/polypeptides comprising the amino acid sequence $E_0F_0G_0$ $A_1B_1C_1D_1E_1F_1G_1A_2B_2C_2D_2E_2F_2G_2$ $A_3B_3C_3D_3E_3F_3G_3$ $A_4B_4C_4D_4E_4F_4G_4$ $A_5B_5C_5D_5E_5F_5G_5$ $A_6B_6C_6$ (SEQ ID NO:65) wherein: $E_0$ is His, or any amino acid (e.g., any of the 20 naturally occurring amino acids, or analog thereof), $F_0$ is Leu or Ala, or a conservative amino acid substitution, $G_0$ is Leu, or any amino acid, $A_1$ is Asp, or a conservative amino acid substitution, $B_1$ is Glu, or a conservative amino acid substitution, $C_1$ is Lys or Arg, or a conservative amino acid substitution, $D_1$ is Gly or Ser, or a conservative amino acid substitution, $E_1$ is Arg or Lys or Thr, or any amino acid, $F_1$ is Ala, or a conservative amino acid substitution, $G_1$ is Gln, or any amino acid, $A_2$ is Cys, or a conservative amino acid substitution, $B_2$ is Leu or Arg, or any amino acid, $C_2$ is Leu or Val, or a conservative amino acid substitution, $D_2$ is Gln, or a conservative amino acid substitution, $E_2$ is Arg or Met, or any amino acid, $F_2$ is Glu or Gln, or a conservative amino acid substitution, $G_2$ is Met or Val, or any amino acid, $A_3$ is Val, or a conservative amino acid substitution, $B_3$ is Gln, or any amino acid, $C_3$ is Ser or Gln, or a conservative amino acid substitution, $D_3$ is Leu, or a conservative amino acid substitution, $E_3$ is Glu, or a conservative amino acid substitution, $F_3$ is Gln or Leu, or a conservative amino acid substitution, $G_3$ is Gln, or a conservative amino acid substitution, $A_4$ is Leu, or a conservative amino acid substitution, $B_4$ is Val or Glu or Ala or Ser, or any amino acid, $C_4$ is Leu or Lys, or a conservative amino acid substitution, $D_4$ is Glu or Asp, or a conservative amino acid substitution, $E_4$ is Lys or Arg, or a conservative amino acid substitution, $F_4$ is Glu, or any amino acid, $G_4$ is Lys or Arg, or a conservative amino acid substitution, $A_5$ is Leu, or a conservative amino acid substitution, $B_5$ is Ser or Gly or Gln, or any amino acid, $C_5$ is Ala, or any amino acid, $D_5$ is Met, or a conservative amino acid substitution, $E_5$ is Gln or Met, or any amino acid, $F_5$ is Ala or Thr, or any amino acid, $G_5$ is His, or any amino acid, $A_6$ is Leu, or a conservative amino acid substitution, $B_6$ is Ala or His, or any amino acid, $C_6$ is Gly or Val or Met, or any amino acid, wherein: one or more (e.g., 1, 2, 3, 4, 5, 6, 7, 8, 9, 10, 11, 12, 13, 14, 15, 16, 17, 18) of $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, $A_5$, $B_5$, $D_5$, $E_5$, $A_6$, $B_6$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$, $A_5$, $D_5$, $E_5$, $A_6$, are replaced by a conservative amino acid substitution that does not alter the binding face of the peptide; and/or amino acids outside residues corresponding to $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$, $A_5$, $D_5$, $E_5$, $A_6$, are at least 80% (e.g., 80%, 85%, 90%, 95%, 98%, 99%, 99.5%, or 100%) identical to the sequence of SEQ ID NO:1.

In some embodiments, provided herein is a cross-linked peptide with the amino acid sequence is HLL-DEKGRAQCLLQREMVQSLEQQLVLEKEKL-SAMQAHLAG (SEQ ID NO:1). In some embodiments, the amino acid sequence of SEQ ID NO:1 is truncated by 1, 2, 3, 4, 5, 6, 7, 8, 9, or 10 amino acids from the N-terminus, C-terminus or both N- and C-termini. In some embodiments, at least two amino acids of SEQ ID NO: 1 are replaced by an internal cross-link. In some embodiments, at least two amino acids are replaced by an internal stitch. In some embodiments, at least two amino acids are replaced by an internal cross-link comprise two or more staples. In some embodiments, at least two amino acids are replaced by an internal cross-link comprising at least one staple and at least one stitch.

In some embodiments, provided herein are stapled alpha helical (SAH) peptides that mimic the functionality of the FOXP3/NFAT interface domain. In some embodiments, the SAH peptide inhibits oligomerization of FOXP3 and NFAT. In some embodiments, the SAH peptide comprises at least 70% sequence identity to one of SEQ ID NOS: 66-70. In some embodiments, the SAH peptide comprises at least 70% (e.g., 70%, 75%, 80%, 85%, 90%, 95%, 99%, 100%, or ranges therebetween) sequence similarity to one of SEQ ID NOS: 66-70. In some embodiments, the SAH peptide comprises at least 70% (e.g., 70%, 75%, 80%, 85%, 90%, 95%, 99%, 100%, or ranges therebetween) sequence identity to one of SEQ ID NOS: 66-70. In some embodiments, the peptide comprises 1-3 hydrocarbon staples. In some embodiments, the hydrocarbon staple(s) stabilize the peptides alpha helical character. In some embodiments, the hydrocarbon staple(s) are selected from i to i+4 and/or i to i+7 staples. In some embodiments, the SAH peptide comprises one or more non-natural amino acids, modified amino acids, amino acid analogs, and/or peptoid amino acids.

In some embodiments, provided herein are peptide amphiphiles (PAs) comprising: (a) an SAH peptide or cross-linked peptide described herein linked to (b) a hydrophobic domain. In some embodiments, the hydrophobic moiety comprises one or more acyl chains, lipids, fatty acids, or portions thereof. In some embodiments, the SAH peptide and the hydrophobic domain are directly, covalently linked. In some embodiments, the SAH peptide and the hydrophobic domain are connected via one or more linker moieties. In some embodiments, the one or more linker moieties are selected from the group consisting of a linker peptide, a structural peptide, poly(ethylene glycol) (PEG) linker, pamidobenzylocycarbonyl (PABC, PABA, or similar), an alkyl chain, a heteroalkyl chain, a substituted alkyl chain, a substituted heteroalkyl chain and a cleavable moiety. In some embodiments, the cleavable moiety is enzyme cleavable or chemically cleavable. In some embodiments, the cleavable moiety is cathepsin cleavable. In some embodiments, the cleavable moiety comprises a valine-citruline moiety. In some embodiments, the PA comprises an SAH peptide described herein linked to a hydrophobic domain via a valine-citruline moiety, a PABC/PABA moiety, and a PEG moiety. In some embodiments, a PA described herein further comprises one or more accessory moieties. In some embodiments, the accessory moiety is a label, therapeutic moiety, a targeting moiety, or a degradation moiety. In some embodiments, the accessory moiety is attached to the SAH peptide, the linker moiety, or the hydrophobic moiety.

In some embodiments, provided here are methods of inhibiting FOXP3 oligomerization (e.g., homodimerization or dimerization with NFAT) and/or function comprising administering an SAH peptide or a PA described herein to a cell or subject.

In some embodiments, provided herein are pharmaceutical compositions comprising a SAH peptide or a PA described herein. In some embodiments, provided herein are methods of treating cancer, an inflammatory condition, and/or an autoimmune disease comprising administering a pharmaceutical composition described herein to a cell or subject.

In some embodiments, provided herein is the use of a SAH peptide, PA, or pharmaceutical composition described herein for the treatment of cancer, an inflammatory condition, and/or an autoimmune disease.

BRIEF DESCRIPTION OF THE DRAWINGS

FIG. 3A-B. Accumulation of bioactive peptide using cathepsin-mediated cleavage from the lipid tail of peptide amphiphiles. (A) Representative images of N-terminal (left) or C-terminal (right) addition of the lipid tail, cathepsin cleavage sequence, and PABC spacer. Fluorochromes can be added to each piece to follow intracellular trafficking as shown in (B). Unstapled peptide (FITC)-laden PAs with a cathepsin cleavage site and PABC spacer show robust accumulation in HeLa cells over time compared to PAs lacking this functionality.

FIG. 4A-B. Generation of truncated FOXP3 proteins used for determination of SAH-FOXP3 specific binding. (A) Schematic depicting exemplary truncations. (B) Expression of truncated proteins.

FIG. 5A-C. Unstapled FOXP3 peptides are able to alter FOXP3-DNA binding at high concentrations. Preparation of FOXP3 proteins through In Vitro Transcription and Translation (IVTT) reticulocyte lysate: T7 DNA vectors (1 μg/25 μL) were incubated at 30° C. for 1.5 hr in reticulocyte lysate with T7 polymerase, amino acids and RNAsin per the manufacturer's protocol (TnT Coupled Reticulocyte Lysate System, Promega). IRDye700 labeled probe containing consensus sequence (A'A1A2; a DNA sequence previously published to bind FOXP3) for FOXP3 was incubated at room temperature for 15 mins with 2 μL FOXP3 reticulocyte lysate, in the presence of peptides (50-200 μM) using the Odyssey Infrared EMSA kit per manufacturer's protocol (Li-Cor). Reactions were then separated by electrophoresis on a 10% TBE gel and imaged using an Odyssey Imager (Li-Cor). (A) Increasing concentrations of native unstructured peptides (+)223-252, 229-259, and to a lesser extent 231-249, dissociate FOXP3 from DNA. (B/C) Only peptides comprising the dimerization domain are sufficient to dissociate FOXP3 from DNA.

FIG. 10A-B. Murine FOXP3 sequence summary (SEQ ID NO: 25 and SEQ ID NO: 75).

DEFINITIONS

Figure 1A:
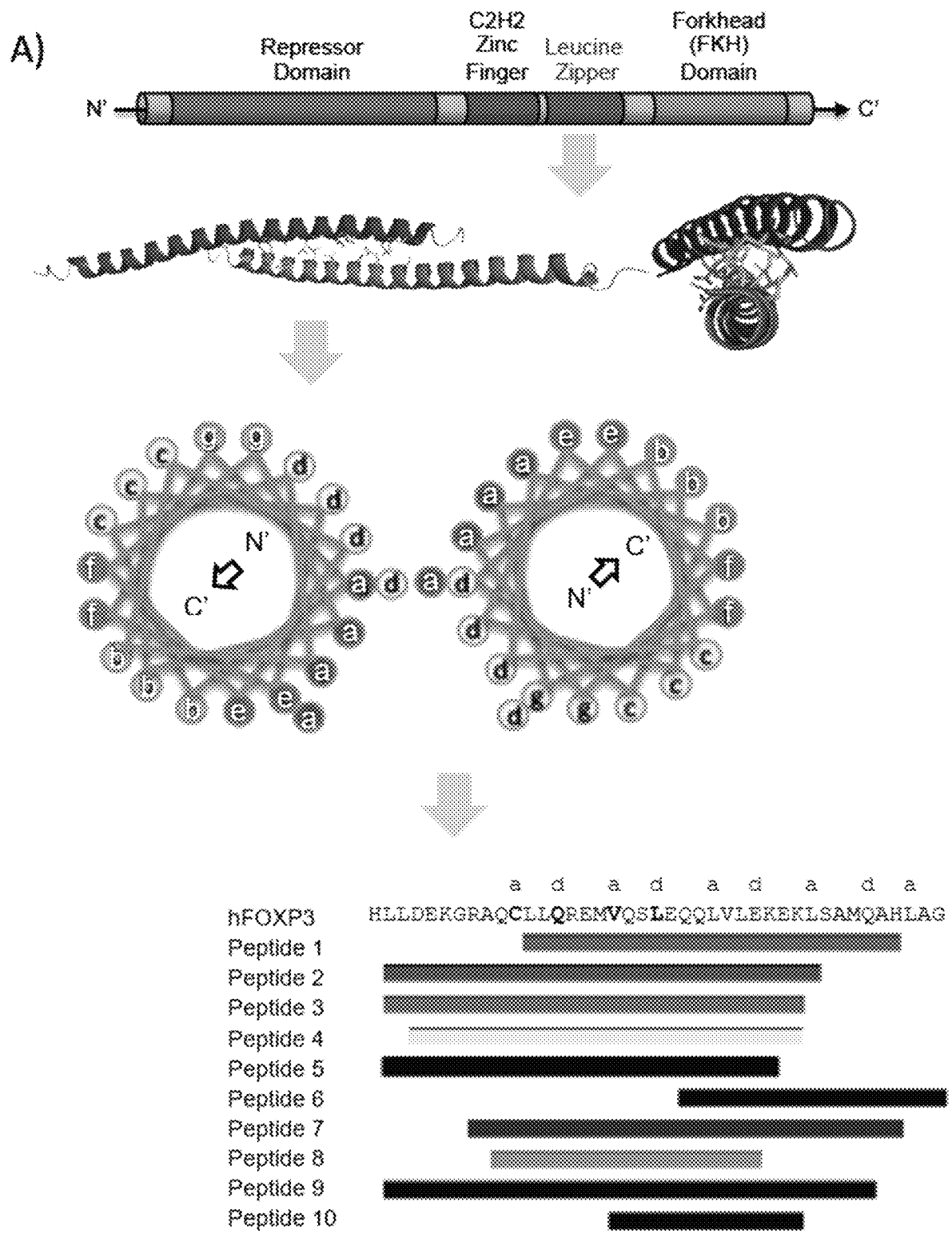
FIG. 1A-B. Design, characterization, and functional testing of SAH-FOXP3DDs. (A) Design strategy for SAHs targeting the coiled-coil dimerization domain of FOXP3 (SEQ ID NO: 25). (B) Example circular dichroism showing unstapled and stapled SAH-FOXP3DDs are helical in solution.

The terminology used herein is for the purpose of describing the particular embodiments only, and is not intended to limit the scope of the embodiments described herein. Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide" is a reference to one or more peptides and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGy"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" refers to a variant of a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that isn't the most common sequence in nature), or may be a peptide that is not a subsequence of a naturally occurring protein or polypeptide.

As used herein, the term "artificial peptide" refers to a peptide having a distinct amino acid sequence from those found in natural peptides and/or proteins. An artificial protein is not a subsequence of a naturally occurring protein, either the wild-type (i.e., most abundant) or mutant versions thereof. An "artificial peptide," as used herein, may be produced or synthesized by any suitable method (e.g., recombinant expression, chemical synthesis, enzymatic synthesis, etc.).

As used herein, the terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimetics include chemically modified peptides, peptoids (side chains are appended to the nitrogen atom of the peptide backbone, rather than to the α-carbons), β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural reside. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, "stapling" or "hydrocarbon-stapling" is a process by which two terminally unsaturated amino acid side chains in a polypeptide chain react with each in the presence of a ring closing metathesis catalyst to generate a C—C double bonded cross-link between the two amino acids (a "staple"). Stapling engenders constraint on a secondary structure, such as an alpha helical structure. The length and geometry of the cross-link can be optimized to improve the yield of the desired secondary structure content. The constraint provided can, for example, prevent the secondary structure to unfold and/or can reinforce the shape of the secondary structure, and thus makes the secondary structure more stable. Multiple stapling is also referred to herein as "stitching." In certain embodiments, hydrocarbon staples are the result of ring-closing olefin metathesis (RCM) of hindered α-methyl, α-alkenyl amino acids.

As used herein, the term "interacting face" refers to the amino acid residues on the side of a peptide (e.g., alpha helix) that interacts with specifically or binds specifically a protein (e.g., FOXP3, NFAT, etc.).

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a human subject that is being treated for a disease or condition.

As used herein, the term "effective amount" refers to the amount of an agent sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" means an approach to obtaining a beneficial or intended clinical result. The beneficial or intended clinical result may include alleviation of symptoms, a reduction in the severity of the disease, inhibiting a underlying cause of a disease or condition, steadying diseases in a non-advanced state, delaying the progress of a disease, and/or improvement or alleviation of disease conditions.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a hydrophobic segment (e.g., non-peptide moiety) linked a peptide segment, such that the peptide amphiphile self-assembles into a nanostructure (e.g., with the hydrophobic segment buried and the peptide segment exposed on the surface) under suitable aqueous conditions. The peptide amphiphile may express a net charge at physiological pH, either a net positive or negative net charge, or may be zwitterionic (i.e., carrying both positive and negative charges).

As used herein and in the appended claims, the term "hydrophobic segment" refers to a chemical moiety of sufficient length and hydrophobic character to provide amphiphilic behavior and micelle (or nanosphere or nanofiber) formation in water or another polar solvent system.

As used herein, the term "immunotherapy" refers to the treatment or prevention of a disease or condition by a method comprising inducing, enhancing, suppressing or otherwise modifying an immune response. Some embodiments herein comprise immunotherapies.

As used herein, the terms "adoptive immunotherapy" and "adoptive cell transfer" refer to the transfer of immunocompetent cells (e.g., T cells, engineered Tregs, etc.), e.g., for the treatment of cancer or autoimmune diseases (June, C. H., ed., 2001, In: Cancer Chemotherapy and Biotherapy: Principles and Practice, Lippincott Williams & Wilkins, Baltimore; Vonderheide et al., 2003, Immun. Research 27:1-15; incorporated by reference in its entirety). Some embodiments herein comprise adoptive immunotherapy.

DETAILED DESCRIPTION

Although tumor-specific T cells exist, regulatory T cells (Tregs), which exquisitely rely on FOXP3, are actively recruited by tumors and represent a major barrier to effective anti-tumor immunity. In the age of cancer immunotherapy, new agents to control Tregs are urgently needed. Targeting FOXP3 has ramifications for amplifying anti-tumor immune responses to a broad array of refractory malignancies thought to be immunologically silent. In some embodiments, the peptides described herein are used alone (stapled and/or in peptide amphiphiles), or in conjunction with other immune therapies (e.g., tumor cell vaccines, checkpoint inhibitors, chimeric antigen receptor (CAR) T cells), or following allogeneic stem cell transplantation.

In some embodiments, hydrocarbon stapled peptides and/or peptide amphiphiles are used to inhibit FOXP3 (e.g., prevent FOXP3 oligomerization (e.g., homodimerization, dimerization with NFAT, etc.)) and corrupt Treg activity. FOXP3 is one of four members of the forkhead (FOX) transcription factor family characterized by the presence of a N-terminal transcription repressor domain followed by a C2H2 zinc finger (ZF), a coiled-coiled leucine zipper (LZ), and a C-terminal winged-helix/forkhead (FKH) DNA binding domain. FOXP3 is expressed in Tregs with little to no expression in other cells. Naturally occurring point mutations and small in-frame deletions within the coding region of FOXP3 in patients with IPEX (immunodysregulation, polyendocrinopathy, enteropathy, X-linked syndrome) are primarily localized to two distinct dimerization interfaces highlighting critical structure/function relationships. FOXP3 sequence, structure, and function are highly conserved in humans and mice reflecting shared mechanisms of action allowing for meaningful pre-clinical translation. The crystal structures of critical FOXP3 PPI interfaces have been determined (Bandukwala et al., 2011; Song et al., 2012; herein incorporated by reference in their entireties).

Leucine Zipper Coiled-Coiled (LZCC) Dimerization Domain (DD) is necessary and sufficient for FOXP3 homodimerization. The crystal structure of mFOXP3 shows that FOXP3 homodimerization occurs through a two-stranded anti-parallel α-helical coiled-coil. Within the coiled-coil, a regular heptad repeat (positions a→g) aligns a generally hydrophobic core (positions a and d), charged and polar residues necessary for salt-bridging and dimer stabilization flank the interface (positions e and g), and solvent-exposed polar residues enhance solubility (positions b, c, and f). The interface accessible surface area of the FOXP3 coiled-coil is 966 Å (16% of total), compared to the average of 1492 Å in other protein dimers. Additionally, empty space of approximately 260 Å in this interface leads to large packing holes. Non-hydrophobic core residues lead to further dimerization instability.

The NFAT interface domain is involved in FOXP3 dimerization with NFAT. Treg activity is modulated by a cooperative complex between the transcription factor NFAT and FOXP3, a lineage specification factor for Tregs. FOXP3/NFAT interaction is required to repress expression of IL-2, upregulate expression of the Treg markers CTLA4 and CD25, and confer suppressor function to Tregs.

Provided herein are peptide-based therapeutics that target FOXP3 and methods of use thereof to decrease the immunosuppressive effects of Tregs and inhibit immune dysregulation, while sparring inhibition of activated cytotoxic T cells, for example, in the context of anti-tumor immune responses, autoimmunity, inflammatory conditions, etc. In some embodiments, compositions and methods herein inhibit homodimerization of FOXP3. In some embodiments, compositions and methods herein inhibit FOXP3/NFAT heterodimerization.

In some embodiments, provided herein are stapled or otherwise stabilized peptides (e.g., alpha helical peptides). Compositions and methods related to such stabilization are described, for example, in U.S. Pub. No. 2014/0370042 and WO 2009/108261 (herein incorporated by reference in their entireties) and elsewhere.

In some embodiments, provided herein are therapeutic stapled alpha helical (SAH) peptides of FOXP3's leucine zipper domain, for example, for the treatment of cancer and autoimmune disease. In some embodiments, the SAH peptides inhibit endogenous FOXP3 from oligomerizing in the cell, which is necessary for FOXP3 function.

Homodimerization of FOXP3 is mediated via an antiparallel coiled-coil interaction between two FOXP3 leucine-zipper domains. During development of embodiments herein, using the crystal structure of this dimerization interface as a molecular template, a series of hydrocarbon-stapled peptides (SAH-FOXP3s) recapitulating the natural α-helical secondary structure of this region were designed and prepared. SAH peptides are chemically modified by connecting amino acids with a hydrocarbon linker through olefin metathesis using ruthenium-based catalysis. Hydrocarbon stapling of amphipathic helical peptides stabilizes a peptide's natural α-helical structure, inhibits proteolysis, enhances cellular permeability, and allows for effective targeting of intracellular protein-protein interactions. Experiments conducted during development of embodiments herein demonstrate that SAH-FOXP3s bind recombinant FOXP3ΔN and FOXP3 LZCC with nanomolar specificity. The unstapled version of each peptide showed no binding, confirming the importance of the reinforced α-helical structure. Strikingly, 4 of the SAH-FOXP3s tested show dose-dependent inhibition of FOXPΔN:DNA binding in electrophoretic mobility shift assays (EMSAs). The relative potency of the SAH-FOXP3s correlated to their binding affinities to recombinant FOXP3ΔN and LZCC, further confirming specificity of action. Following confirmation that lead SAH-FOXP3s are not toxic to Tregs and conventional T cells using LDH-release assays, experiments were conducted demonstrating that two of the compounds effectively inhibit Treg-mediated immune suppression using in vitro T cell suppression assays. Flow cytometric analysis of treated-Tregs indicates that the transcriptional profile of Tregs is altered, as evidenced by differences in cell surface expression of T cell-associated markers.

In some embodiments, provided herein are therapeutic stapled alpha helical (SAH) peptides of FOXP3's NFAT interface domain, for example, for the treatment of cancer and autoimmune disease. In some embodiments, the SAH peptides inhibit endogenous FOXP3 and NFAT from oligomerizing in the cell.

In some embodiments, SAH-FOXP3 and SAH-FOXP3/NFAT peptide find use as molecular probes and therapeutics to study FOXP3 transcriptional control and to target Tregs (e.g., in cancer patients), for example, to augment the effectiveness of cancer immunotherapies such as tumor cell vaccines, checkpoint inhibition, chimeric antigen receptor (CAR) T cell therapy, or following allogeneic stem cell transplantation.

FOXP3 is one of four members of the forkhead (FOX) transcription factor family characterized by the presence of a N-terminal transcription repressor domain followed by a $C_2H_2$ zinc finger (ZF), a coiled/coiled leucine zipper (LZ), and a C-terminal winged-helix/forkhead (FKH) DNA binding domain (ref. 11; incorporated by reference in its entirety). There are two α-helical domains within FOXP3 (e.g., the LZ domain and the FOXP3/NFAT1 binding interface in the FKH domain). In some embodiments, these alpha helical domains are targeted using peptide mimicry.

The LZ domain is necessary and sufficient for FOXP3 homodimerization (Song et al. *Cell Rep* 1, 665-675 (2012); incorporated by reference in its entirety). The crystal structure of mFOXP3 shows that homodimerization of FOXP3 occurs through a two-stranded anti-parallel α-helical coiled-coil (Song et al. *Cell Rep* 1, 665-675 (2012); incorporated by reference in its entirety). Within the coiled-coil, a regular heptad repeat (positions a→g) aligns a generally hydrophobic core (positions a and d), charged and polar residues necessary for salt-bridging and dimer stabilization flank the interface (positions e and g), and solvent-exposed polar residues enhance solubility (positions b, c, and f). The interface accessible surface area of the FOXP3 coiled-coil is 966 Å$^2$ (16% of total), compared to the average of 1492 Å$^2$ in other protein dimers (Song et al. *Cell Rep* 1, 665-675 (2012); incorporated by reference in its entirety). Additionally, empty space of approximately 260 Å$^3$ in this interface leads to large packing holes. Non-hydrophobic core residues lead to further dimerization instability. Such flexibility and accessibility indicates that the FOXP3 coiled-coil interaction is dynamic and transient and thus is highly targetable through peptide interference. Clinically-relevant single point mutations, within this region that disrupt FOXP3 dimerization and inhibit Treg suppressive function (Song et al. *Cell Rep* 1, 665-675 (2012); incorporated by reference in its entirety).

The crystal structure of FOXP2 (conserved with FOXP3) bound to NFAT1:DNA indicates that the NFAT1:FOXP3 interface is dominated by an α-helical segment that contains polar residues with hydrated pockets between major contact points (Wu et al. *Cell* 126, 375-387 (2006); incorporated by reference in its entirety). These structural features point to a targetable interface and may explain why NFAT1:FOXP3 does not form stable complexes in the absence of DNA. Mutagenesis of FOXP3 residues necessary for NFAT1, but not DNA, binding abrogates gene expression (IL-2, CTLA-4, and CD25) and inhibits Treg suppressive function points (Wu et al. *Cell* 126, 375-387 (2006); incorporated by reference in its entirety). Although not shown to be specific, a non-structured peptide spanning a loop domain and Wing1 region within the FKH domain of FOXP3 was shown to partially inhibit NFAT1:FOXP3 interaction and decrease tumor burden in mice when coincidentally treated with chemotherapy or a tumor antigen vaccine points (Lozano, T. et al. *J Immunol* 195, 3180-3189, (2015); incorporated by reference in its entirety). The peptide was cell permeable and required cellular introduction using a plasmid transfection system points (Lozano, T. et al. *J Immunol* 195, 3180-3189, (2015); incorporated by reference in its entirety).

FOXP3 is expressed in Treg cells with little to no expression in other cells. FOXP3's function and immune regulation are not binary phenomena, as reduction and not absence of FOXP3 expression leads to dose-dependent immune reactivation and autoimmune disease (Balandina et al. *Blood* 105, 735-741(2005); Wan & Flavell. *Nature* 445, 766-770 (2007); incorporated by reference in their entireties), indicating that not all cellular FOXP3 needs to be inhibited to amplify the endogenous immune response.

In certain embodiments, the FOXP3 peptides of this disclosure have 1, 2, 3, 4, 5, 6, 7, 8, 9, 10, 11, 12, 13, 14, or 15 amino acid substitutions in SEQ ID NO: 1 (e.g., 1, 2, 3, 4, 5, 6, 7, 8, 9, 10, 11, 12, 13, 14, or 15 amino acids are conservatively or non-conservatively substituted). In some embodiments, the amino acid substitutions in SEQ ID NO: 1 are on one or both the interacting and non-interacting side of the alpha helix. In some embodiments, greater variability is permitted in the non-interacting side of the alpha helix of the FOXP3 peptide dimerization interface than on the interacting side. In some embodiments, most or all of the amino acids (e.g., 5, 4, 3, 2, or 1 amino acids) of the non-interacting face of the helix are substituted (e.g., conservative or non-conservative amino acid substitutions or alanine). In certain embodiments, the interacting face of the helix of these peptides has 1 to 10, 1 to 9, 1 to 8, 1 to 7, 1 to 6, 1 to 5, 1 to 4, 1 to 3, 1 to 2, or 1 amino acid substitution(s). In some instances, the substitution is a conservative amino acid substitution. In other instances, the substitution is a non-conservative amino acid substitution. In some instances, the substitutions are both conservative and non-conservative amino acid substitutions.

In some embodiments, provided herein are FOXP3 peptides that are at least 50% (e.g., 40%, 45%, 50%, 55%, 60%, 65%, 70%, 75%, 80%, 85%, 90%, 95%, 98%, 99%, 99.5%, or 100%) identical to SEQ ID NO: 1. In some embodiments, the variability in amino acid sequence of SEQ ID NO: 1 is on one or both the interacting and non-interacting side of the alpha helix. Just about every one of the amino acids on the non-interacting face of the FOXP3 helix can be varied. The amino acids on the interacting face of the helix can also be varied.

In certain embodiments, the FOXP3/NFAT peptides of this disclosure have 1, 2, 3, 4, 5, 6, 7, 8, 9, 10, 11, 12, 13, 14, or 15 amino acid substitutions in SEQ ID NO: 66 (e.g., 1, 2, 3, 4, 5, 6, 7, 8, 9, 10, 11, 12, 13, 14, or 15 amino acids are conservatively or non-conservatively substituted). In some embodiments, the amino acid substitutions in SEQ ID NO: 66 are on one or both the interacting and non-interacting side of the alpha helix. In some embodiments, greater variability is permitted in the non-interacting side of the alpha helix of the FOXP3/NFAT peptide dimerization interface than on the interacting side. In some embodiments, most or all of the amino acids (e.g., 5, 4, 3, 2, or 1 amino acids) of the non-interacting face of the helix are substituted (e.g., conservative or non-conservative amino acid substitutions or alanine). In certain embodiments, the interacting face of the helix of these peptides has 1 to 10, 1 to 9, 1 to 8, 1 to 7, 1 to 6, 1 to 5, 1 to 4, 1 to 3, 1 to 2, or 1 amino acid substitution(s). In some instances, the substitution is a conservative amino acid substitution. In other instances, the substitution is a non-conservative amino acid substitution. In some instances, the substitutions are both conservative and non-conservative amino acid substitutions.

In some embodiments, provided herein are FOXP3/NFAT peptides that are at least 50% (e.g., 40%, 45%, 50%, 55%, 60%, 65%, 70%, 75%, 80%, 85%, 90%, 95%, 98%, 99%, 99.5%, or 100%) identical to SEQ ID NO: 66. In some embodiments, the variability in amino acid sequence of SEQ ID NO: 66 is on one or both the interacting and non-interacting side of the alpha helix. Just about every one of the amino acids on the non-interacting face of the FOXP3 helix can be varied. The amino acids on the interacting face of the helix can also be varied.

In order to decrease the likelihood of membrane disruption, in some embodiments, the peptides are optimized by lowering the overall peptide hydrophobicity. This can for example be achieved by substituting especially hydrophobic residues with an amino acid with lower hydrophobicity (e.g., alanine). In some embodiments, membrane disruption is lowered by reducing the overall positive charge of the peptide (e.g., by substituting basic residues with uncharged or acidic residues). In certain instances, both the overall peptide hydrophobicity and the overall positive charge of the peptide are lowered.

In some embodiments, the peptides herein are stabilized by the inclusion of two or more substitutions to replace, e.g., an amino acid of the FOXP3 LZ domain peptide or NFAT interface peptide with a non-natural amino acid, to facilitated intra-peptide crosslinking, stapling and/or stitching.

The present disclosure provides structurally stabilized peptides related to FOXP3 LZ domain peptide or NFAT interface peptide comprising at least two modified amino acids joined by an internal (intramolecular) cross-link (or staple). Stabilized peptides as described herein include stapled peptides and stitched peptides as well as peptides containing multiple stitches, multiple staples or a mix or staples and stitches.

In certain embodiments, one or more of the FOXP3 LZ domain peptides or NFAT interface peptides described herein are stabilized by peptide stapling (see, e.g., Walensky, J. Med. Chem., 57:6275-6288 (2014), the contents of which are incorporated by reference herein in its entirety). A peptide is "stabilized" in that it maintains its native secondary structure. For example, stapling allows a polypeptide, predisposed to have an α-helical secondary structure, to maintain its native α-helical conformation. This secondary structure increases resistance of the polypeptide to proteolytic cleavage and heat, and also may increase target binding affinity, hydrophobicity, and cell permeability. Accordingly, the stapled (cross-linked) polypeptides described herein have improved biological activity relative to a corresponding non-stapled (un-cross-linked) polypeptide.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., J. Org. Chem., 66: 5291-5302, 2001; Angew et al., Chem. Int. Ed. 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacing. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008/121767 and WO 2010/068684, which are both hereby incorporated by reference in their entirety. In some instances, staples, as used herein, can retain the unsaturated bond or can be reduced.

In certain embodiments, one or more of the polypeptides described herein are stabilized by, e.g., hydrocarbon stapling. In some embodiments, the stapled peptide is a polypeptide comprising or consisting of amino acids 213-261 of human FOXP3 (214-262 mouse FOXP3), or comprising 1 to 10 (e.g., 1, 2, 3, 4, 5, 6, 7, 8) amino acid substitutions, deletions and/or insertions therein). For example, the stapled peptide can include at least two (e.g., 2, 3, 4, 5, 6, 7, 8) amino acid substitutions, wherein the substituted amino acids are separated by two, three, or six amino acids, and wherein the substituted amino acids are non-natural amino acids with olefinic side chains. There are many known non-natural or unnatural amino acids any of which may be included in the peptides of the present disclosure. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, or glycosylated.

Hydrocarbon stapled polypeptides include one or more tethers (linkages) between two non-natural amino acids, which tether significantly enhances the α-helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence ... X1, X2, X3, X4, X5, X6, X7, X8, X9 ..., cross-links between X1 and X4, or between X1 and X5, or between X1 and X8 are useful hydrocarbon stapled forms of that peptide, as are cross-links between X2 and X5, or between X2 and X6, or between X2 and X9, etc. The use of multiple cross-links (e.g., 2, 3, 4, or more) is also contemplated. The use of multiple cross-links is very effective at stabilizing and optimizing the peptide, especially with increasing peptide length. Thus, the disclosure encompasses the incorporation of more than one crosslink within the polypeptide sequence to either further stabilize the sequence or facilitate the structural stabilization, proteolytic resistance, acid stability, thermal stability, cellular permeability, and/or biological activity enhancement of longer polypeptide stretches. Additional description regarding making and use of hydrocarbon stapled polypeptides can be found, e.g., in U.S. Patent Publication Nos. 2012/0172285, 2010/0286057, and 2005/0250680, the contents of all of which are incorporated by reference herein in their entireties.

In one aspect, a FOXP3 stapled polypeptide has the formula (I),

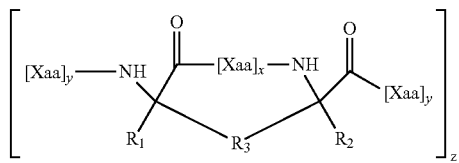

wherein:
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

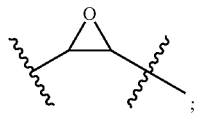

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10);
and each Xaa is independently an amino acid. In one embodiments, the N-terminal $[Xaa]_y$ of formula (I) is not present, RAQCLLQREMVQSLE (SEQ ID NO: 71). In some embodiments, $[Xaa]_x$ is QLVLEK (SEQ ID NO: 72). In some embodiments, the C-terminal $[Xaa]_y$ of formula (I) is KLSAMQAH (SEQ ID NO: 73). The FOXP3 stapled polypeptides can include an amino acid sequence described herein.

In some embodiments, the tether includes an alkyl, alkenyl, or alkynyl moiety (e.g., $C_5$, $C_8$, or $C_{11}$ alkyl, a $C_5$, $C_8$, or $C_{11}$ alkenyl, or $C_5$, $C_8$, or $C_{11}$ alkynyl). In some embodiments, the tethered amino acid is alpha disubstituted (e.g., $C_1$-$C_3$ or methyl).

In some instances, x is 2, 3, or 6. In some instances, each y is independently an integer between 1 and 15, or 3 and 15. In some instances, $R_1$ and $R_2$ are each independently H or $C_1$-$C_6$ alkyl. In some instances, $R_1$ and $R_2$ are each independently $C_1$-$C_3$ alkyl. In some instances, at least one of $R_1$ and $R_2$ are methyl. For example, $R_1$ and $R_2$ can both be methyl. In some instances, $R_3$ is alkyl (e.g., $C_8$ alkyl) and x is 3. In some instances, $R_3$ is $C_{11}$ alkyl and x is 6. In some instances, $R_3$ is alkenyl (e.g., $C_8$ alkenyl) and x is 3. In some instances, x is 6 and $R_3$ is $C_{11}$ alkenyl. In some instances, $R_3$ is a straight chain alkyl, alkenyl, or alkynyl. In some instances, $R_3$ is —$CH_2$—$CH_2$—$CH_2$—CH=CH—$CH_2$—$CH_2$—$CH_2$—.

In another aspect, the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as:

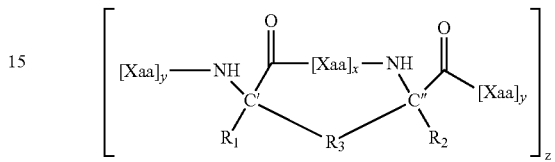

the C' and C" disubstituted stereocenters can both be in the R configuration or they can both be in the S configuration, e.g., when x is 3. When x is 6, the C' disubstituted stereocenter is in the R configuration and the C" disubstituted stereocenter is in the S configuration. The $R_3$ double bond can be in the E or Z stereochemical configuration.

In some instances, $R_3$ is $[R_4—K—R_4]_n$; and $R_4$ is a straight chain alkyl, alkenyl, or alkynyl.

In some embodiments, the disclosure features internally cross-linked ("stapled" or "stitched") peptides comprising the amino acid sequence RAQCLLQREMVQSLEQQLVLEKEKLSAMQAH (SEQ ID NO: 10), wherein the side chains of two amino acids separated by two, three, or six amino acids are replaced by an internal staple; the side chains of three amino acids are replaced by an internal stitch; the side chains of four amino acids are replaced by two internal staples, or the side chains of five amino acids are replaced by the combination of an internal staple and an internal stitch. In certain instances, the amino acids at one or more of positions 4, 8, and 9 of SEQ ID NO: 10 are not replaced with a staple or stitch. In certain instances, the amino acids at one or more of positions 2, 5, and 6 of SEQ ID NO: 10 are not replaced with a staple or stitch. The stapled/stitched peptide can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Exemplary FOXP3 stapled peptides are shown in Table 2. In certain embodiments, the stapled polypeptide comprises or consists of the amino acid sequence set forth in any one of SEQ ID NOs: 1 to 64. In one embodiment, the FOXP3 stapled peptide has the amino acid sequence set forth in SEQ ID NO: 44.

Embodiments herein are not limited to hydrocarbon tethers; other tethers are also employed in the peptides described herein. For example, in some embodiments, other tethers include one or more of an ether, thioether, ester, amine, or amide, or triazole moiety. In some cases, a naturally occurring amino acid side chain is incorporated into the tether. For example, a tether is coupled with a functional group such as the hydroxyl in serine, the thiol in cysteine, the primary amine in lysine, the acid in aspartate or glutamate, or the amide in asparagine or glutamine. Accordingly, in some embodiments, a tether is created using naturally occurring amino acids rather than using a tether that is made by coupling two non-naturally occurring amino acids. It is also possible to use a single non-naturally occurring amino acid together with a naturally occurring amino acid. Triazole-containing (e.g., 1, 4 triazole or 1, 5 triazole) crosslinks can be used (see, e.g., Kawamoto et al. 2012 *Journal of Medicinal Chemistry* 55:1137; WO 2010/060112). In addition, other methods of performing different types of stapling are well known in the art and can be employed with the FOXP3 peptides described herein (see, e.g., *Lactam stapling*: Shepherd et al., *J. Am. Chem. Soc.*, 127:2974-2983 (2005); UV-cycloaddition stapling: Madden et al., *Bioorg. Med. Chem. Lett.*, 21:1472-1475 (2011); Disulfide stapling: Jackson et al., *Am. Chem. Soc.*, 113:9391-9392 (1991); Oxime stapling: Haney et al., *Chem. Commun.*, 47:10915-10917 (2011); Thioether stapling: Brunel and Dawson, *Chem. Commun.*, 552-2554 (2005); *Photoswitchable stapling*: J. R. Kumita et al., *Proc. Natl. Acad. Sci. U.S.A.*, 97:3803-3808 (2000); Double-click stapling: Lau et al., *Chem. Sci.*, 5:1804-1809 (2014); *Bis-lactam stapling*: J. C. Phelan et al., *J. Am. Chem. Soc.*, 119:455-460 (1997); and Bis-arylation stapling: A. M. Spokoyny et al., *J. Am. Chem. Soc.*, 135: 5946-5949 (2013)).

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while tethers spanning from amino acids i to i+3, i to i+4, and i to i+7 are common in order to provide a tether that is primarily on a single face of the alpha helix, the tethers can be synthesized to span any combinations of numbers of amino acids and also used in combination to install multiple tethers.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation, aminohydroxylation or dihydroxylation) to provide one of compounds below.

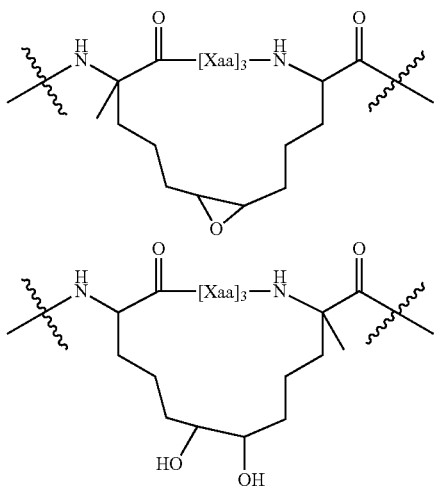

Either the epoxide moiety or one of the free hydroxyl moieties can be further functionalized. For example, the epoxide can be treated with a nucleophile, which provides additional functionality that can be used, for example, to attach a therapeutic agent. Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO-(CH_2CH_2O)_n-CH_2CH_2-Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as $-NH(CH_2)_nC(O)-$, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech. Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof. α,α-Disubstituted non-natural amino acids containing olefinic side chains of varying length can be synthesized by known methods (Williams et al. *J. Am. Chem. Soc.*, 113:9276, 1991; Schafmeister et al., *J. Am. Chem Soc.*, 122:5891, 2000; and Bird et al., *Methods Enzymol.*, 446:369, 2008; Bird et al, *Current Protocols in Chemical Biology*, 2011). For peptides where an i linked to i+7 staple is used (two turns of the helix stabilized) either: a) one S5 amino acid and one R8 is used; or b) one S8 amino acid and one R5 amino acid is used. R8 is synthesized using the same route, except that the starting chiral auxillary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., *Org. Synth.*, 80:31, 2003).

Again, methods suitable for obtaining (e.g., synthesizing), stapling, and purifying the peptides disclosed herein are also known in the art (see, e.g., Bird et. al., *Methods in Enzymol.*, 446:369-386 (2008); Bird et al, *Current Protocols in Chemical Biology*, 2011; Walensky et al., *Science*, 305:1466-1470 (2004); Schafmeister et al., *J. Am. Chem. Soc.*, 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the stapled (cross-linked) polypeptides of the invention can be assayed, for example, using the methods described below.

In some embodiments, provided herein are peptides comprising an alpha helical segment that inhibits FOXP3 oligomerization (e.g., peptide mimics of FOXP3's leucine zipper domain, peptide mimics of the NFAT interface domain, etc.). In some embodiments, two amino acids (e.g., i and i+4, i and i+7, etc.) within the alpha helical segment are modified to allow hydrocarbon stapling between the two amino acids. In some embodiments, the hydrocarbon stapling stabilizes the alpha helix in the absence of a larger polypeptide, and allows the peptide in disrupt FOXP3 oligomerization. Examples of stapling methods are described by Bird et al., Methods Enzymol 2008, 446, 369-386; Madden et al., Chem Commun 2009, 37, 5588-5590; Kim et al., Org Lett 2010, 12, 3046-3049; Bird et al., PNAS 2010, 107, 14093-14098; Jacobsen et al., J Org Chem 2011, 76, 1228-1238 and Verdine & Hilinski, Methods Enzymol 2012, 503, 3-33. In some embodiments peptides comprise at least one, two, or three "staples."

In some embodiments, the peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) described herein are modified to enhance biostability and/or biocompatibility, to extend the serum half-life, to prevent/inhibit/reduce clearance (e.g., by the kidneys), and/or to enhance therapeutic efficacy. Modification may include substitution/deletion/addition of amino acids from the sequences herein. In some embodiments, peptide comprises one or more substitutions (e.g., 1, 2, 3, 4, 5, 6, 7, 8, 9, 10, 11, 12, 13, 14, 15, 16, 17, 18, 19, 20, or ranges therebetween) relative to a peptide sequence provided herein. In some embodiments, a peptide (e.g., modified peptides, stapled peptides, peptidomimetics, peptide amphiphiles, etc.) that inhibits FOXP3 oligomerization (e.g., peptide mimics of FOXP3's leucine zipper domain, peptide mimics of the NFAT interface domain, etc.) comprises a truncation (or deletion) relative to a peptide sequence described herein. In some embodiments, a truncation (or deletion) is at the C-terminus, N-terminus, or internally. In some embodiments, a peptide (e.g., modified peptides, stapled peptides, peptidomimetics, peptide amphiphiles, etc.) that inhibits FOXP3 oligomerization (e.g., peptide mimics of FOXP3's leucine zipper domain, peptide mimics of the NFAT interface domain, etc.) comprises at least 70% (e.g., 70%, 75%, 80%, 85%, 90%, 95%, 99%, 100%) sequence identity with all or a portion of a peptide sequence provided herein. In some embodiments, a peptide (e.g., modified peptides, stapled peptides, peptidomimetics, peptide amphiphiles, etc.) that inhibits FOXP3 oligomerization (e.g., peptide mimics of FOXP3's leucine zipper domain, peptide mimics of the NFAT interface domain, etc.) comprises at least 70% (e.g., 70%, 75%, 80%, 85%, 90%, 95%, 99%, 100%) sequence similarity (e.g., conservative or semiconservative) with all or a portion of a peptide sequence provided herein. In some embodiments, a peptide (e.g., modified peptides, stapled peptides, peptidomimetics, peptide amphiphiles, etc.) that inhibits FOXP3 oligomerization (e.g., peptide mimics of FOXP3's leucine zipper domain, peptide mimics of the NFAT interface domain, etc.) comprises one or more modified or unnatural amino acids. In some embodiments, a peptide (e.g., modified peptides, stapled peptides, peptidomimetics, peptide amphiphiles, etc.) that inhibits FOXP3 oligomerization (e.g., peptide mimics of FOXP3's leucine zipper domain, peptide mimics of the NFAT interface domain, etc.) is a peptidomimetic. In some embodiments, a peptide (e.g., modified peptides, stapled peptides, peptidomimetics, peptide amphiphiles, etc.) that inhibits FOXP3 oligomerization (e.g., peptide mimics of FOXP3's leucine zipper domain, peptide mimics of the NFAT interface domain, etc.) is PEGylated, methylated, biotinylated, sumolyated, or otherwise modified.

A naturally occurring amino acid within the peptide sequences herein may be replaced with, for example, a non-naturally occurring amino acid such as, for example, norleucine, ornithine, norvaline, homoserine, and other amino acid residue analogues such as those described in Ellman et al., Meth. Enzym., 1991, 202, 301-336; incorporated by reference in its entirety. To generate such non-naturally occurring amino acid residues, the procedures of Noren et al., Science, 1989, 244, 182 and Ellman et al., supra (incorporated by reference in their entireties), can be used. Other suitable methods are described in White et al., Methods, 2013, 60, 70-74; Gentilucci et al., Curr Pharm Des 2010, 16, 3195-3203; Hodgson & Sanderson, Chem Soc Rev 2004, 33, 422-430 and Krebs et al., Chemistry 2004, 10:544-553; incorporated by reference in their entireties.

In some embodiments, the peptides described herein are further be modified. Some modifications may increase the stability and activity of a peptide to enable reduced dosing level or frequency, as well as enable alternative routes of administration. Examples of modifications of peptides that may increase stability, activity, specificity, and/or efficacy include: replacing labile amino acids with ones that increase stability and improve activity (e.g., replacing lysines/arginines that are recognized by trypsin with glutamine); replacing one or more L-amino acids with D-amino acids (See Powell et al. Pharm. Res., 1993, 10, 1268-1273; herein incorporated by reference in its entirety); reducing the size of the peptide removing non-essential sequences or individual residues (See Harris, Gut, 1994, 35(3 Suppl), S1-4; herein incorporated by reference in its entirety); PEGylating; C-terminal amidation or N-terminal acetylation as described in, for example, Brinckerhoff et al. (Int'l J. Cancer, 1999, 83, 326-334), or N-pyroglutamylation as described in, for example, Green et al. (J. Endocrinol., 2004, 180, 379-388); herein incorporated by reference in their entireties; conjugation of various fatty acids ranging from 4-18 chain length as described in, for example, DasGupta et al. (Biol. Pharma. Bull., 2002, 25, 29-36; herein incorporated by reference in its entirety); adding biodegradable modifications (e.g., polymers of N-acetylneuraminic acid (polysialic acids) as described in, for example, Georgiadis et al. (Cell. Mol. Life Sci., 2000, 57, 1964-1969; herein incorporated by reference in its entirety));

Other modifications may further include conjugation of the stapled peptide with a biologically active agent, label or diagnostic agent (e.g., as at the N-terminus, C-terminus, on an amino acid side chain, or at one or more modified or unmodified stapled sites, etc.). Such modification may be useful in delivery of the peptide to a cell, tissue, or organ. Such modifications may allow for targeting to a particular type of cell or tissue. Conjugation of an agent (e.g., a label, a diagnostic agent, a biologically active agent) to the peptide may be achieved in a variety of different ways. The agent may be covalently conjugated directly or indirectly, covalently or non-covalently. Conjugation may be by amide linkages, ester linkages, disulfide linkages, carbon-carbon bonds, carbamate, carbonate, urea, hydrazide, and the like. In some embodiments, the conjugation is cleavable under physiological conditions (e.g., enzymatically cleavable, cleavable with a high or low pH, with heat, light, ultrasound, x-ray, etc.). However, in some embodiments, the bond is not cleavable.

In some embodiments, peptidomimetics of the peptides described herein are provided. The use of peptides as lead compounds, and subsequently conversion into low-molecular-weight nonpeptide molecules (peptidomimetics), have successfully led to development of small-molecule antagonists of intracellular targets (Bottger et al., J. Mol. Biol., 1997, 269, 744-56; Bottger et al., Oncogene, 1996, 13, 2141-7; herein incorporated by reference in their entireties). Therefore, peptidomimetics have emerged as a powerful means for overcoming the obstacles inherent in the physical characteristics of peptides, improving their therapeutic potential (Kieber-Emmons et al., Curr. Opin. Biotechnol., 1997, 8, 435-41; Beeley, Trends Biotechnol., 1994, 12, 213-6; and Moore et al., Trends Pharmacol. Sci., 1994, 15, 124-9; herein incorporated by reference in their entireties). In some embodiments, compared to native peptides, peptidomimetics possess desirable pharmacodynamic properties superior to natural peptides, including good oral activity, long duration of action, better transport through cellular membranes, decreased rate of excretion, and decreased hydrolysis by peptidases.

In some embodiments, provided herein are fusions of (i) peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) with (ii) a modifier peptide or polypeptide. In some embodiments, the modifier is between 10 and 1000 amino acid residues in length (e.g., 10, 20, 30, 40, 50, 60, 70, 80, 90, 100, 150, 200, 250, 300, 350, 400, 450, 500, 550, 600, 650, 700, 750, 800, 850, 900, 950, 1000, or ranges therebetween). In some embodiments, the modifier is biostable and biocompatible. In some embodiments, the modifier extends the half-life and/or prevents clearance of the fusion relative to the peptide alone due to the extra size/bulk/mass of the fusion. In some embodiments, the modifier comprises a useful functionality (e.g., tissue or cellular localization, therapeutic benefit, detection, etc.). In some embodiments, the modifier is a naturally long-half-life protein or protein domain (e.g., an Fc domain, transferrin (Tf), albumin, etc.). In some embodiments, the modifier is an inert polypeptide (e.g., XTEN (Schellenberger et al. Nat Biotechnol. 2009 December; 27(12):1186-90; incorporated by reference in its entirety), a homo-amino acid polymer (Schlapschy et al. Protein Eng Des Sel. 2007; 20:273-284; incorporated by reference in its entirety), a proline-alanine-serine polymer (Schlapschy et al. Protein Eng Des Sel. 2013; 26:489-501; incorporated by reference in its entirety), or an elastin-like peptide (Floss et al. Trends Biotechnol. 2010; 28:37-45; incorporated by reference in its entirety), etc.). In some embodiments, the modifier is a negatively charged, highly sialylated peptide (e.g., carboxy-terminal peptide (Duijkers et al. Hum Reprod. 2002; 17:1987-1993; incorporated by reference in its entirety), etc.). In some embodiments, a modifier is a fragment or a variant of transferrin, albumin, an Fc domain, carboxy-terminal peptide, proline-alanine-serine polymer, elastin-like peptide, or XTEN.

In some embodiments, provided herein are conjugates of (i) peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) with (ii) a non-peptide/non-polypeptide modifier element (e.g., compound, polymer, etc.). In some embodiments, the modifier element is biostable and biocompatible. In some embodiments, the modifier element extends the half-life and/or prevents clearance of the fusion relative to the peptide alone due to the extra size/bulk/mass of the conjugate. In some embodiments, the modifier element is a polymer, such as PEG, dextran, polysialic acids, hyaluronic acid, dextrin, hydroxyethyl-starch, poly(2-ethyl 2-oxazoline), etc. (Paust. Polymers 2014, 6, 160-178; incorporated by reference in its entirety). In some embodiments, conjugate is a glycosylated peptide.

In some embodiments, provided herein are peptide amphiphiles comprising (i) a peptide (e.g., staples peptide) described herein and (ii) a hydrophobic tail. In some embodiments, provided herein are nanostructures (e.g., micelles, nanofibers, nanospheres, etc.) comprising the peptide amphiphiles herein. In some embodiments, peptide amphiphiles and nanostructures thereof are provided as delivery vehicles for the peptides (e.g., modified peptides, stapled peptides, peptidomimetics, etc.) that inhibit FOXP3 oligomerization (e.g., peptide mimics of FOXP3's leucine zipper domain, peptide mimics of the NFAT interface domain, etc.) described herein. In some embodiments, provided herein are methods of treating a disease or condition (e.g., cancer, inflammations, autoimmune disease, etc.) comprising administering the tide amphiphiles or nanostructures thereof to a subject.

Peptide amphiphiles (PAs) are peptide-based molecules that self-assemble into nanostructures, such as nanofibers or nanosphere, depending on the physical and chemical characteristics of the peptide amphiphiles. Peptide amphiphiles typically comprise a bioactive peptide of interest linked (e.g., directly or via a structural peptide and or non-peptide linker) to a hydrophobic moiety (e.g., non-peptide moiety).

In some embodiments, the peptide segment of a PA comprises a peptide (e.g., modified peptide, stapled peptide, peptidomimetic, etc.) that inhibits FOXP3 oligomerization (e.g., peptide mimics of FOXP3's leucine zipper domain, peptide mimics of the NFAT interface domain, etc.) described herein. In some embodiments, the peptide segment additionally comprises a linker peptide or structural peptide between the peptide (e.g., modified peptide, stapled peptide, peptidomimetic, etc.) that inhibits FOXP3 oligomerization and the hydrophobic domain. In some embodiments, a structural peptide is a peptide that facilitates packing of the peptide amphiphiles into nanostructures. In some embodiments, noncovalent interactions (e.g., hydrogen bonds, beta sheet formation, van der Waals interactions, hydrophobic interactions, etc.) between structural peptides of adjacent PAs facilitate nanostructure formation and/or influence nanostructure size and/or shape.

In some embodiments, the hydrophobic segment of a PA comprises an acyl chain or lipid. For example, in some embodiments, the hydrophobic segment of a PA comprises a single, linear acyl chain of the formula: $C_{n-1}Hsub_{2n-1}C(O)$— where n=6-22. In some embodiments, the hydrophobic segment is a lipid. In some embodiments, the lipid molecule is a fatty acid. In some embodiments, the fatty acid comprises 6-24 carbons. In some embodiments, lipids that find use in embodiments herein are fatty acids. In some embodiments, fatty acids in the compositions herein are a short chain fatty acid (carbon chain of <6 carbons (e.g., formic acid, acetic acid, propionic acid, butyric acid, isobutyric acid, valeric acid, isovaleric acid, etc.)), a medium chain fatty acid (carbon chain of 6-12 carbons (e.g., caproic acid, caprylic acid, capric acid, lauric acid, etc.)), a long chain fatty acid (carbon chain of 13-21 carbons (e.g., myristic acid, palmitic acid, stearic acid, arachidic acid, etc.)), a very long chain fatty acid (carbon chain of >21 carbons (e.g., behenic acid, lignoceric acid, cerotic acid, etc.)), and/or any suitable combinations thereof. In some embodiments, the acyl chain portion of the fatty acid comprises $C_6$-$C_{24}$ (e.g., $C_6$, $C_8$, $C_{10}$, $C_{12}$, $C_{14}$, $C_{16}$, $C_{18}$, $C_{20}$, $C_{22}$, $C_{24}$, or ranges therebetween). In some embodiments, a hydrophobic segment comprises multiple acyl chains or lipids. In some embodiments, the lipid is a saturated fatty acid selected from caprylic acid, capric acid, lauric acid, myristic acid, palmitic acid, stearic acid, arachidic acid, behenic acid, lignoceric acid, and cerotic acid. In some embodiments, the lipid is a saturated fatty acid selected from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

In some embodiments, PAs comprise one or more linker moieties of other structural/functional moieties between the peptide (e.g., modified peptide, stapled peptide, peptidomimetic, etc.) that inhibits FOXP3 oligomerization (e.g., peptide mimics of FOXP3's leucine zipper domain, peptide mimics of the NFAT interface domain, etc.) described herein and the hydrophobic segment. A variety of linker groups are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, PABC (pamidobenzylocycarbonyl), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In some embodiments, the linker is cleavable (e.g., enzymatically (e.g., cathepsin cleavable (e.g., Valine-Citruline), TEV protease cleavable, etc.), chemically, photoinduced, etc.

In some embodiments, an exemplary PA is depicted in FIG. 3A and comprises a peptide (e.g., modified peptide, stapled peptide, peptidomimetic, etc.) that inhibits a specific PPI, valine-vitruline segment (e.g., cathepsin cleavable site), PABC (pamidobenzylocycarbonyl), PEG linker, and a pair of lipid tails. Other combinations of these elements with each other (e.g., alternative arrangement) or with other elements described herein is within the scope herein.

In some embodiments, the peptides, stapled peptides, and PAs described herein comprise or are linked to one or more accessory (or bioactive, or functional) moieties. In some embodiments, an accessory moiety is a targeting moiety, such as a ligand for a cell surface receptor, a cellular localization peptide, antibody (or antibody fragment), etc. In some embodiments, an accessory moiety is a therapeutic moiety, such as a toxin, chemotherapeutic agent, anti-inflammatory agent, etc. In some embodiments, an accessory moiety is a label, such as a fluorophore (e.g., small molecule), chromophore, radionuclide, etc.

In some embodiments, compositions comprising peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) described herein find use in the treatment and/or prevention of a wide range of diseases and conditions, such as, autoimmune diseases, cancer, inflammatory conditions, etc.

In some embodiments, the peptide-based compositions and methods described herein find use in the treatment of cancer. In some embodiments, compositions and methods herein relate to the treatment of cancer such as acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some cases, the method relates to the treatment of leukemia, hematologic malignancy, solid tumor cancer, prostate cancer, e.g., castration-resistant prostate cancer, breast cancer, Ewing's sarcoma, bone sarcoma, primary bone sarcoma, T-cell prolymphocyte leukemia, glioma, glioblastoma, liver cancer, e.g., hepatocellular carcinoma, or diabetes.

In some embodiments, the peptide-based compositions and methods described herein find use in the treatment of autoimmune diseases. As used herein, "autoimmune" diseases or disorders include any disorder, condition, or disease in which the immune system mounts a reaction against self-cells or self-tissues, due to a breakdown in the ability to distinguish self from non-self or otherwise. In some embodiments, compositions and methods herein relate to the treatment of an autoimmunedisease or disorder such as addison's disease, agammaglobulinemia, alopecia areata, amyloidosis, ankylosing spondylitis, anti-GBM/Anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune pancreatitis, autoimmune retinopathy, autoimmune urticarial, Axonal & neuronal neuropathy (AMAN), Balo disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Churg-Strauss, cicatricial pemphigoid, Cogan's syndrome, cold agglutinin disease, congenital heart block, Coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with Polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hypogammalglobulinemia, IgA Nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, multiple sclerosis, Myasthenia gravis, myositis, narcolepsy, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes (type I, II, or III), polymyalgia rheumatic, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome (SPS), subacute bacterial endocarditis (SBE), Susac's syndrome, sympathetic ophthalmia (SO), Takayasu's arteritis, temporal arteritis/Giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, and Wegener's granulomatosis (or Granulomatosis with Polyangiitis (GPA)).

In some embodiments, compositions comprising peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) described herein are provided as pharmaceutical compositions/preparations/formulations. Pharmaceutical preparations can be formulated from the compositions herein by drug formulation methods known to those skilled in the art.

Formulations are prepared using a pharmaceutically acceptable carrier composed of materials that are considered safe and effective, without causing undesirable biological side effects or unwanted interactions. Suitable carriers include, but are not limited to, saline, buffered saline, dextrose, water, glycerol, ethanol, and combinations thereof. The composition can be adapted for the mode of administration and can be in the form of, e.g., a pill, tablet, capsule, spray, powder, or liquid. In some embodiments, the pharmaceutical composition contains one or more pharmaceutically acceptable additives suitable for the selected route and mode of administration, such as coatings, fillers, binders, lubricant, disintegrants, stabilizers, or surfactants. These compositions may be administered by, without limitation, any parenteral route, including intravenous, intratumoral, intra-arterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g. mammalian e.g., human)) subjects in the form of liquids, including sterile, non-pyrogenic liquids for injection, emulsions, powders, aerosols, tablets, capsules, enteric coated tablets, or suppositories. In some embodiments, Treg manipulation by SAH-FOXP3 peptides and/or SAH-FOXP3/NFAT peptides is performed alone or in the context of other therapies including chemotherapy, antibody therapy, stem cell transplant, solid organ transplant, checkpoint inhibition, and adoptive T cell therapies.

In some embodiments, a subject is treated with (i) a composition comprising peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) described herein, as well as (ii) one or more additional (cancer or autoimmune) therapies.

In some embodiments, an additional therapy for co-administration with the peptide-based compositions herein is a cancer therapy. Such therapies include chemotherapy, immunotherapy, radiation, surgery, etc. In some embodiments, exemplary anticancer agents suitable for use in compositions and methods described herein include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, compositions comprising peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) described herein treat cancer by making the cancer less aggressive, making the cancer/tumor susceptible to other treatments (e.g., chemotherapy), inhibiting metastasis, killing cancer cells, etc.

In some embodiments, compositions comprising peptides (e.g., modified peptides, stapled peptides, peptidomimetics, peptide amphiphiles, etc.) that inhibit FOXP3 oligomerization (e.g., peptide mimics of FOXP3's leucine zipper domain, peptide mimics of the NFAT interface domain, etc.) described herein are administered before and/or after surgery to remove a tumor or cancerous tissue. In some embodiments, the peptide-based compositions and therapies described herein are administered before, during, or after another cancer treatment (e.g., immunotherapy, chemotherapy, etc.). In some embodiments, the peptide-based compositions and therapies described herein are administered to a subject at risk for cancer (e.g., precancerous, genetic risk factors, environmental risk factors, lifestyle risk factors, etc.) to prevent cancer. In some embodiments, the peptide-based compositions and therapies described herein are administered to a subject in remission from to prevent the reoccurrence of cancer and/or development of metastasis. In some embodiments, the peptide-based compositions and therapies described herein are administered to a subject suffering from cancer to kill the cancer cells, reduce tumor size, prevent metastasis, and/or to render the cancer cells susceptible to other treatments.

In some embodiments, the peptides, stapled peptide, peptide amphiphiles, and nanostructures herein find use in or with one or more immunotherapies (e.g., cell-based therapies, cancer vaccine, checkpoint inhibitors, etc.). In some embodiments, the peptide is administered to a patient's T cells (e.g., dysfunctional T cells) ex vivo and then the restored T cells are administered to the patient. In some embodiments, the peptides, stapled peptide, peptide amphiphiles, or nanostructures herein are administered to antigen specific T cells (e.g., Tregs) and the T cells are then administered to a patient with cancer, and autoimmune disease, etc.

EXPERIMENTAL

Stabilized α-Helices of FOXP3 LZ Dimerization Domain (SAH-FOXP3DD) and SAHFOXP3NFAT Peptides Experiments conducted during development of embodiments herein to design stabilized α-helices of FOXP3 Dimerization Domain (SAH-FOXP3DD). Using a combined strategy of crystal structural analysis and chemical synthesis, a series of overlapping unstapled peptides corresponding to the FOXP3 LZ homodimerization domain were constructed and analyzed for their ability to inhibit FOXP3 binding to oligonucleotide probes using electrophoretic mobility shift assays (EMSAs). A number of unstapled peptides had a dose-dependent inhibition of FOXP3ΔN: DNA binding at concentrations of ~100-200 µM. There are a number of strategies to replicate the secondary structure of α-helical motifs within proteins including disulfide bridging, lactam bridging, and hydrocarbon stapling (Schafineister et al., 2000; Galande et al., 2005; Judice et al., 1997; Leduc et al., 2003; Sia et al., 2002; herein incorporated by reference in their entireties). Hydrocarbon stapling in the form of Stabilized Alpha-Helices, or SAHs, was specifically developed to investigate and target α-helical interactions in vitro and in vivo without susceptibility to cellular degradation. Substitution/insertion of non-natural amino acids with olefin tethers at positions spanning either one (i,i+4) or two (i,i+7) turns of an α-helix followed by ruthenium catalyzed olefin metathesis crosslinks, or "staples", the inserted residues together. SAHs endow α-helical peptides with improved pharmacologic properties such as cellular penetration, protease resistance, and increased binding affinity.

Figure 1B:
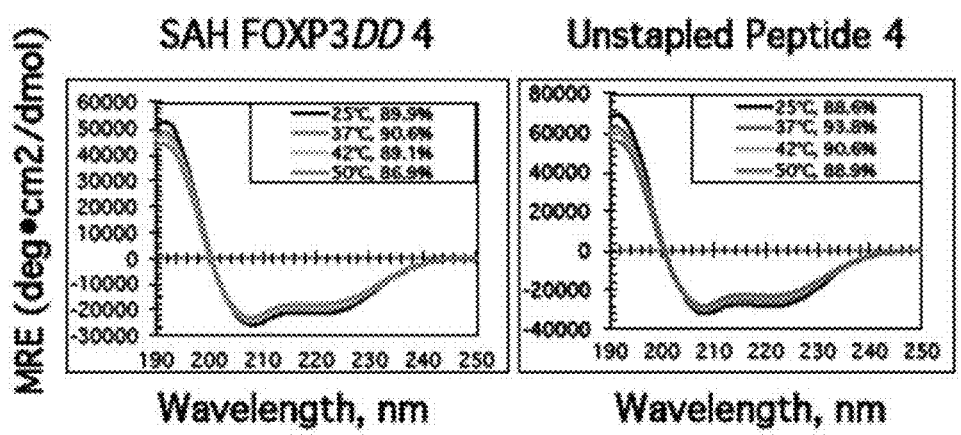
Figures 10A, 10B:
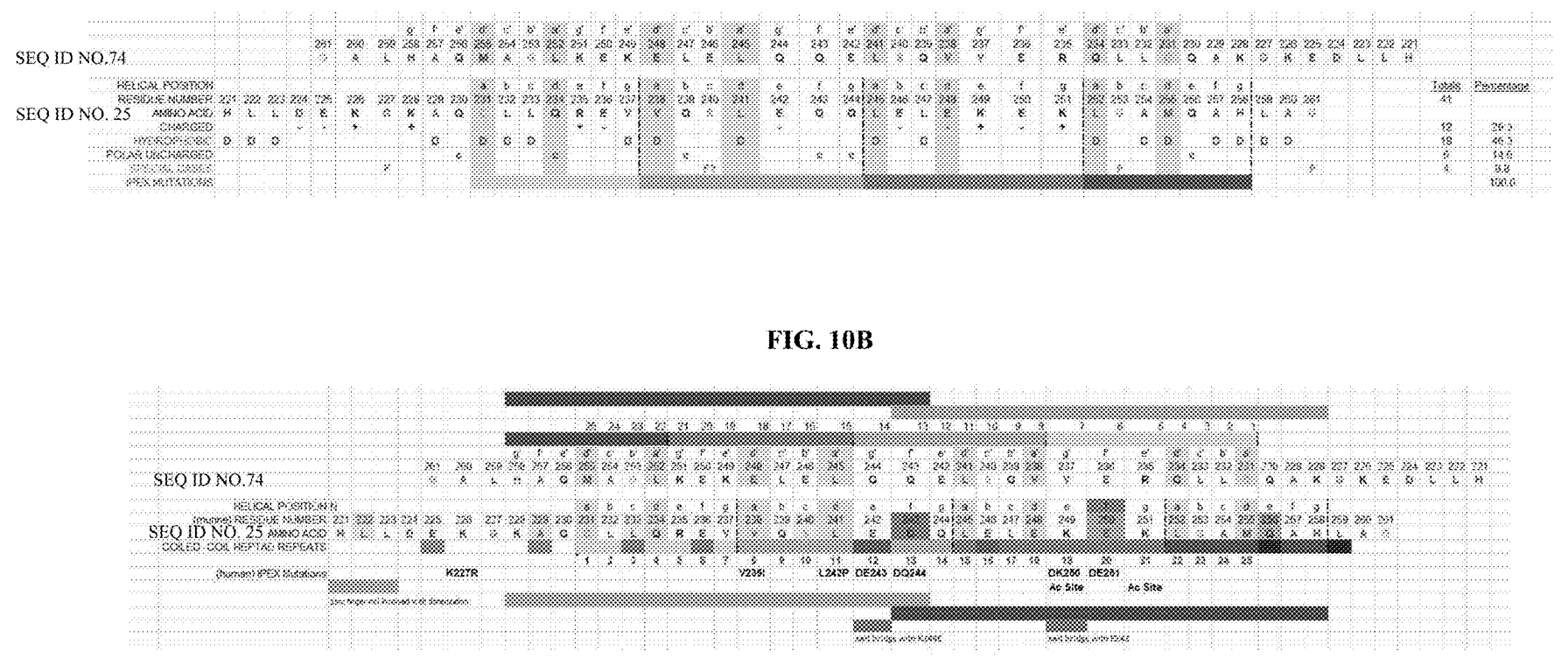

A library of hydrocarbon stapled peptides were synthesized representing these templates (SAH-FOXP3DDs) that incorporated three different hydrocarbon staple positions along the solvent-exposed face so as to avoid disruption of critical contact points between 'a' and 'd' residues of the coiled-coil. Non-natural amino acids were inserted at positions i,i+7 so that the hydrocarbon staples face away from the dimerization interface (FIG. 1A). Single i,i+7 staples, representing two turns of the α-helix have been shown to confer increased α-helicity and protease resistance in long coiled-coiled stapled peptides (Bird et al. J Clin Invest 2014; 124:2113-24; incorporated by reference in its entirety). Both native and stapled FOXP3DD peptides were α-helical in solution at a wide range of temperatures (20-50° C.) (FIG. 1B). To achieve solubility of the unstapled constructs for CD evaluation, 20% acetonitrile:water solution was used. The addition of the organic solvent may have influenced the estimated α-helical content, resulting in enhanced α-helicity of the unstapled FOXP3 peptides (Edwards et al. ACS Chem Biol 2015; 10:2149-57; incorporated by reference in its entirety). Only the stapled peptides bound recombinant FOXP3 LZ coiled-coil (LZCC) and FOXP3 lacking the N-terminal repressor domain (FOXP3ΔN) (FIG. 7). SAH-FOXP3DDs bound more avidly to LZCC than FOXP3ΔN given the lack of physical constraints leading to overall accessibility to the dimerization interface and straightforward on-off kinetics of the LZCC dimer. The unstapled version of each peptide showed no binding to FOXP3, confirming the importance of reinforcement of the α-helical structure (FIG. 7. Despite the LZCC domain being geographically distant from the FKH region and not responsible for direct DNA binding, 4 of 6 SAH-FOXP3DDs showed dose-dependent inhibition of FOXP3ΔN:DNA binding (FIG. 1D and FIG. 10). The relative potency of the SAH-FOXP3DDs correlated with binding affinity to LZCC and FOXP3ΔN, as determined by a fluorescence polarization assay (FPA), further confirming specificity of action. FITC-conjugated SAH-FOXP3DDs were screened against the LZCC portion of FOXP3 (FOXP3 S189-K276) and FOXP3ΔN and KDs (dissociation rates) determined by FPA.

To exclude non-specific binding to the negatively charged DNA probe, a liability of using charged peptides in EMSAs, SAH-FOXP3DDs were incubated with each probe at up to twice the highest concentration used. No binding was observed at 25 μM and only minimal binding at 50 μM with SAH-FOXP3DD3,4,10. Next, SAH-FOXP3DDs were incubated with recombinant NFAT (NFAT DBDW400-W680) and the Il-2 reporter oligonucleotide ARRE2 element as a further test of specificity. SAH-FOXP3DDs were unable to inhibit NFAT:DNA binding, further validating on-target specificity of the peptides. Based on these results, SAH-FOXP3DD 2 and 10 were advanced to functional testing. A double-stapled SAH-FOXP3DD10 peptide was synthesized and found the ability to inhibit Treg-mediated suppression is greater than the parent compound and a point mutant control ((SAH-FOXP3-DD(K252D)).

Live cell confocal microscopy of FITC-SAH-FOXP3DD-treated HeLa cells confirmed intracellular uptake within the cytosol and nucleus of both stapled peptides. To rule out the possibility that SAH-FOXP3DDs achieved cellular penetrance nonspecifically, lactate dehydrogenase (LDH) release assays were performed, a robust screening tool for identifying membrane-disruptive, and thus cytotoxic, peptides. There was no LDH release from primary mouse thymocytes, Jurkat T cells, or HeLa cells at a wide dose range, indicating that SAH-FOXP3DDs are not overtly toxic to cells. Additionally, there was no increase in apoptosis (via annexin V/PI staining) of treated Tregs confirming their persistence following SAH-FOXP3DD treatment. Strikingly, naïve Tregs from C57BL/6 FOXP3IRES-GFP pre-treated for 2 hours with SAH-FOXP3DD10 were unable to inhibit the proliferation of syngeneic FOXP3neg CD4+ T cells (Tcons) following stimulation, while control-treated Tregs retained their suppressive activity—as measured by Tcon proliferation as confirmed by flow cytometry. The degree of Treg inhibition was lower, but still present, when in vitro expanded Tregs were used. Flow cytometric evaluation measured no difference in the amount of Tregs in treated vs. untreated samples again indicating no increased cell death following treatment with SAH-FOXP3DDs. These results indicate that the SAH-FOXP3DDs are able to inhibit the immunosuppressive function of Tregs without affecting the ability of Tcons to undergo proliferation.

Figure 2A:
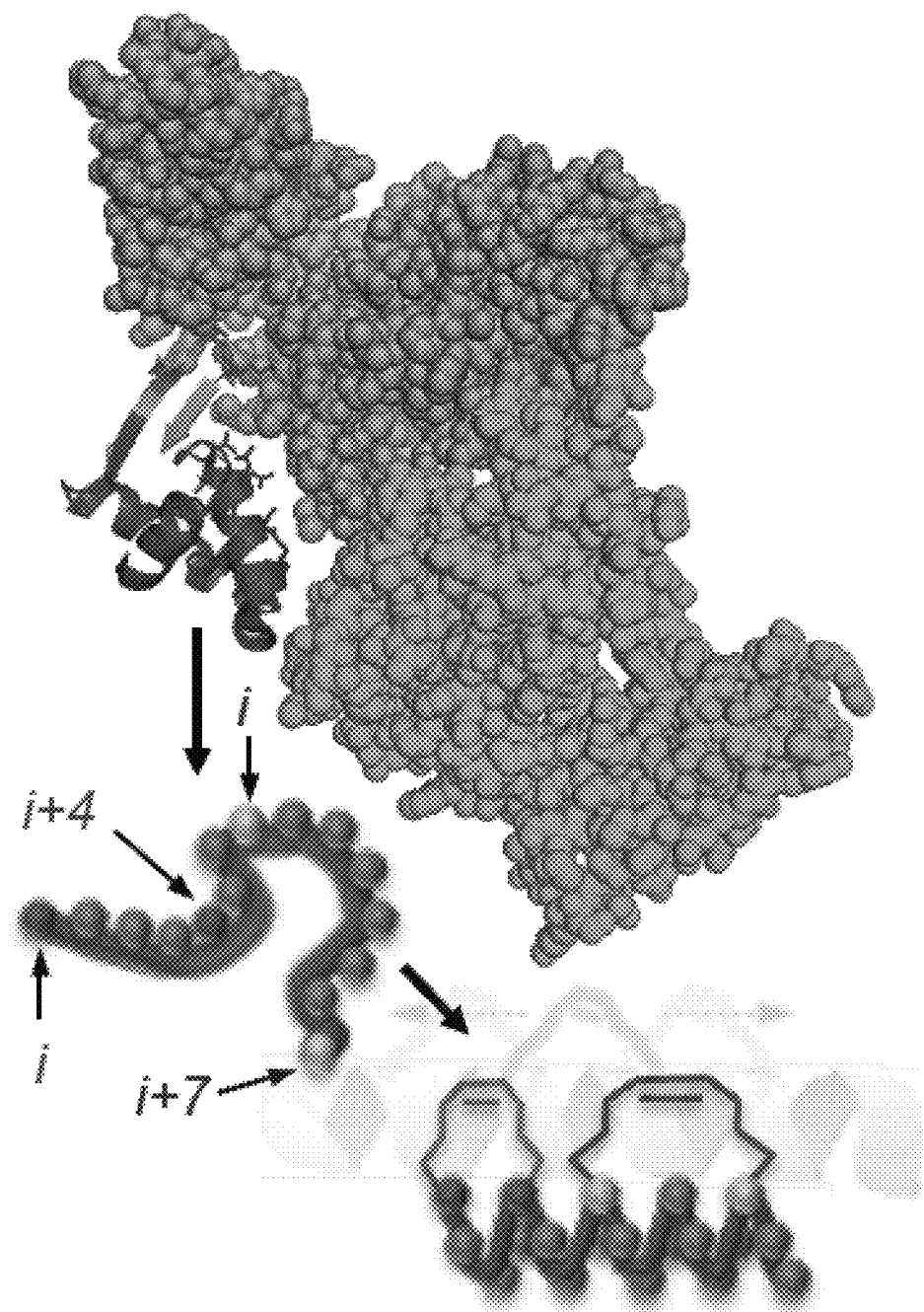
FIG. 2A-E. Design, biochemical characterization, and functional testing of SAH-FOXP3NFATs. (A) Design strategy for SAHs targeting the FOXP3:NFAT1 dimerization interface. (B) CD showing that i(i+4) and i(i+7) stapled SAH-FOXP3NFATs and their point mutant controls are helical in solution. (C) Increasing expression of FOXP3 inhibits NFAT:AP1-mediated transcription as measured by a dose dependent decrease in luciferase activity. (C&D) Dose dependent inhibition of FOXP3-mediated NFAT repression with 2.5 ng (D) and 10 ng (E) FOXP3 DNA. Point mutant controls have no effect thus confirming specificity of action.
Figure 2B:
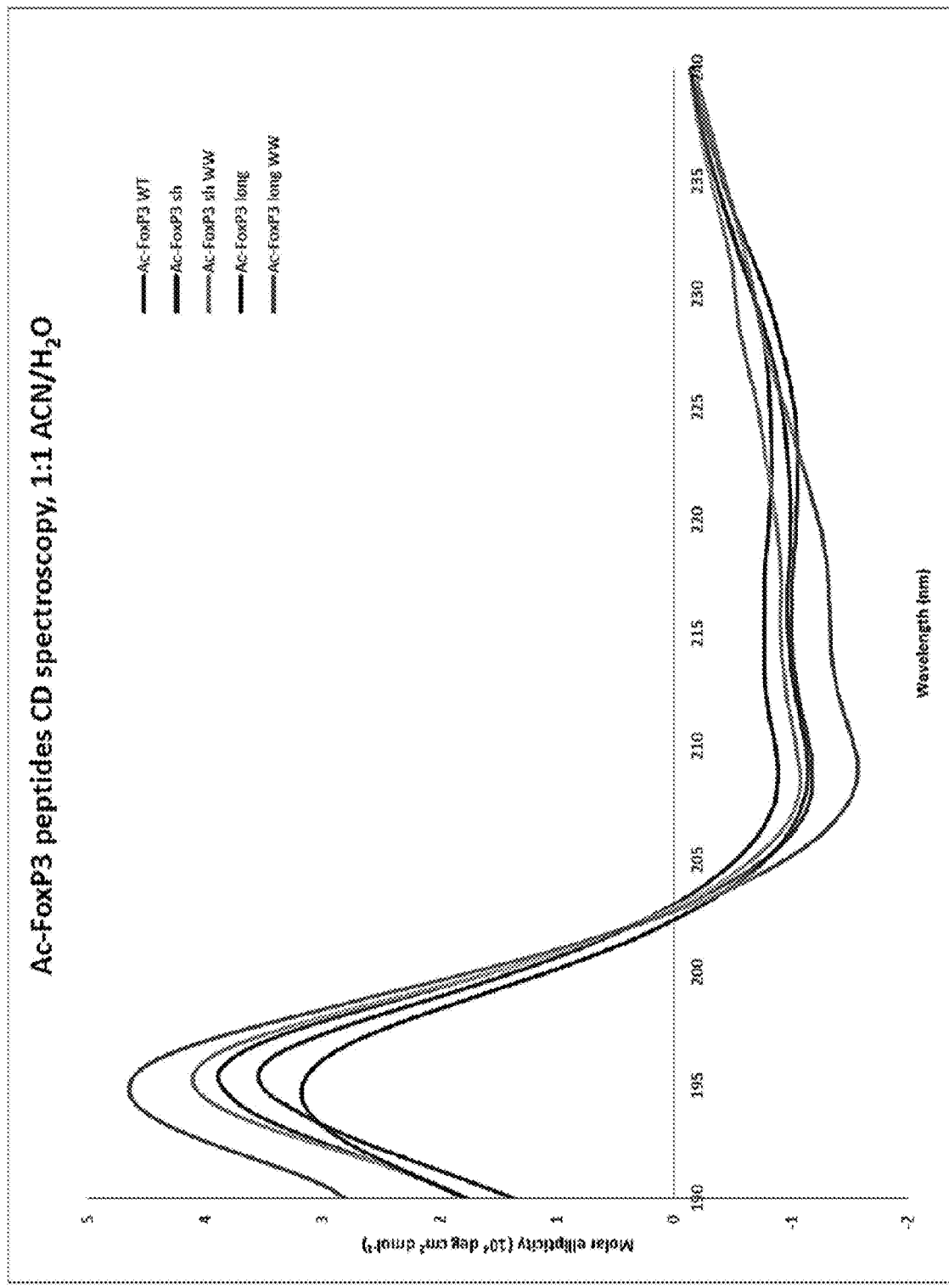
Figure 2C:
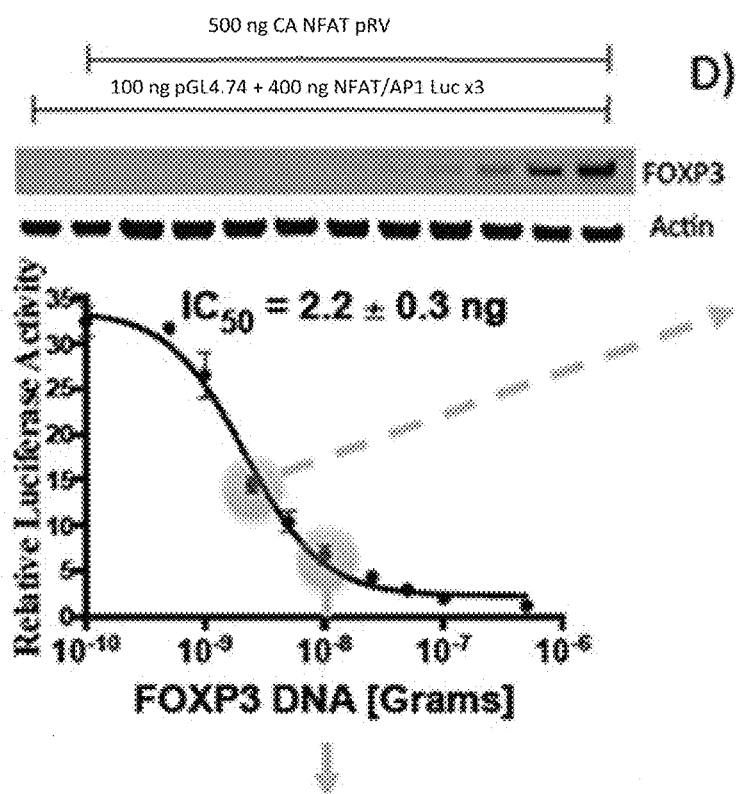
Figure 2D:
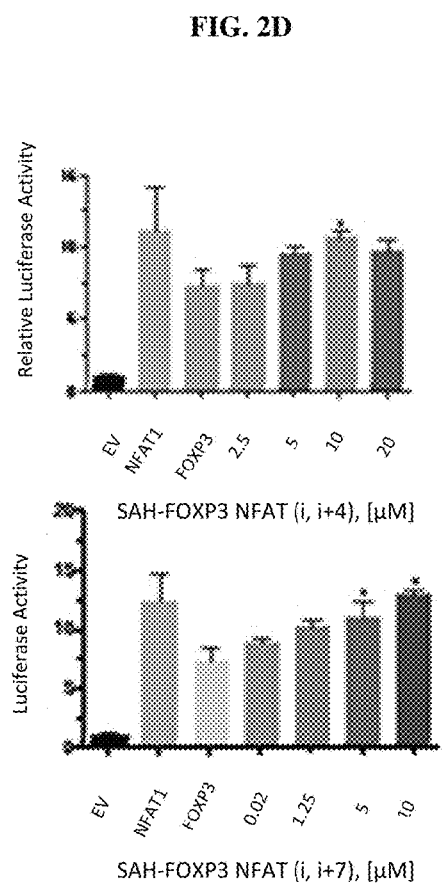
Figure 2E:
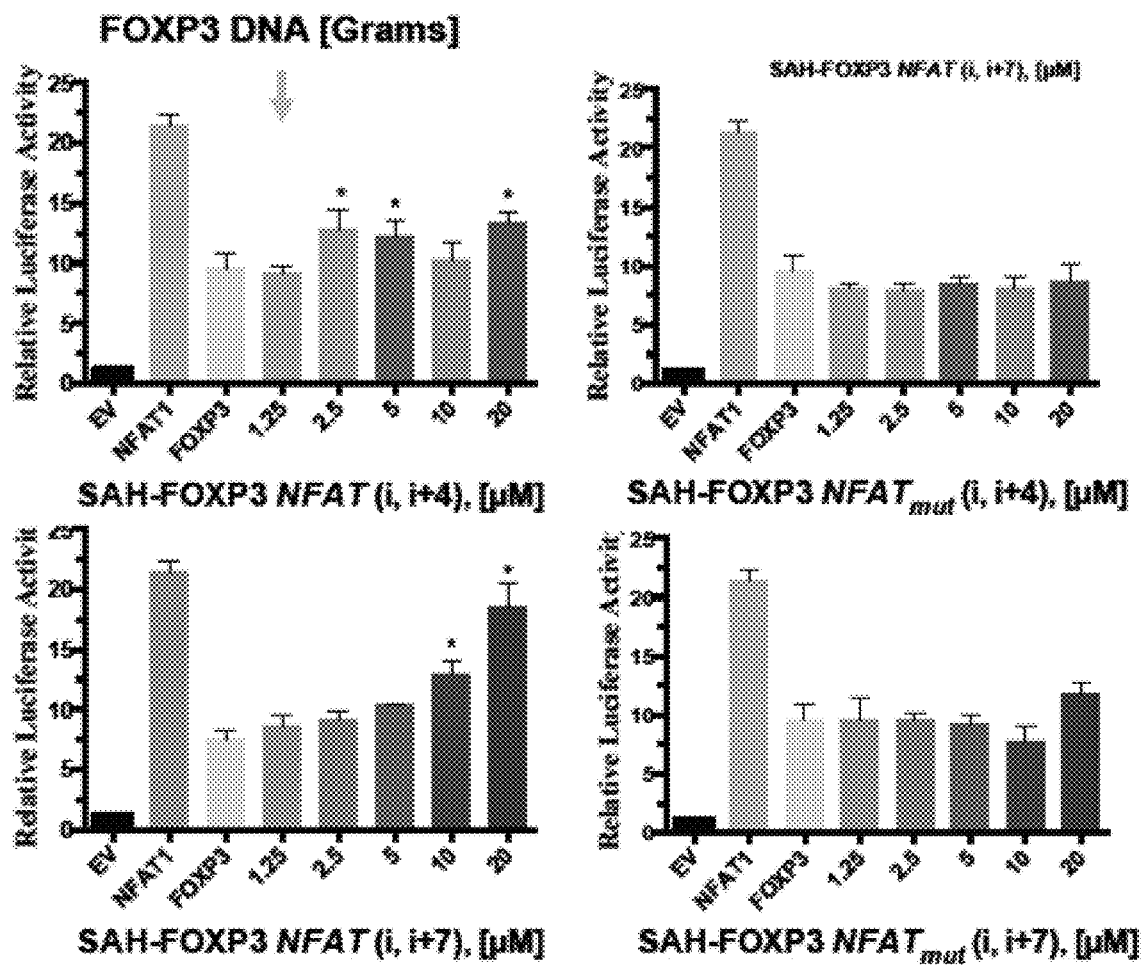
Figure 5A:
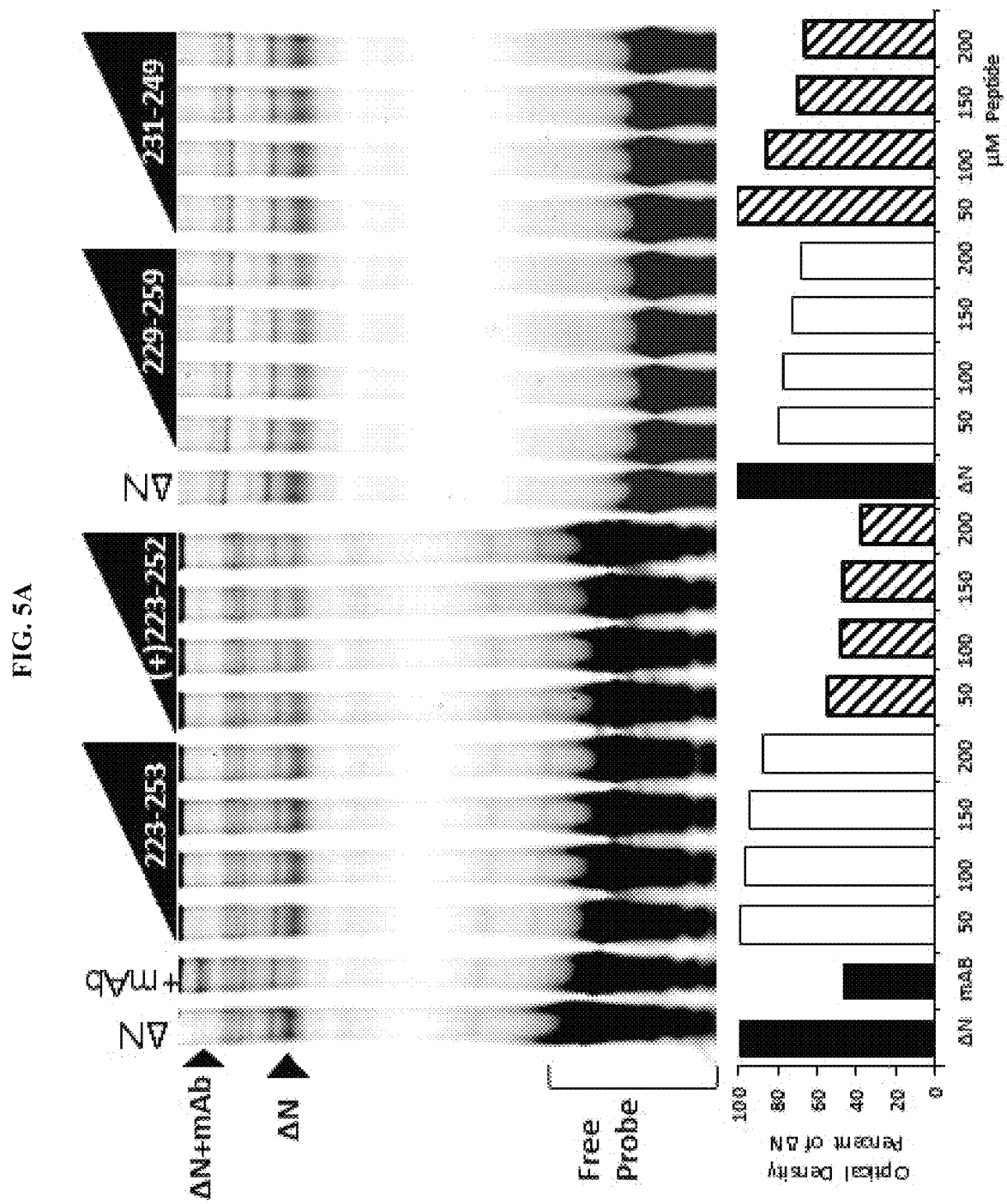
Figure 5B:
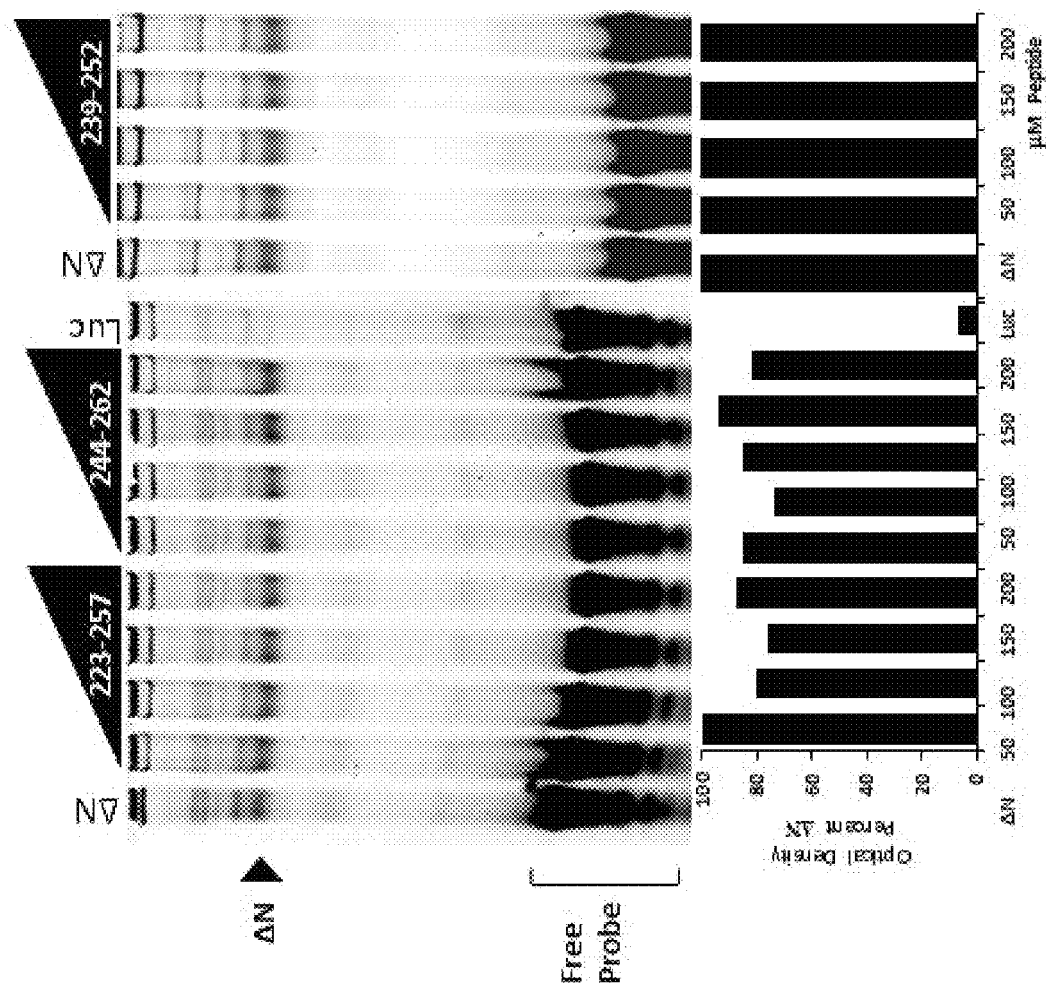
Figure 6:
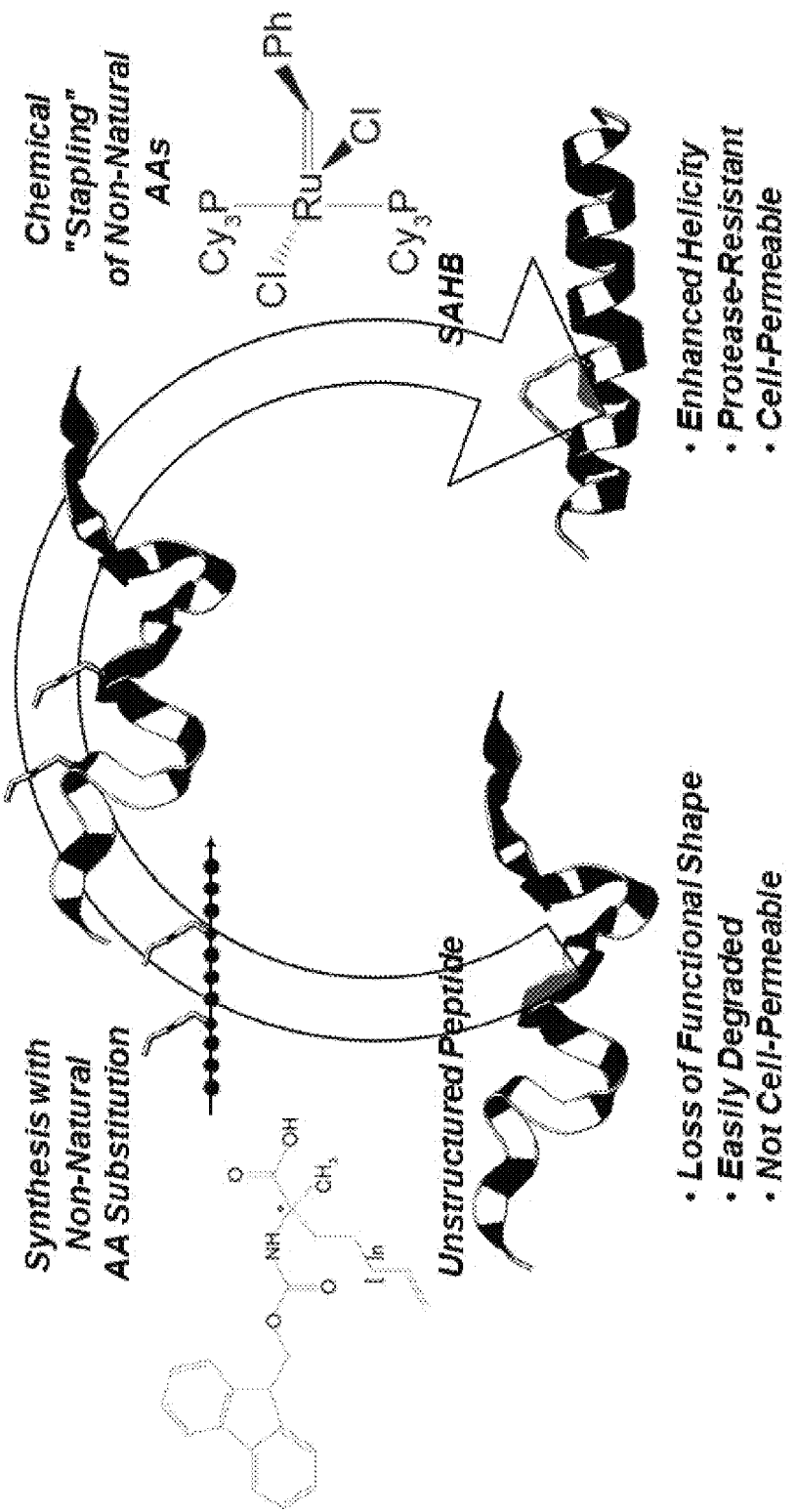
FIG. 6. Schematic depicting the method and advantages of peptide stapling.
Figure 7A:
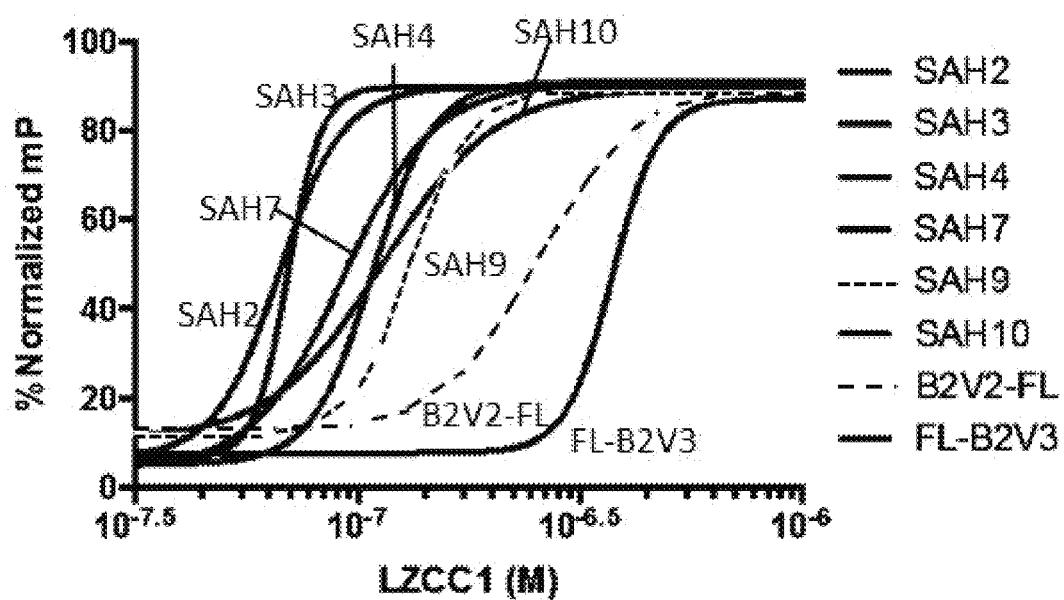
FIG. 7A-D. Fluorescence polarization assay to determine SAH-FOXP3 binding to recombinant FOXP3 leucine zipper coiled-coiled (LZCC) domain. (A) Serially diluted recombinant LZCC was incubated with 50 nM FITC-peptide in 1×PBS pH 8 for 5-10 mins and then fluorescent polarization was measured using a SpectraMax spectrometer. Unstapled native peptides (B2V2 and B2V3) bind with much lower affinity than all stapled peptides (SAHs), which have Kd values in the low nM range. SAH2 and SAH3, which have identical amino acid sequences but different staple positions, have similar binding affinities. (B—C) Serially diluted recombinant LZCC (A) or FOXP3 ΔN (B) was incubated with 50 nM FITC-peptide in 1×PBS pH 8 for 5-10 mins followed by fluorescent polarization measurement using a SpectraMax spectrometer. (D) Shift of composite binding curves indicate increased affinity for the leucine zipper coiled-coiled (LZCC) domain and FOXP3ΔN.
Figure 7B:
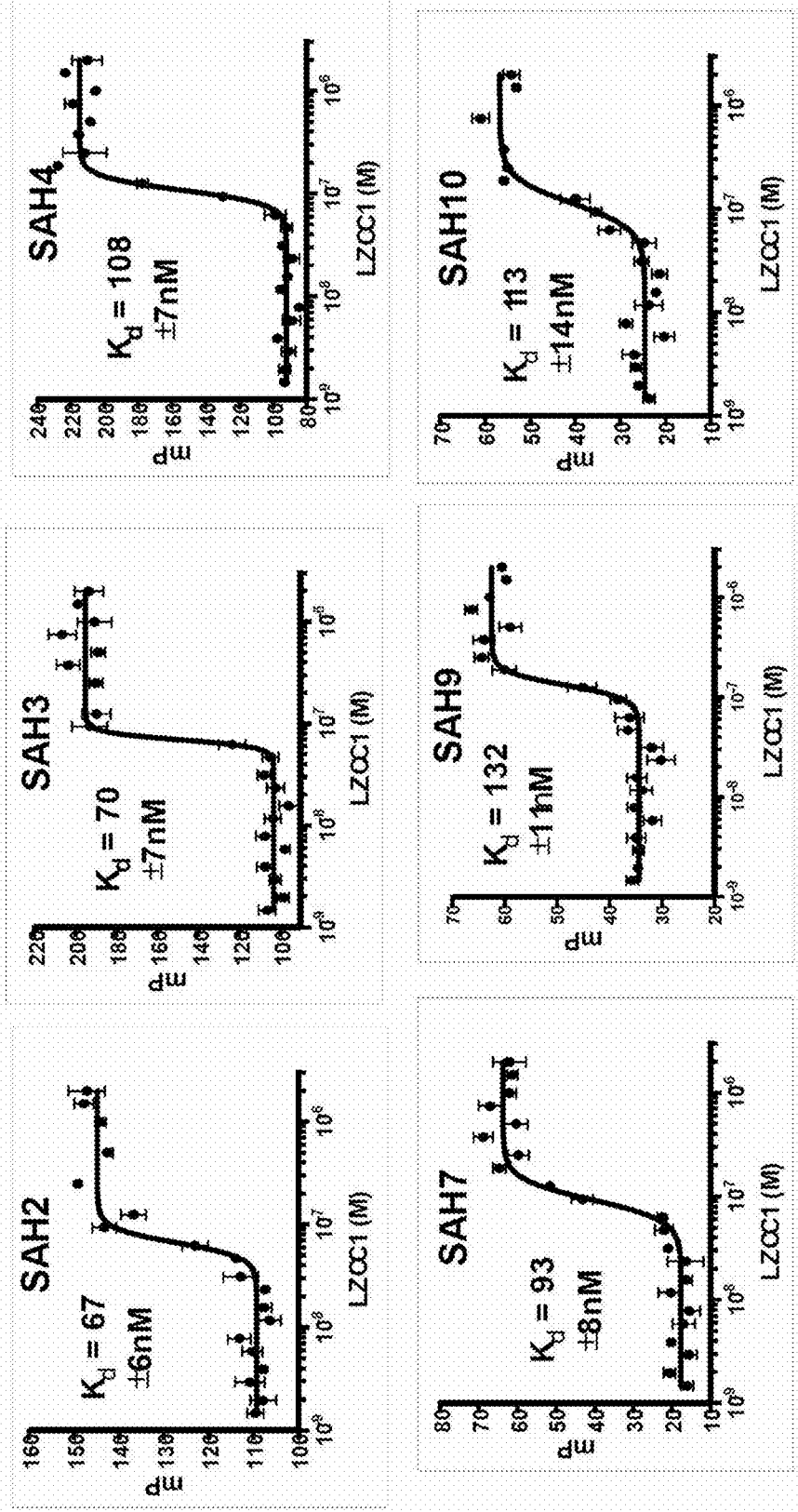
Figure 7C:
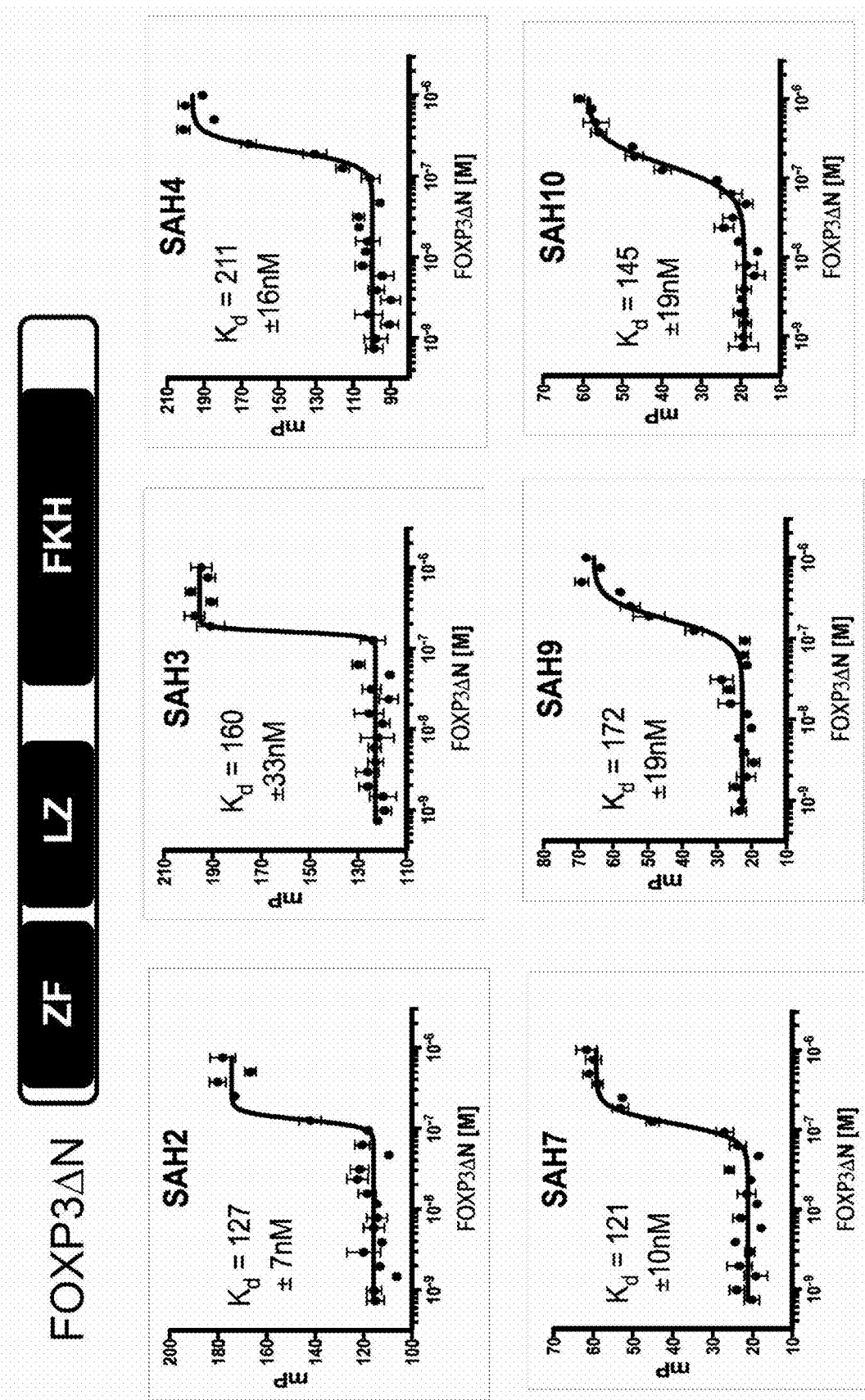
Figure 7D:
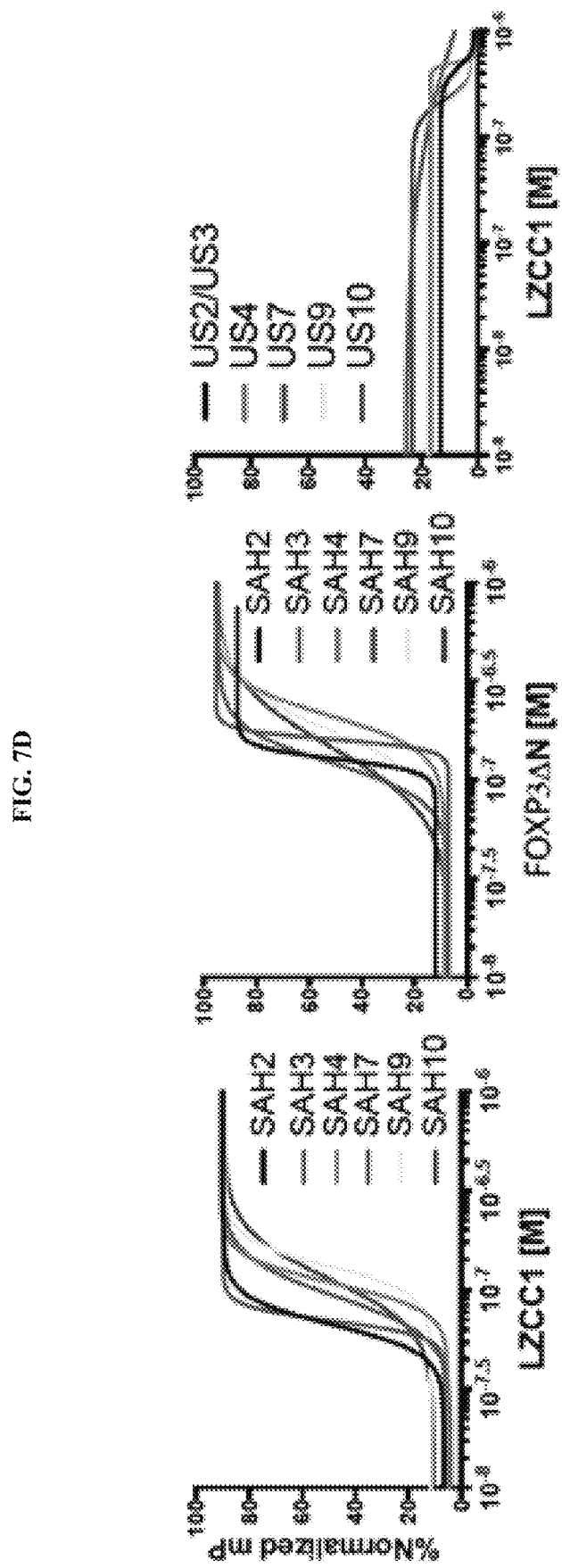
Figure 8A:
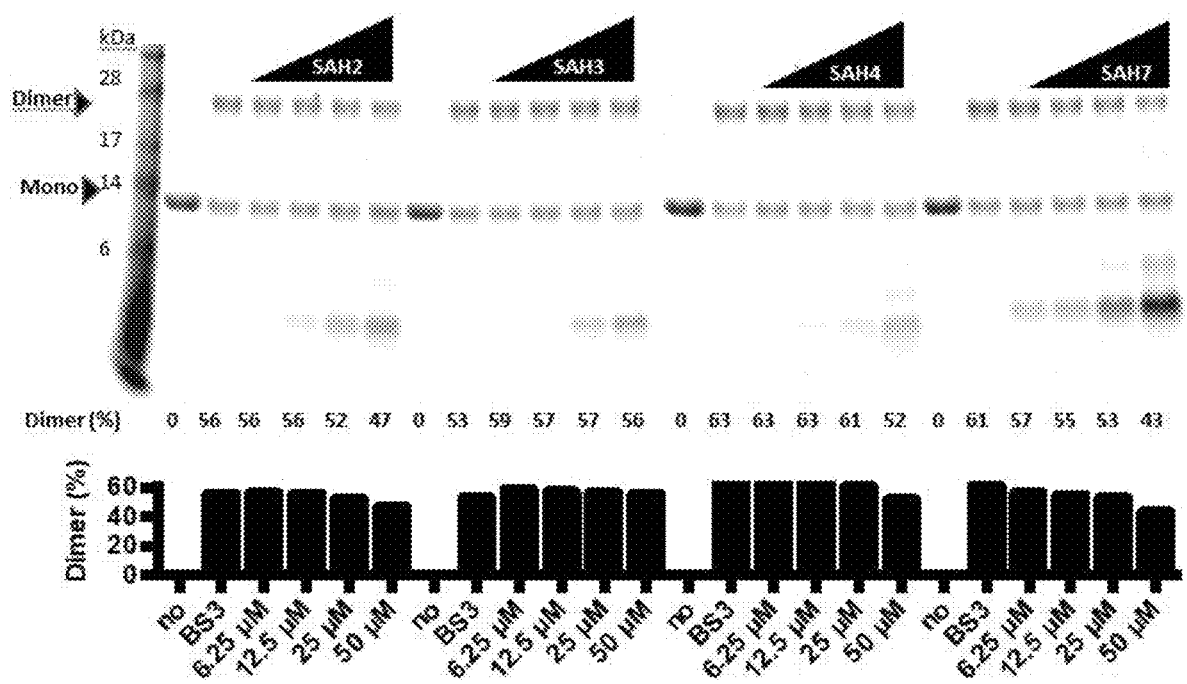
FIG. 8A-B. Chemical Crosslinking. SAH-FOXP3 peptides incubated with recombinant LZCC protein for 2 hours at room temperature in 1×PBS. 1 mM of the chemical crosslinker BS3 or DSS was added to each tube for 30 mins at room temperature. Samples were denatured and then separated by electrophoresis on a NuPage SDS 10/a Bis-Tris gel following the manufacturer's protocol (Invitrogen). Protein was imaged after staining the gel with coomassie on the Odyssey Imager. SAH7 and SAH9 produce a modest decrease in the amount of dimerized FOXP3 protein, indicating that these SAHs are able to dissociate homodimerized FOXP3. In some cases, SAH peptide crosslinks with monomeric FOXP3 alone FIG. 9A-C. Electrophoretic mobility shift assays (EMSA). (A) SAHs block FOXP3 binding to cognate DNA; a comparison of stapled and unstapled peptides. EMSA with FOXP3ΔN incubated with increasing concentrations of different SAH-FOXP3 are shown. Labeled probe containing consensus sequence (A'GT25) for FOXP3 was incubated at room temperature for 15 mins with recombinant FOXP3ΔN and increasing concentrations of SAH peptide [3 µM to 25 µM]. The last lane in each set is 25 µM of peptide alone with DNA probe. (B) SAH-FOXP3DD peptides are specific for the transcription factor FOXP3 and do not disrupt the binding of another transcription factor NFAT to its cognate DNA. IRDye700 labeled probe containing consensus sequence for NFAT was incubated at room temperature for 15 mins with 100 pmole recombinant NFAT-DBD and peptide or DMSO using the Odyssey Infrared EMSA kit per manufacturer's protocol (Li-Cor). Reactions were then separated by electrophoresis on a 10% TBE gel and imaged using an Odyssey Imager (Li-Cor). (C) The use of two alpha-helical stabilizing staples leads to more effective FOXP3:DNA disruption than single stapled SAH-FOXP3DD peptides.
Figure 8B:
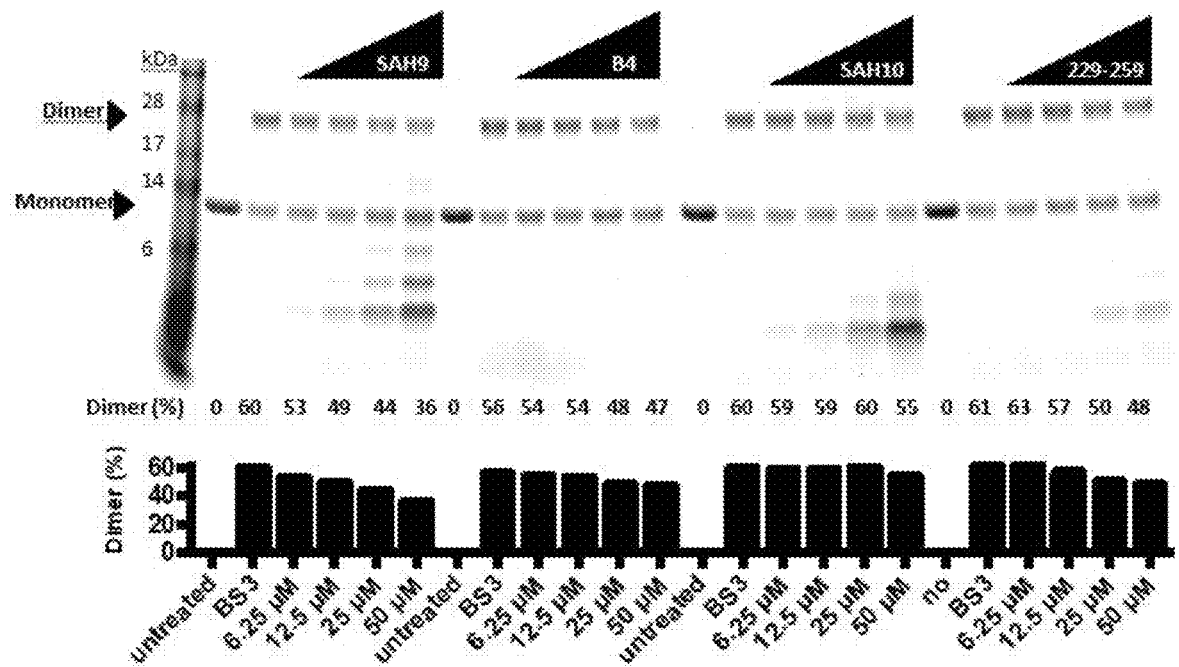
Figure 9A:
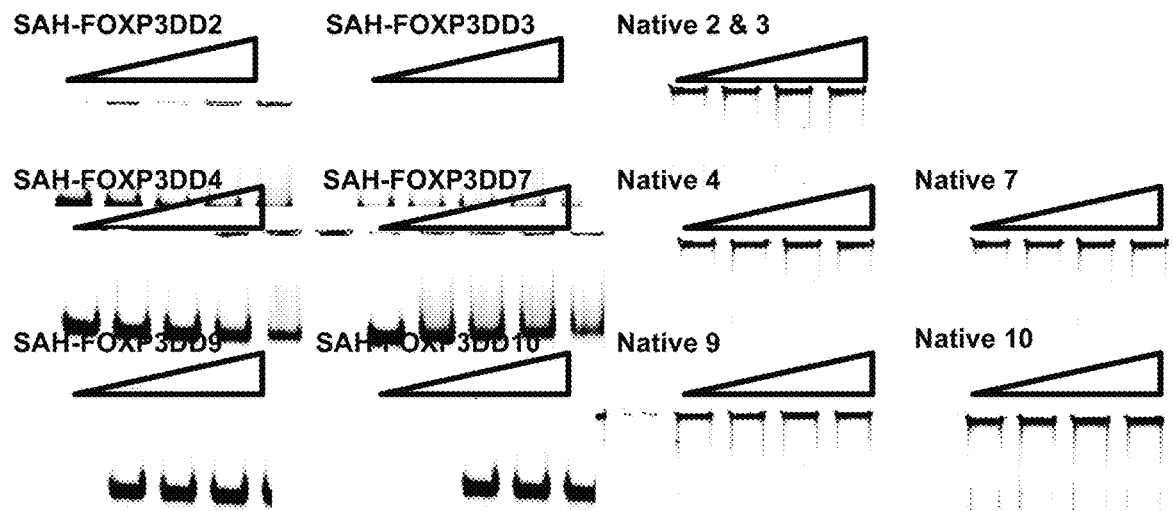
Figure 9B:
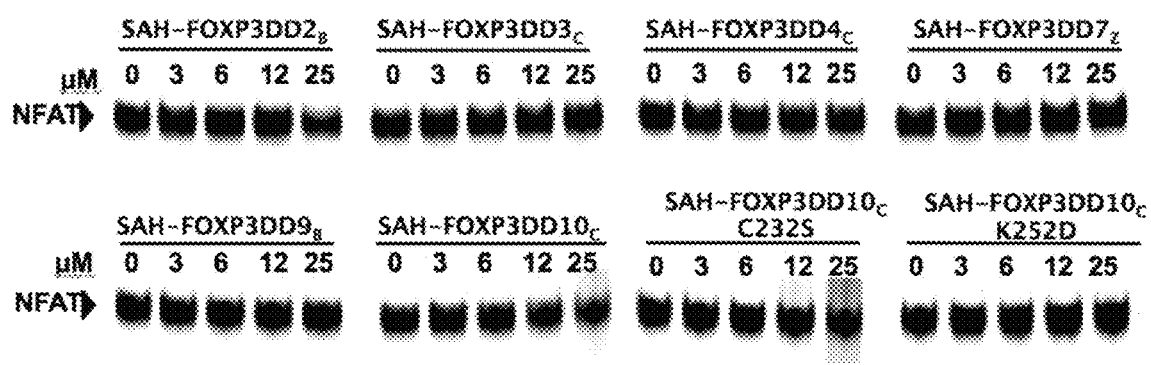
Figure 9C:
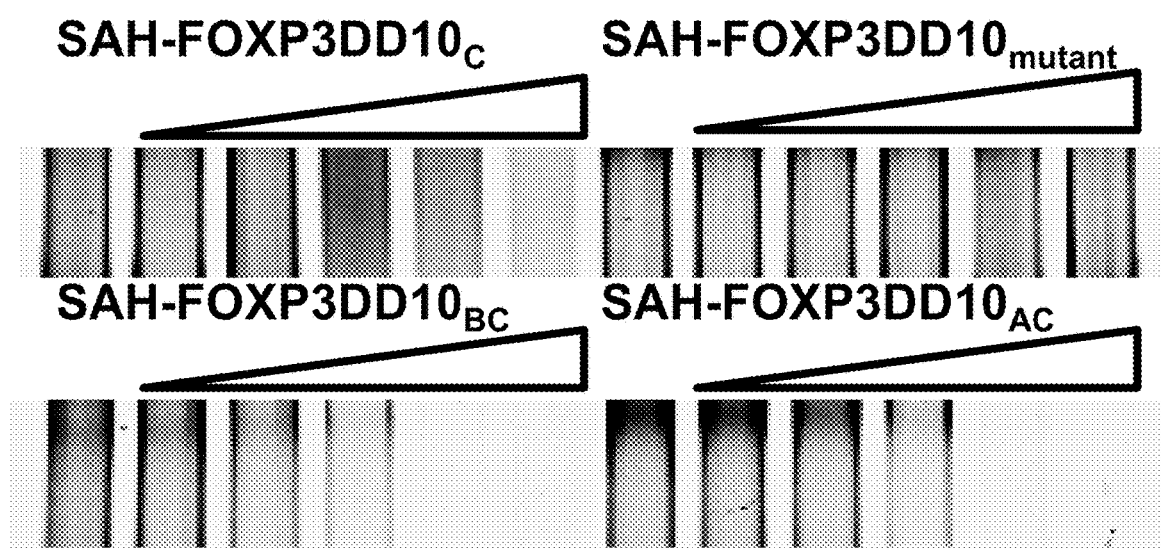
Figure 11A:
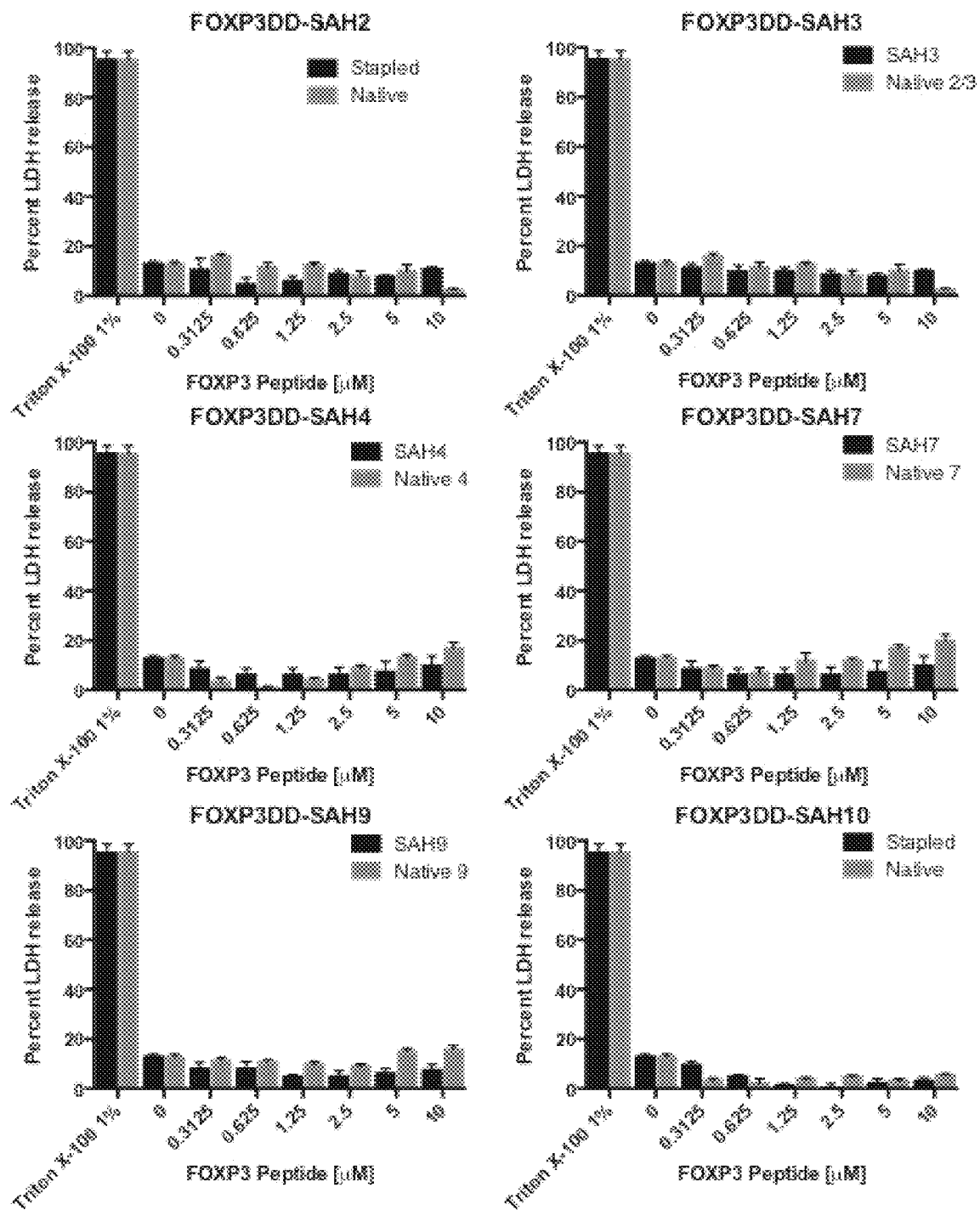
FIG. 11A-B. Peptides do not cause nonspecific lysing of cells, as measured through apoptosis assays. (A) Thymocytes (1000 per µL) freshly isolated from healthy wild type mice were incubated with increasing concentrations of peptides, DMSO or 1% Triton X-100 in 200 µL OptiMEM for 4 hours. Cells were spun and media extracted for colorimetric analysis using an LDH Cytotoxicity detection kit following the manufacturer's protocol (Roche). (B) Thymocytes (1000 per µL) freshly isolated from healthy wild type mice were incubated with increasing concentrations of peptides, DMSO or staurosporine in 200 µL OptiMEM for 4 hours. Cells were then stained with Annexin V-APC and propidium iodide from an Apoptosis Detection kit following the manufacturer's protocol (eBiosciences) before analysis using flow cytometry FIG. 12A-B. SAH-FOXP3DD peptides are able to alter cellular expression (protein and mRNA) of FOXP3 target genes. Conventional T cells (CD4+ CD25−) and regulatory T cells (CD25+ GFP+) were isolated from CD4+ cells enriched from spleen and draining lymph nodes of FOXP3-IRES-GFP. Tregs were treated at 1000 cells per µL with peptides in OptiMem for 2 hours before being quenched with completed advanced DMEM and then stimulated with CD3/CD28 beads. Gene expression was determined using qRT-PCR 4 hours after stimulation. Membrane (live cell) or internal (fixed cell) expression of proteins was determined using flow cytometry 16 hrs after stimulation.
Figure 11B:
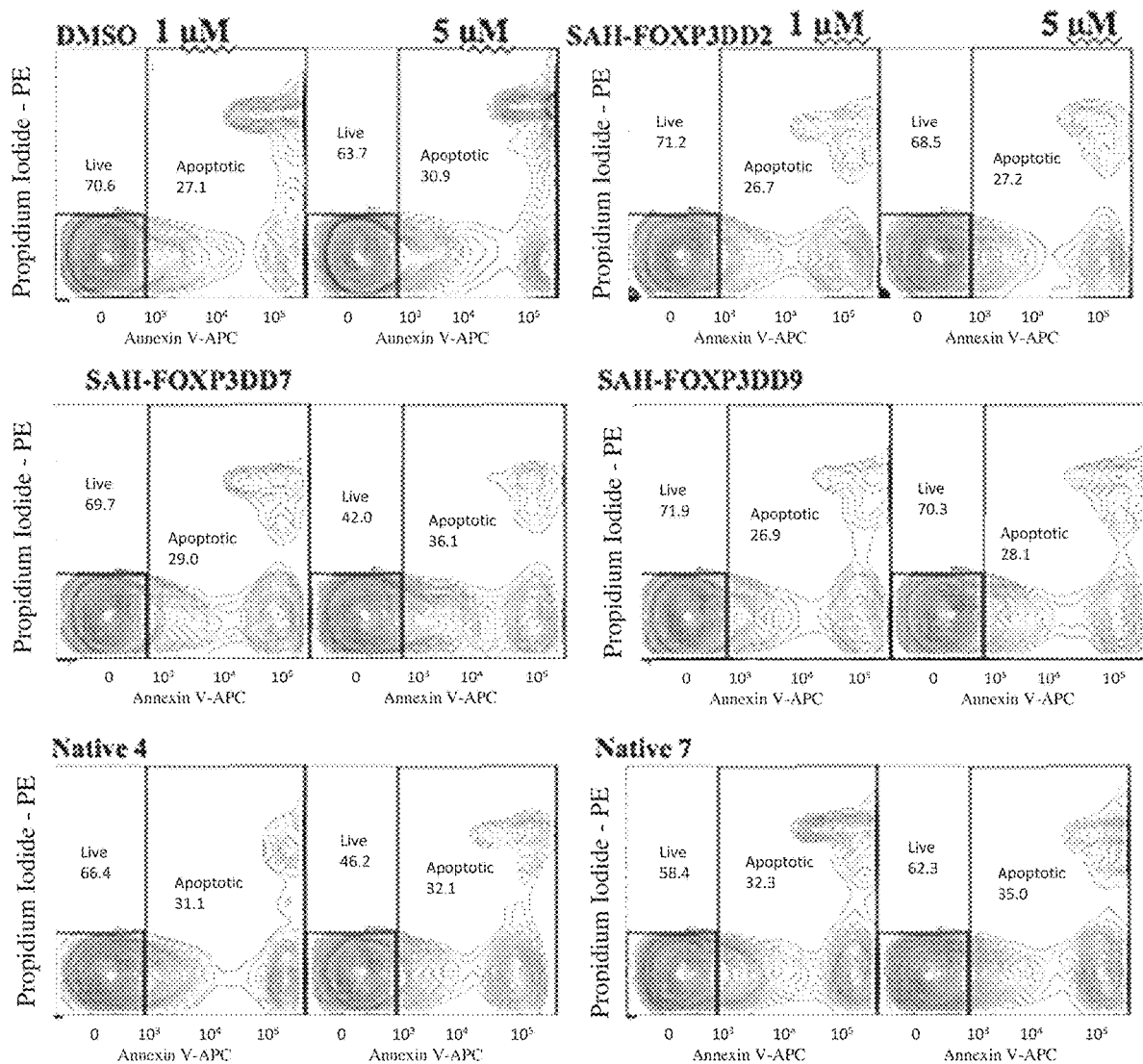
Figure 11B:
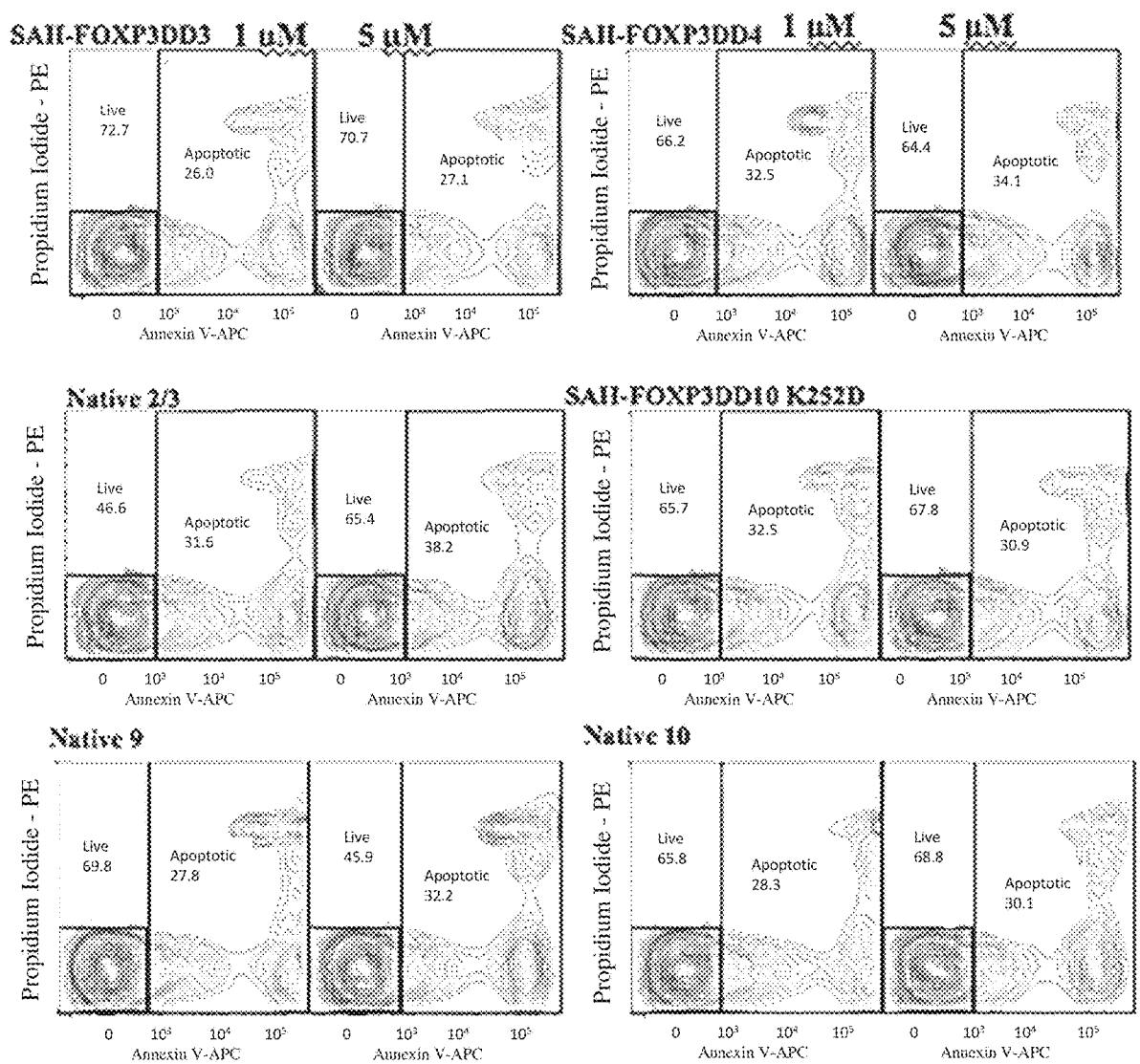
Figure 12:
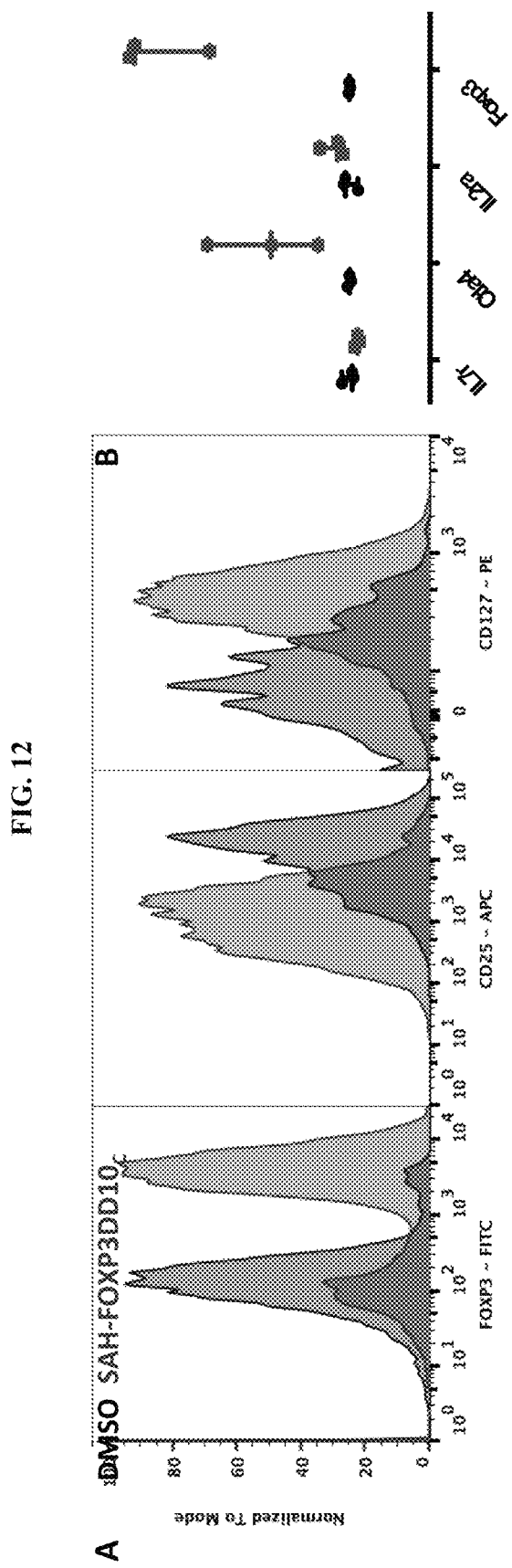
Figure 13:
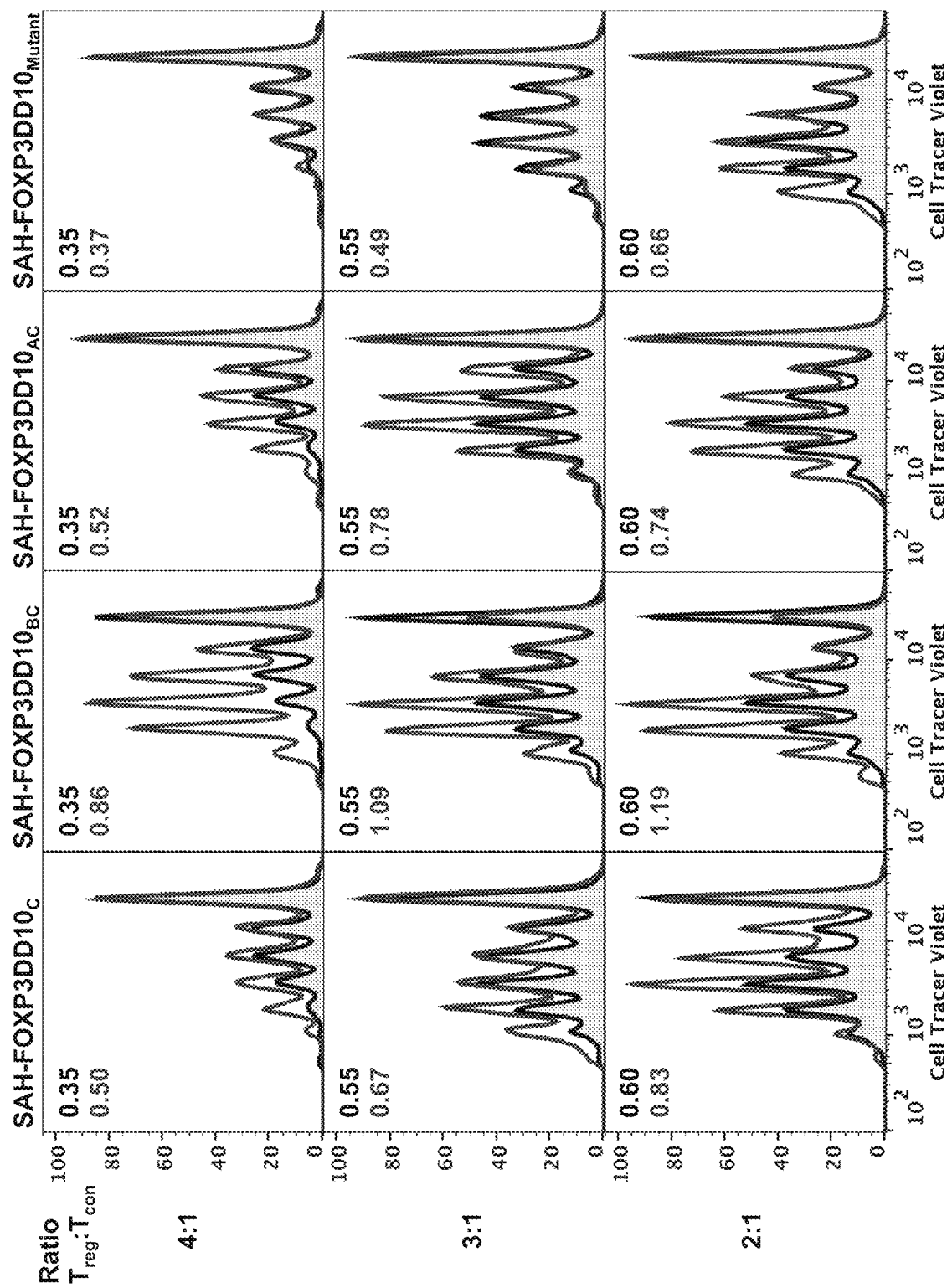
FIG. 13. Blocking of FOXP3 dimerization by SAH-FOXP3DD peptides reduces the suppressive function of regulatory T cells. The double stapled SAH-FOXP3DD peptides exhibit better inhibition, while are point mutant control has no effect. Conventional T cells (CD4$^+$ CD25$^−$) were stained with Cell Tracer Violet (1 uL to 10 mL) in warm 1×PBS for 20 minutes at 37 C. Dye was quenched with media and cells spun and suspended in fresh complete advanced DMEM. Tregs were treated at 1000 cells per µL in OptiMEM with 5 µM of peptides for 4 hours before being serial diluted and added to CTV labeled Tcons in indicated ratios. Cells were stimulated with 1:1 Tcon:Bead ratio of CD3/CD28 beads for 3 days before flow cytometric analysis.

Experiments were conducted during development of embodiments herein to design stabilized α-helices of the FOXP3:NFAT1 interface (SAH-FOXP3NFAT). Using a similar approach as above, stapled peptides based on a FOXP3 α-helix, which is responsible for NFAT1 binding (FIG. 2A), were designed. Non-natural amino acids were inserted in either the i,i+4 (SAHFOXP3NFAT(i,i+4)) or i,i+7(SAHFOXP3NFAT(i,i+7)) positions. Hydrocarbon stapling of the FOXP3NFAT peptides and point mutants similarly stabilizes their helicity (FIG. 2B). The peptides were tested for inhibition of FOXP3:NFAT1 binding. Co-expression of increasing amounts of FOXP3 DNA with constitutively active NFAT1 dose dependently represses NFAT1:AP1 transcriptional activity at an IL-2 promoter ARRE2 luciferase reporter element in transfected human embryonic kidney (HEK) cells (FIG. 2C). Treating cells with both SAH-FOXP3NFAT(i,i+4) and SAH-FOXP3NFAT(i,i+7) inhibited this FOXP3-mediated repression when either 2.5 ng or 10 ng FOXP3 DNA were added to the system (FIGS. 2D & E). Confirming specificity of action, neither point mutant control SAH had any effect (FIG. 2E). FOXP3NFAT (I,i+7) dose-responsively inhibited FOXP3:NFAT association when both doses of FOXP3 were used. However, FOXP3NFAT(i,i+4) fully inhibited 'low dose' FOXP3 but was less able to inhibit FOXP3-mediated repression when there was an excess of FOXP3 present. Possibilities include differences in cellular penetrance, binding efficiency, or intracellular trafficking between the two SAHs.

Tregs and Tcons were stimulated from C57BL/6 FOXP3IRES-GFP with IL-2 and CD3/CD28 microbeads for seven days and treated them with a dose titration of SAH-FOXP3DD10, or unstapled control, and measured membrane expression of CD127 (IL7Ra). Tregs and Tcons normally downregulate CD127 mRNA expression following seven days of stimulation. A dose dependent increase in CD127 was measured in Tregs treated with SAH-FOXP3DD10 compared to unstapled peptide and control-treated Tcons, indicating that even in an activated state, SAH-FOXP3DDs induce measurable changes in protein expression. Confirming that FACS measurement of CD127 upregulation was not due to non-specific cellular membrane SAH binding, a dose dependent decrease was measured in two other T cell markers, CD44 and CD69, both of which are normally upregulated in activated effector Tregs. These results demonstrate on-target physiologic changes induced by SAH-FOXPDD-mediated FOXP3 inhibition. SAH-FOXP3DD treatment also increased FOXP3 expression in naïve Tregs in the presence of IL-2 and CD3/CD28 microbeads. Quantitative PCR (qPCR) from these same cells treated with SAH-FOXP3DD10 found a correlative increase in FOXP3 and IL-2 mRNA expression supporting flow cytometric results.

Peptide Amphiphile Delivery of FOXP3 Peptides

A peptide amphiphile (PA) delivery mechanism solubilizes and delivers the peptides herein into cells in high concentrations. Using the crystal structure of both the FOXP3 coiled-coil dimerization and the FOXP3:NFAT1 interaction domains, SAH-FOXP3DD and SAH-FOXP3NFAT peptides were designed by investigating alternate staple positions along the length of the helix. Staple scanning mutagenesis optimized staple geography (e.g. positions b, c, e, f and g on the coiled-coil helix with respect to SAH-FOXP3DDs) while also optimizing the position of the staple to best mimic natural target protein binding (e.g. positions facing away from the NFAT1 internal hydrophobic core with respect to SAH-FOXP3NFATs). Additional SAHs were generated using solid phase Fmoc chemistry and ruthenium-catalyzed olefin metathesis, followed by peptide deprotection and cleavage, purification by reverse phase high performance liquid chromatography and mass spectroscopy (LC/MS) as previously described. A benefit of staple scanning is that a wealth of structure-activity relationships emerged allowing identification of the most active constructs and negative control compounds to be used in further studies. The i,i+7 staple position was utilized, as this has shown benefit over the i,i+4 staple in stabilizing long α-helices. Stapled peptides designed after the entire 41 a.a. FOXP3 leucine zipper coiled-coil domain show the greatest activity in solution and therefore bringing this template forward in future studies (FIG. 1). Given the lengthy peptide template of the FOXP3 coiled-coil, insertion of 2, i,i+7 staples each spanning 2 turns of the α-helix were examined. This strategy further enhanced secondary structure, protease resistance, and biological activity in stapled helical peptides. Experimental results indicate that helical structure is critical for binding, modification greatly enhanced the biologic activity of SAH-FOXP3DDs.

In some embodiments, cathepsin-cleavable linker sequences (Valine-Citruline) are added to either the N- or C-terminus of the SAHs and link them to the DSPE-PEG2000 hydrophobic group (Missirlis et al. PloS one 2013; 8:e54611; incorporated by reference in its entirety). Single-tail amphiphiles are made using standard Fmoc-mediated solid phase peptide synthesis. C- or N-terminal linkage to the PEG spacer were followed by addition of the hydrophobic double tail to promote round micelle formation, increase cellular uptake, and ensure initial micelle anchoring to the plasma membrane. Cleavage of the cathepsin linker occurs C-terminally to the citruline. Thereby, those PAs with C-terminally linked lipid tails contained the residual VC amino acids that may decrease affinity to either FOXP3 or NFAT1 (FIG. 3A).

In some embodiments, insertion of PABC (pamidobenzylocycarbonyl) linker between the prodrug peptides and the cathepsin spacer allows for improved enzymatic cleavage and robust intracellular accumulation of peptide (FIG. 3B). In some embodiments, PAs are constructed using unstapled α-helical peptides. The peptide is tagged with (FITC) and lipid tails (Rhodamine) with fluorophores in an effort to measure intracellular trafficking of both parts of the PA over time (FIG. 3). A striking accumulation of peptide and lipid tails in cells treated with the cathepsin-PABC laden PAs was observed. In contrast, there was very little accumulation in cells treated with PAs lacking the cathepsin cleavage site indicating endosomal recycling to the plasma membrane and subsequent PA release (Missirlis et al. Biochemistry 2009; 48:3304-14; Missirlis et al. PloS one 2013; 8:e54611; incorporated by reference in their entireties).

A similar strategy is employed to optimize PAs laden with either SAH-FOXP3DD or SAH-FOXPNFAT. Exquisite organelle trafficking is measured using the Leica ground state depletion/total internal reflection fluorescence (GSD/TIRF) super-resolution confocal microscope. This microscope offers single molecule sensitivity and nanometer resolution in the X, Y, and Z planes and allowed for identification of even minor peptide localization with different intracellular compartments using various probe-labeling moieties commercially available that label different intracellular organelles. Optimized PA-SAH-FOXP3DD and PA-SAHFOXP3NFAT and their point mutant controls are structurally evaluated as previously described to determine shape, size, and helicity. The minimal concentration of PA necessary to form micelles (critical micellar concentration, CMC) is determined using standard means. Stepwise in solution, transcriptional, and in vitro determination of efficacy ensured on-target specificity and allow for biochemical tailoring of lead compounds in parallel with increasingly biologically complex analyses.

Experiments are conducted during development of embodiments herein to investigate the therapeutic efficacy of PA-SAH-FOXP3DDs and PA-SAH-FOXP3NFATs to alter FOXP3-mediated gene transcription and block T cell-mediated immune suppression. The purpose of these experiments was to evaluate the ability of lead PA-SAH-FOXP3DDs and PA-SAH-FOXP3NFATs to modulate FOXP3-mediated gene transcription and resultant Treg inhibition. Different gene-transcriptional effects occur by inhibiting FOXP3 function via disruption of FOXP3 homodimerization via its leucine zipper (SAH-FOXPDD) versus it's interaction with NFAT1. For instance, repression of Il2 and activation of Il2ra and Ctla4 transcription occurs upon cooperative binding of NFAT and FOXP3 to corresponding promoter regions. These targets are primarily affected by treatment with PA-SAH-FOXP3NFAT and not PA-SAH-FOXP3DD12. Experiments conducted during development of embodiments herein elucidated how targeting FOXP3 in two geographically distinct locations alters FOXP3 transcriptional control. It was determined whether these effects are additive, synergistic, or antagonistic.

To correlate transcriptional changes with Treg function, the ability of PA-SAH-FOXP3s to block Treg function in vitro was measured using previously detailed Treg immunosuppression assays. Increasing ratios of Tregs and conventional T cells (Tcons) isolated from the spleen of FOXP3-IRES-GFP mice or from the peripheral blood of healthy volunteers will be added in 96-well format along with a range (0.63 μM→20 μM) of PA-SAH-FOXP3s and their point mutant controls prior to stimulation with anti-CD3 and anti-CD28 coated sulfate latex beads. To ensure the purity of each T subset, intracellular staining of FOXP3 was performed on samples prior to testing. The cells will be incubated for 24, 48, and 72 hours. Tcon proliferation will be monitored at each time point using the XTT Cell Proliferation Assay Kit and cytokine expression will be evaluated with the Human or Mouse Cytokine Array Kits, Panel A (R&D Systems). Experiments were conducted during development of embodiments herein to target PA-SAH-FOXP3s to Tregs. Unlike small molecules, PAs can be targeted for specific cell delivery through the incorporation of monoclonal (mAb), Fab fragments, or single-chain antibodies via direct linkage to the peptide or DSPE-PEG2000 tail, for example mAbs specific for CD25 and the α-subunit of the IL-2 receptor, and anti-CD4 mABs. Concentrating on using anti-CD4 mAbs promoted PA-SAH-FOXP3 passage into the cell. Conventional chemical-coupling techniques were utilized to covalently attach the C-terminal carboxylic acid of the anti-CD4 mAb to the termini of the DSPE-PEG2000 polymer to make anti-CD4-PA-SAH-FOXP3DDs and anti-CD4-PASAH-FOXP3NFATs. The anti-CD4 mAb is linked to PEG2000 to conserve the overall micelle structure, enhance solubility, and allow for prolonged in vivo half-life. Multiple ratios of CD4-DSPE-PEG2000 was mixed with equal ratios of PA-SAH-FOXP3DD and PA-SAH-FOXP3NFAT to form stable PAs (e.g. 1:1:1; 0.5:1:1, 0.1:1:1, 0.05:1:1, and 0.01:1:1). Once formed, these anti-CD4-PA-SAH-FOXP3s were structurally evaluated as previously described and specificity of internalization was tested on expanded human CD4+ Tregs, conventional CD4+ and CD8+ T cells, and CD19+ B cells. Alternatively (e.g., in the event that full-length anti-CD4 mAbs prove too large (IgG: ~14.5×8.5×4 nm3; 160 kDa) or sterically hinder PA micellar formation), a recombinant single-chain anti-CD4 antibody (ScFvCD4) consisting of mAb heavy- and light-chain variable domains connected via a flexible linker was also utilized. Although representing only 20% of an intact antibody, ScFv fragments (~25-28 kDa) maintain high affinity and binding specificities.

```
Wild Type
SEQ ID NO 1:
HLLDEKGRAQCLLQREMVQSLEQQLVLEKEKLSAMQAHLAG

SAH2
SEQ ID NO 2:
HLLDEKGRAQCLxQREMVQxLEQQLVLEKEKLSAMQAHLAG

SAH3
SEQ ID NO 3:
HLLDEKGRAQCLLQREMVQSLExQLVLEKxKLSAMQAHLAG

SAH4
SEQ ID NO 4:
KGRAQCLLQREMVQSLExQLVLEKxKLSAMQAH

SAH7
SEQ ID NO 5:
FxKHCQADxLLDEKGRAQCLLQREBVQSLEQQLVLEKEKL

SAH9
SEQ ID NO 6:
LLDEKGRAQCLxQREBVQxLEQQLVLEKEK

SAH10
SEQ ID NO 7:
RAQCLLQREBVQSLExQLVLEKxKLSABQAH

Peptide B2V2
SEQ ID NO 8:
SGSKAQCLLQREMVQSLEQQLVLEKEK

Peptide B2V3
SEQ ID NO 9:
SGSGSKAQCLLQREMVQSLEQQLVLEKEK
```

TABLE 1

Unstapled FOXP3 peptides.

| SEQ ID NO | N-term | Sequence | C-term | Peptide Name | Range |
|---|---|---|---|---|---|
| 1 |  | FLKHCQADHLLDEKGRAQCLLQREMVQSLEQQLVLEKEKLSAMQAHLAG |  | hFOXP3 | hFOXP3 (214-262) |
| 2 |  | FLKHCQADHLLDEKGKAQCLLQREVVQSLEQQLELEKEKLGAMQAHLAG |  | mFOXP3 | mFOXP3 (213-261) |
| 3 |  | CLLQREVVQSLEQQLELEKEKLGAMQAH |  | mFOXP3 LZ CC | mFOXP3 (231-258) |
| 4 | Ac- | LLQREMVQSLEQQLVLEKEKLSAMQAH | -Am | hFOXP3 Short, P1 | hFOXP3 (233-259) |
| 5 | Ac- | LLDEKGRAQCLLQREMVQSLEQQLVLEKEKL | -Am | hFOXP3 Long, P2, A4 | hFOXP3 (223-253) |
| 6 |  | LLDEKGRAQCLLQREMVQSLEQQLVLEKEK | -Am | heFOXP3(30), P3 | hFOXP3 (223-252) |
| 7 |  | DEKGRAQCLLQREMVQSLEQQLVLEKEK | -Am | heFOXP3(28), P4 | hFOXP3 (225-252) |
| 8 | Ac- | LLDEKGRAQCLLQREMVQSLEQQ | -Am | P5 | hFOXP3 (223-245) |
| 9 | Ac- | QQLVLEKEKLSAMQAHLAG | -Am | P6 | hFOXP3 (244-262) |
| 10 | Ac- | RAQCLLQREMVQSLEQQLVLEKEKLSAMQAH | -Am | US10 or P7 | hFOXP3 (229-259) |
| 11 | Ac- | QCLLQREMVQSLEQQLVLE | -Am | P8 | hFOXP3 (231-249) |
| 12 | Ac- | LLDEKGRAQCLLQREMVQSLEQQLVLEKEKLSAMQ | -Am | P9 | hFOXP3 (223-257) |
| 13 | Ac- | VQSLEQQLVLEKEK | -Am | P10 | hFOXP3 (239-252) |
| 14 | Ac- | LLQREMVQSLEQQLVLEKEKL | -Am | A1 | hFOXP3 (233-253) |
| 15 | Ac- | RAQCLLQREMVQSLEQQLVLEKEKL | -Am | A2 | hFOXP3 (229-253) |
| 16 | Ac- | DEKGRAQCLLQREMVQSLEQQLVLEKEKL | -Am | A3 | hFOXP3 (225-253) |
| 17 | Ac- | LLQREMVQSLEQQLVLEKEK | -Am | B1 | hFOXP3 (233-252) |
| 18 | Ac- | RAQCLLQREMVQSLEQQLVLEKEK | -Am | B2 | hFOXP3 (229-252) |
| 19 | Ac- | DEKGRAQCLLQREMVQSLEQQLVLEKEK | -Am | B3 | hFOXP3 (225-252) |
| 20 | Ac- | LLDEKGRAQCLLQREMVQSLEQQLVLEKEK | -Am | B4 | hFOXP3 (223-252) |
| 21 | Ac- | SGSRAQCLLQREMVQSLEQQLVLEKEK | -Am | B2 V2 | SGS hFOXP3 (229-252) |
| 22 | FITC- | SGSRAQCLLQREMVQSLEQQLVLEKEK | -Am | FL-B2 V2 | SGS hFOXP3 (229-252) |
| 23 | Ac- | SGSGSRAQCLLQREMVQSLEQQLVLEKEK | -Am | B2 V3 | SGSGS hFOXP3 (229-252) |

TABLE 1-continued

Unstapled FOXP3 peptides.

| SEQ ID NO | N-term | Sequence | C-term | Peptide Name | Range |
|---|---|---|---|---|---|
| 24 | Ac- | SGSGSRAQCLLQREMVQSLEQQLVLEKEK | -FITC | B2 V3-FL | SGSGS hFOXP3 (229-252) |
| 25 | Ac- | HLLDEKGRAQCLLQREMVQSLEQQLVLEKEKLSAMQAHLAG | -Am | US2n3 | hFOXP3 (222-262) |
| 26 | FITC-Beta A | HLLDEKGRAQCLLQREMVQSLEQQLVLEKEKLSAMQAHLAG | -Am | US2n3FL | hFOXP3 (222-262) |
| 27 | Ac- | KGRAQCLLQREMVQSLEQQLVLEKEKLSAMQAH | -Am | US4 | hFOXP3 (227-259) |
| 28 | FITC-Beta A | KGRAQCLLQREMVQSLEQQLVLEKEKLSAMQAH | -Am | US4FL | hFOXP3 (227-259) |
| 29 | Ac- | FLKHCQADHLLDEKGRAQCLLQREMVQSLEQQLVLEKEKL | -Am | US7 | hFOXP3 (214-253) |
| 30 | FITC-Beta A | FLKHCQADHLLDEKGRAQCLLQREMVQSLEQQLVLEKEKL | -Am | US7FL | hFOXP3 (214-253) |
| 31 | FITC-Beta A | LLDEKGRAQCLLQREMVQSLEQQLVLEKEK | -Am | US9FL | hFOXP3 (223-252) |
| 32 | FITC-Beta A | RAQCLLQREMVQSLEQQLVLEKEKLSAMQAH | -Am | US10FL | hFOXP3 (229-259) |

TABLE 2

Stapled FOXP3 peptides.

| SEQ ID NO | N-term | Sequence | C-term | Peptide Name | Range | Staple | Mutations |
|---|---|---|---|---|---|---|---|
| 33 | Ac- | H8LDEKGKXQCLLQREVQSLEQQLELEKEKLGAMQAHLAG | -Am | mFOXP3 LZ SAH1 | mFOXP3 (221-261) | (L222, A229) | |
| 34 | Ac- | HLLDEKGKAQCL8QREVQXLEQQLELEKEKLGAMQAHLAG | -Am | mFOXP3 LZ SAH1 | mFOXP3 (221-261) | (L233, S240) | |
| 35 | Ac- | HLLDEKGKAQCLLQREVQSLE8QLELEKEKXXLGAMQAHLAG | -Am | mFOXP3 LZ SAH1 | mFOXP3 (221-261) | (Q243, E250) | |
| 36 | Ac- | H8LDEKGRXQCLLQREVQSLEQQLVLEKEKLSAMQAHLAG | -Am | hFOXP3 LZ SAH1 | hFOXP3 (222-262) | (L223, A230) | |
| 37 | Ac- | HLLDEKGRAQCL8QREMVQXLEQQLVLEKEKLSAMQAHLAG | -Am | hFOXP3 LZ SAH2 | hFOXP3 (222-262) | (L234, S241) B | |
| 38 | Ac- | HLLDEKGRAQCLLQREMVQSLE8QLVLEKXKLSAMQAHLAG | -Am | hFOXP3 LZ SAH3 | hFOXP3 (222-262) | (Q244, E251) C | |
| 39 | Ac- | KGRAQCLLQREMVQSLE8QLVLEKXKKLSAMQAH | -Am | hFOXP3 LZ SAH4 | hFOXP3 (227-259) | (Q244, E251) C | |
| 40 | Ac- | LLDEKGRAQCL8QREMVQXLEQQLVLEKEK | -Am | hFOXP3 LZ SAH5 | hFOXP3 (223-252) | (L234, S241) B | |
| 41 | Ac- | F8KHCQADXLLDEKGRAQCLLQREMVQSLEQQLVLEKEKL | -Am | hFOXP3 LZ SAH7 | hFOXP3 (214-253) | (I215, H222) Z | |
| 42 | Ac- | FLKHC8ADHLLDXKGRAQCLLQREMVQSLEQQLVLEKEKL | -Am | hFOXP3 LZ SAH8 | hFOXP3 (214-253) | (Q218, E225) | |
| 43 | Ac- | LLDEKGRAQCL8QREMVQXLEQQLVLEKEK | -Am | hFOXP3 LZ SAH9 | hFOXP3 (223-252) | (L234, S241) B | |
| 44 | Ac- | RAQCLLQREMVQSLE8QLVLEKXKKLSAMQAH | -Am | hFOXP3 LZ SAH10 | hFOXP3 (229-259) | (Q244, E251) C | |
| 45 | Ac- | H8LDEKGRXQCLLQREVQSPEQQLELEQEQLGAMQAHLAG | -Am | mFOXP3 LZ SAH1 L242P K250Q K252Q | mFOXP3 (222-262) | (L223, A230) | K250Q K252Q |
| 46 | Ac- | HLLDEKGRAQCL8QREMVQXLEQQLVLEQEQLSAMQAHLAG | -Am | hFOXP3 LZ SAH2 K250Q K252Q | hFOXP3 (222-262) | (L234, S241) B | K250Q K252Q |
| 47 | Ac- | HLLDEKGRAQCLLQREMVQSPE8QLVLEKXKLSAMQAHLAG | -Am | hFOXP3 LZ SAH3 L242P | hFOXP3 (222-262) | (Q244, E251) C | L242P |
| 48 | Ac- | KGRAQCLLQREMVQSPE8QLVLEKXKKLSAMQAH | -Am | hFOXP3 LZ SAH4 L242P | hFOXP3 (227-259) | (Q244, E251) C | L242P |
| 49 | Ac- | LLDEKGRAQCL8QREMVQXLEQQLVLEQEQ | -Am | hFOXP3 LZ SAH5 K250Q K252Q | hFOXP3 (223-252) | (L234, S241) B | K250Q K252Q |
| 50 | Ac- | RAQCLLQREMVQSPE8QLVLEKXKKLSAMQAH | -Am | hFOXP3 LZ SAH6 L242P | hFOXP3 (229-259) | (Q244, E251) C | L242P |
| 51 | FITC- | HLLDEKGRAQCL8QREBVQXLEQQLVLEKEKLSABQAHLAG | -Am | hFOXP3 LZ SAH2 | hFOXP3 (222-262) | (L234, S241) B | |
| 52 | FITC- | HLLDEKGRAQCLLQREMVQSLE8QLVLEKXKLSABQAHLAG | -Am | hFOXP3 LZ SAH3 | hFOXP3 (222-262) | (Q244, E251) C | |
| 53 | FITC- | KGRAQCLLQREBVQSLE8QLVLEKXKLSABQAH | -Am | hFOXP3 LZ SAH4 | hFOXP3 (227-259) | (Q244, E251) C | |
| 54 | FITC- | F8KHCQADXLLDEKGRAQCLLQREBVQSLEQQLVLEKEKL | -Am | hFOXP3 LZ SAH7 | hFOXP3 (214-253) | (I215, H222) Z | |

TABLE 2-continued

Stapled FOXP3 peptides.

| SEQ ID NO | N-term | Sequence | C-term | Peptide Name | Range | Staple | Mutations |
|---|---|---|---|---|---|---|---|
| 55 | FITC- | LLDEKGRAQCL8QREBVQXLEQQLVLEKEK | -Am | hFOXP3 LZ SAH9 | hFOXP3 (223-252) | (L234, S241)B | |
| 56 | FITC- | RAQCLLQREBVQSLE8QLVLEKXKLSABQAH | -Am | hFOXP3 LZ SAH10 | hFOXP3 (229-259) | (Q244, E251)C | |
| 57 | Ac | RAQCLLQREBVQSLE8QLVLEKXKLSABQAH | -Am | SAH-FOXP3DD10-C (Mutant) | hFOXP3 (229-259) | (Q244, E251)C | K252D |
| 58 | Ac | RAQCL8QREBVQXLE8QLVLEKXKLSABQAH | -Am | SAH-FOXP3DD10-BC | hFOXP3 (229-259) | (Q244, E251)C (L234, S241)B | |
| 59 | Ac | RAQC8LQREBVXSLE8QLVLEKXKLSABQAH | -Am | SAH-FOXP3DD10-AC | hFOXP3 (229-259) | (Q244, E251)C (L233, Q240)A | |
| 60 | Ac | RAQSLLQREBVQSLE8QLVLEKXKLSABQAH | -Am | SAH-FOXP3DD10 (C>S) | hFOXP3 (229-259) | (Q244, E251)C | C232S |
| 61 | FITC | RAQCLLQREBVQSLE8QLVLEKXKLSABQAH | -Am | FITC-SAH-FOXP3DD10-C (Mutant) | hFOXP3 (229-259) | (Q244, E251)C | K252D |
| 62 | FITC | RAQCL8QREBVQXLE8QLVLEKXKLSABQAH | -Am | FITC-SAH-FOXP3DD10-BC | hFOXP3 (229-259) | (Q244, E251)C (L234, S241)B | |
| 63 | FITC | RAQC8LQREBVXSLE8QLVLEKXKLSABQAH | -Am | FITC-SAH-FOXP3DD10-AC | hFOXP3 (229-259) | (Q244, E251)C (L233, Q240)A | |
| 64 | FITC | RAQSLLQREBVQSLE8QLVLEKXKLSABQAH | -Am | FITC-SAH-FOXP3DD10 (C>S) | hFOXP3 (229-259) | (Q244, E251)C | C232S |

TABLE 3

FOXP3/NFAT peptides

| SEQ ID NO | N-term | Sequence | Peptide C-term | Name | Range |
|---|---|---|---|---|---|
| 66 | β-Ala | QRTLNEIYHWFTRNFAFF | Ac | WT FoxP3 | |
| 67 | β-Ala | QRTXNEIXHWFTRNFAFF | Ac | FoxP3 sh | |
| 68 | β-Ala | QRWXWEIXHWFTRNFAFF | Ac | FoxP3 shWW | |
| 69 | β-Ala | QRTXNEIYHWXTRNFAFF | Ac | Foxp3 long | |
| 70 | β-Ala | QRWXWEIYHWXTRNFAFF | Ac | FoxP3 long WW | |

REFERENCES

The following references, some of which are cited above, are herein incorporated by reference in their entireties.

Walensky L D, Bird G H. Hydrocarbon-Stapled Peptides: Principles, Practice, and Progress. J Med Chem 2014.

LaBelle J L, Katz S G, Bird G H, et al. A stapled BIM peptide overcomes apoptotic resistance in hematologic cancers. J Clin Invest 2012; 122:2018-31.

Bird G H, Gavathiotis E, LaBelle J L, Katz S G, Walensky L D. Distinct BimBH3 (BimSAHB) stapled peptides for structural and cellular studies. ACS Chem Biol 2014; 9:831-7.

Missirlis D, Khant H, Tirrell M. Mechanisms of peptide amphiphile internalization by SJSA-1 cells in vitro. Biochemistry 2009; 48:3304-14.

Bennett C L, Christie J, Ramsdell F, et al. The immune dysregulation, polyendocrinopathy, enteropathy, X-linked syndrome (IPEX) is caused by mutations of FOXP3. Nat Genet 2001; 27:20-1.

Curiel T J, Coukos G, Zou L, et al. Specific recruitment of regulatory T cells in ovarian carcinoma fosters immune privilege and predicts reduced survival. Nature medicine 2004; 10:942-9.

Dannull J, Su Z, Rizzieri D, et al. Enhancement of vaccine-mediated antitumor immunity in cancer patients after depletion of regulatory T cells. J Clin Invest 2005; 115:3623-33.

Colombo M P, Piconese S. Regulatory-T-cell inhibition versus depletion: the right choice in cancer immunotherapy. Nature Reviews Cancer 2007; 7:880-7.

Zhang H, Chua K S, Guimond M, et al. Lymphopenia and interleukin-2 therapy alter homeostasis of CD4+CD25+ regulatory T cells. Nature medicine 2005; 11:1238-43.

Song X, Li B, Xiao Y, et al. Structural and biological features of FOXP3 dimerization relevant to regulatory T cell function. Cell Rep 2012; 1:665-75.

Wu Y, Borde M, Heissmeyer V, et al. FOXP3 controls regulatory T cell function through cooperation with NFAT. Cell 2006; 126:375-87.

Lozano T, Villanueva L, Durantez M, et al. Inhibition of FOXP3/NFAT Interaction Enhances T Cell Function after TCR Stimulation. J Immunol 2015; 195:3180-9.

Wan Y Y, Flavell R A. Regulatory T-cell functions are subverted and converted owing to attenuated Foxp3 expression. Nature 2007; 445:766-70.

Katz S G, Labelle J L, Meng H, et al. Mantle cell lymphoma in cyclin D1 transgenic mice with Bim-deficient B cells. Blood 2014; 123:884-93.

Doronina S O, Toki B E, Torgov M Y, et al. Development of potent monoclonal antibody auristatin conjugates for cancer therapy. Nature biotechnology 2003; 21:778-84.

Bird G H, Boyapalle S, Wong T, et al. Mucosal delivery of a double-stapled RSV peptide prevents nasopulmonary infection. J Clin Invest 2014; 124:2113-24.

Edwards A L, Wachter F, Lammert M, et al. Cellular Uptake and Ultrastructural Localization Underlie the Pro-apoptotic Activity of a Hydrocarbon-stapled BIM BH3 Peptide. ACS Chem Biol 2015; 10:2149-57.

Missirlis D, Teesalu T, Black M, Tirrell M. The non-peptidic part determines the internalization mechanism and intracellular trafficking of peptide amphiphiles. PloS one 2013; 8:e54611.

Zheng Y, Josefowicz S Z, Kas A, Chu T T, Gavin M A, Rudensky A Y. Genome-wide analysis of Foxp3 target genes in developing and mature regulatory T cells. Nature 2007; 445:936-40.

Fontenot, J. D., Gavin, M. A. & Rudensky, A. Y. Foxp3 programs the development and function of CD4+CD25+ regulatory T cells. Nature immunology 4, 330-336, doi:10.1038/ni904 (2003).

Bates, G. J. et al. Quantification of regulatory T cells enables the identification of high-risk breast cancer patients and those at risk of late relapse. J Clin Oncol 24, 5373-5380, doi:10.1200/JCO.2006.05.9584 (2006).

Atkins, M. B. et al. High-dose recombinant interleukin 2 therapy for patients with metastatic melanoma: analysis of 270 patients treated between 1985 and 1993. J Clin Oncol 17, 2105-2116 (1999).

Fyfe, G. et al. Results of treatment of 255 patients with metastatic renal cell carcinoma who received high-dose recombinant interleukin-2 therapy. J Clin Oncol 13, 688-696 (1995).

Koreth, J. et al. Interleukin-2 and regulatory T cells in graft-versus-host disease. The New England journal of medicine 365, 2055-2066, doi:10.1056/NEJMoa1108188 (2011).

Zhang, H. et al. Lymphopenia and interleukin-2 therapy alter homeostasis of CD4+CD25+ regulatory T cells. Nature medicine 11, 1238-1243, doi:10.1038/nm1312 (2005).

Li, B. et al. FOXP3 ensembles in T-cell regulation. Immunol Rev 212, 99-113, doi:10.1111/j.0105-2896.2006.00405.x (2006).

Song, X. et al. Structural and biological features of FOXP3 dimerization relevant to regulatory T cell function. Cell Rep 1, 665-675, doi:10.1016/j.celrep.2012.04.012 (2012).

Wu, Y. et al. FOXP3 controls regulatory T cell function through cooperation with NFAT. Cell 126, 375-387, doi:10.1016/j.cell.2006.05.042 (2006).

Lozano, T. et al. Inhibition of FOXP3/NFAT Interaction Enhances T Cell Function after TCR Stimulation. J Immunol 195, 3180-3189, doi:10.4049/jimmunol.1402997 (2015).

Balandina, A., Lecart, S., Dartevelle, P., Saoudi, A. & Berrih-Aknin, S. Functional defect of regulatory CD4(+)CD25+ T cells in the thymus of patients with autoimmune myasthenia gravis. Blood 105, 735-741, doi:10.1182/blood-2003-11-3900 (2005).

Wan, Y. Y. & Flavell, R. A. Regulatory T-cell functions are subverted and converted owing to attenuated Foxp3 expression. Nature 445, 766-770, doi:10.1038/nature05479 (2007).

Bandukwala H S, Wu Y, Feuerer M, et al. Structure of a domain-swapped FOXP3 dimer on DNA and its function in regulatory T cells. Immunity. 2011; 34(4):479-491. PMC3085397.

Schafmeister C E, Po J, Verdine G L. An All-Hydrocarbon Cross-Linking System for Enhancing the Helicity and Metabolic Stability of Peptides. J. Am. Chem. Soc. 2000; 122(24):5891-5892.

Galande A K, Bramlett K S, Trent J O, Burris T P, Wittliff JL, Spatola A F. Potent inhibitors of LXXLL-based protein-protein interactions. Chembiochem. 2005; 6(11):1991-1998.

Judice J K, Tom J Y, Huang W, et al. Inhibition of HIV type 1 infectivity by constrained alpha-helical peptides: implications for the viral fusion mechanism. Proc Natl Acad Sci USA. 1997; 94(25):13426-13430. PMC28321

Leduc A M, Trent J O, Wittliff J L, et al. Helix-stabilized cyclic peptides as selective inhibitors of steroid receptor-coactivator interactions. Proc Natl Acad Sci USA. 2003; 100(20):11273-11278. PMC208747

Sia S K, Carr P A, Cochran A G, Malashkevich V N, Kim P S. Short constrained peptides that inhibit HIV-1 entry. Proc Natl Acad Sci USA. 2002; 99(23):14664-14669. PMC137476

The invention claimed is:

1. A stapled alpha helical (SAH) peptide comprising at least 70% sequence identity to SEQ ID NO: 44 and being 31 or fewer amino acids in length, the peptide having a single hydrocarbon staple; wherein the SAH peptide is capable of inhibiting forkhead box P3 (FOX3P) oligomerization.

2. The SAH peptide of claim 1, wherein the SAH peptide comprises 100% sequence identity to SEQ ID NO: 44.

3. The SAH peptide of claim 1 comprising one or more non-natural amino acids, modified amino acids, amino acid analogs, and/or peptoid amino acids.

4. A method of inhibiting FOXP3 oligomerization and/or function comprising administering the SAH peptide of claim 1 to a cell or subject.

5. A pharmaceutical composition comprising the SAH peptide of claim 1.

6. A method of inhibiting FOXP3 oligomerization and/or function comprising administering the SAH peptide of claim 1 or PA thereof to a subject or cell.

7. The SAH peptide of claim 1, wherein the peptide has at least 90% sequence identity to SEQ ID NO: 44.

8. The SAH peptide of claim 1, wherein the SAH peptide is capable of binding to FOX3P.

9. The SAH peptide of claim 1, wherein the SAH peptide is capable of inhibiting FOX3P homodimerization.

10. The SAH peptide of claim 1, wherein the SAH peptide is capable of inhibiting FOX3P heterodimerization with nuclear factor of activated T cells (NFAT).

11. The SAH peptide of claim 1, wherein the SAH peptide is non-toxic to T cells and Tregs.

12. The SAH peptide of claim 1, wherein the SAH peptide is capable of blocking FOX3P binding to cognate DNA.

13. The SAH peptide of claim 1, wherein the SAH peptide is capable of altering expression of FOXP3 target genes.

* * * * *

SEQUENCE LISTING

```
<160> NUMBER OF SEQ ID NOS: 75

<210> SEQ ID NO 1
<211> LENGTH: 49
<212> TYPE: PRT
<213> ORGANISM: Artificial sequence
<220> FEATURE:
<223> OTHER INFORMATION: Synthetic

<400> SEQUENCE: 1

Phe Leu Lys His Cys Gln Ala Asp His Leu Leu Asp Glu Lys Gly Arg
1               5                   10                  15

Ala Gln Cys Leu Leu Gln Arg Glu Met Val Gln Ser Leu Glu Gln Gln
                20                  25                  30

Leu Val Leu Glu Lys Glu Lys Leu Ser Ala Met Gln Ala His Leu Ala
            35                  40                  45

Gly

<210> SEQ ID NO 2
<211> LENGTH: 49
<212> TYPE: PRT
<213> ORGANISM: Artificial sequence
<220> FEATURE:
<223> OTHER INFORMATION: Synthetic

<400> SEQUENCE: 2

Phe Leu Lys His Cys Gln Ala Asp His Leu Leu Asp Glu Lys Gly Lys
1               5                   10                  15

Ala Gln Cys Leu Leu Gln Arg Glu Val Val Gln Ser Leu Glu Gln Gln
                20                  25                  30

Leu Glu Leu Glu Lys Glu Lys Leu Gly Ala Met Gln Ala His Leu Ala
            35                  40                  45

Gly

<210> SEQ ID NO 3
<211> LENGTH: 28
<212> TYPE: PRT
<213> ORGANISM: Artificial sequence
<220> FEATURE:
<223> OTHER INFORMATION: Synthetic

<400> SEQUENCE: 3

Cys Leu Leu Gln Arg Glu Val Val Gln Ser Leu Glu Gln Gln Leu Glu
1               5                   10                  15

Leu Glu Lys Glu Lys Leu Gly Ala Met Gln Ala His
                20                  25

<210> SEQ ID NO 4
<211> LENGTH: 27
```

```
<212> TYPE: PRT
<213> ORGANISM: Artificial sequence
<220> FEATURE:
<223> OTHER INFORMATION: Synthetic

<400> SEQUENCE: 4

Leu Leu Gln Arg Glu Met Val Gln Ser Leu Glu Gln Gln Leu Val Leu
1               5                   10                  15

Glu Lys Glu Lys Leu Ser Ala Met Gln Ala His
            20                  25

<210> SEQ ID NO 5
<211> LENGTH: 31
<212> TYPE: PRT
<213> ORGANISM: Artificial sequence
<220> FEATURE:
<223> OTHER INFORMATION: Synthetic

<400> SEQUENCE: 5

Leu Leu Asp Glu Lys Gly Arg Ala Gln Cys Leu Leu Gln Arg Glu Met
1               5                   10                  15

Val Gln Ser Leu Glu Gln Gln Leu Val Leu Glu Lys Glu Lys Leu
            20                  25                  30

<210> SEQ ID NO 6
<211> LENGTH: 30
<212> TYPE: PRT
<213> ORGANISM: Artificial sequence
<220> FEATURE:
<223> OTHER INFORMATION: Synthetic

<400> SEQUENCE: 6

Leu Leu Asp Glu Lys Gly Arg Ala Gln Cys Leu Leu Gln Arg Glu Met
1               5                   10                  15

Val Gln Ser Leu Glu Gln Gln Leu Val Leu Glu Lys Glu Lys
            20                  25                  30

<210> SEQ ID NO 7
<211> LENGTH: 28
<212> TYPE: PRT
<213> ORGANISM: Artificial sequence
<220> FEATURE:
<223> OTHER INFORMATION: Synthetic

<400> SEQUENCE: 7

Asp Glu Lys Gly Arg Ala Gln Cys Leu Leu Gln Arg Glu Met Val Gln
1               5                   10                  15

Ser Leu Glu Gln Gln Leu Val Leu Glu Lys Glu Lys
            20                  25

<210> SEQ ID NO 8
<211> LENGTH: 23
<212> TYPE: PRT
<213> ORGANISM: Artificial sequence
<220> FEATURE:
<223> OTHER INFORMATION: Synthetic

<400> SEQUENCE: 8

Leu Leu Asp Glu Lys Gly Arg Ala Gln Cys Leu Leu Gln Arg Glu Met
1               5                   10                  15

Val Gln Ser Leu Glu Gln Gln
            20

<210> SEQ ID NO 9
```

```
<211> LENGTH: 19
<212> TYPE: PRT
<213> ORGANISM: Artificial sequence
<220> FEATURE:
<223> OTHER INFORMATION: Synthetic

<400> SEQUENCE: 9

Gln Gln Leu Val Leu Glu Lys Glu Lys Leu Ser Ala Met Gln Ala His
1               5                   10                  15

Leu Ala Gly

<210> SEQ ID NO 10
<211> LENGTH: 31
<212> TYPE: PRT
<213> ORGANISM: Artificial sequence
<220> FEATURE:
<223> OTHER INFORMATION: Synthetic

<400> SEQUENCE: 10

Arg Ala Gln Cys Leu Leu Gln Arg Glu Met Val Gln Ser Leu Glu Gln
1               5                   10                  15

Gln Leu Val Leu Glu Lys Glu Lys Leu Ser Ala Met Gln Ala His
            20                  25                  30

<210> SEQ ID NO 11
<211> LENGTH: 19
<212> TYPE: PRT
<213> ORGANISM: Artificial sequence
<220> FEATURE:
<223> OTHER INFORMATION: Synthetic

<400> SEQUENCE: 11

Gln Cys Leu Leu Gln Arg Glu Met Val Gln Ser Leu Glu Gln Gln Leu
1               5                   10                  15

Val Leu Glu

<210> SEQ ID NO 12
<211> LENGTH: 35
<212> TYPE: PRT
<213> ORGANISM: Artificial sequence
<220> FEATURE:
<223> OTHER INFORMATION: Synthetic

<400> SEQUENCE: 12

Leu Leu Asp Glu Lys Gly Arg Ala Gln Cys Leu Leu Gln Arg Glu Met
1               5                   10                  15

Val Gln Ser Leu Glu Gln Gln Leu Val Leu Glu Lys Glu Lys Leu Ser
            20                  25                  30

Ala Met Gln
        35

<210> SEQ ID NO 13
<211> LENGTH: 14
<212> TYPE: PRT
<213> ORGANISM: Artificial sequence
<220> FEATURE:
<223> OTHER INFORMATION: Synthetic

<400> SEQUENCE: 13

Val Gln Ser Leu Glu Gln Gln Leu Val Leu Glu Lys Glu Lys
1               5                   10

<210> SEQ ID NO 14
<211> LENGTH: 21
```

```
<212> TYPE: PRT
<213> ORGANISM: Artificial sequence
<220> FEATURE:
<223> OTHER INFORMATION: Synthetic

<400> SEQUENCE: 14

Leu Leu Gln Arg Glu Met Val Gln Ser Leu Glu Gln Gln Leu Val Leu
1               5                   10                  15
Glu Lys Glu Lys Leu
            20

<210> SEQ ID NO 15
<211> LENGTH: 25
<212> TYPE: PRT
<213> ORGANISM: Artificial sequence
<220> FEATURE:
<223> OTHER INFORMATION: Synthetic

<400> SEQUENCE: 15

Arg Ala Gln Cys Leu Leu Gln Arg Glu Met Val Gln Ser Leu Glu Gln
1               5                   10                  15
Gln Leu Val Leu Glu Lys Glu Lys Leu
            20                  25

<210> SEQ ID NO 16
<211> LENGTH: 29
<212> TYPE: PRT
<213> ORGANISM: Artificial sequence
<220> FEATURE:
<223> OTHER INFORMATION: Synthetic

<400> SEQUENCE: 16

Asp Glu Lys Gly Arg Ala Gln Cys Leu Leu Gln Arg Glu Met Val Gln
1               5                   10                  15
Ser Leu Glu Gln Gln Leu Val Leu Glu Lys Glu Lys Leu
            20                  25

<210> SEQ ID NO 17
<211> LENGTH: 20
<212> TYPE: PRT
<213> ORGANISM: Artificial sequence
<220> FEATURE:
<223> OTHER INFORMATION: Synthetic

<400> SEQUENCE: 17

Leu Leu Gln Arg Glu Met Val Gln Ser Leu Glu Gln Gln Leu Val Leu
1               5                   10                  15
Glu Lys Glu Lys
            20

<210> SEQ ID NO 18
<211> LENGTH: 24
<212> TYPE: PRT
<213> ORGANISM: Artificial sequence
<220> FEATURE:
<223> OTHER INFORMATION: Synthetic

<400> SEQUENCE: 18

Arg Ala Gln Cys Leu Leu Gln Arg Glu Met Val Gln Ser Leu Glu Gln
1               5                   10                  15
Gln Leu Val Leu Glu Lys Glu Lys
            20

<210> SEQ ID NO 19
```

<211> LENGTH: 28
<212> TYPE: PRT
<213> ORGANISM: Artificial sequence
<220> FEATURE:
<223> OTHER INFORMATION: Synthetic

<400> SEQUENCE: 19

Asp Glu Lys Gly Arg Ala Gln Cys Leu Leu Gln Arg Glu Met Val Gln
1               5                   10                  15
Ser Leu Glu Gln Gln Leu Val Leu Glu Lys Glu Lys
            20                  25

<210> SEQ ID NO 20
<211> LENGTH: 30
<212> TYPE: PRT
<213> ORGANISM: Artificial sequence
<220> FEATURE:
<223> OTHER INFORMATION: Synthetic

<400> SEQUENCE: 20

Leu Leu Asp Glu Lys Gly Arg Ala Gln Cys Leu Leu Gln Arg Glu Met
1               5                   10                  15
Val Gln Ser Leu Glu Gln Gln Leu Val Leu Glu Lys Glu Lys
            20                  25                  30

<210> SEQ ID NO 21
<211> LENGTH: 27
<212> TYPE: PRT
<213> ORGANISM: Artificial sequence
<220> FEATURE:
<223> OTHER INFORMATION: Synthetic

<400> SEQUENCE: 21

Ser Gly Ser Arg Ala Gln Cys Leu Leu Gln Arg Glu Met Val Gln Ser
1               5                   10                  15
Leu Glu Gln Gln Leu Val Leu Glu Lys Glu Lys
            20                  25

<210> SEQ ID NO 22
<211> LENGTH: 27
<212> TYPE: PRT
<213> ORGANISM: Artificial sequence
<220> FEATURE:
<223> OTHER INFORMATION: Synthetic

<400> SEQUENCE: 22

Ser Gly Ser Arg Ala Gln Cys Leu Leu Gln Arg Glu Met Val Gln Ser
1               5                   10                  15
Leu Glu Gln Gln Leu Val Leu Glu Lys Glu Lys
            20                  25

<210> SEQ ID NO 23
<211> LENGTH: 29
<212> TYPE: PRT
<213> ORGANISM: Artificial sequence
<220> FEATURE:
<223> OTHER INFORMATION: Synthetic

<400> SEQUENCE: 23

Ser Gly Ser Gly Ser Arg Ala Gln Cys Leu Leu Gln Arg Glu Met Val
1               5                   10                  15
Gln Ser Leu Glu Gln Gln Leu Val Leu Glu Lys Glu Lys
            20                  25

```
<210> SEQ ID NO 24
<211> LENGTH: 29
<212> TYPE: PRT
<213> ORGANISM: Artificial sequence
<220> FEATURE:
<223> OTHER INFORMATION: Synthetic

<400> SEQUENCE: 24

Ser Gly Ser Gly Ser Arg Ala Gln Cys Leu Leu Gln Arg Glu Met Val
1               5                   10                  15

Gln Ser Leu Glu Gln Gln Leu Val Leu Glu Lys Glu Lys
            20                  25

<210> SEQ ID NO 25
<211> LENGTH: 41
<212> TYPE: PRT
<213> ORGANISM: Artificial sequence
<220> FEATURE:
<223> OTHER INFORMATION: Synthetic

<400> SEQUENCE: 25

His Leu Leu Asp Glu Lys Gly Arg Ala Gln Cys Leu Leu Gln Arg Glu
1               5                   10                  15

Met Val Gln Ser Leu Glu Gln Gln Leu Val Leu Glu Lys Glu Lys Leu
            20                  25                  30

Ser Ala Met Gln Ala His Leu Ala Gly
        35                  40

<210> SEQ ID NO 26
<211> LENGTH: 41
<212> TYPE: PRT
<213> ORGANISM: Artificial sequence
<220> FEATURE:
<223> OTHER INFORMATION: Synthetic

<400> SEQUENCE: 26

His Leu Leu Asp Glu Lys Gly Arg Ala Gln Cys Leu Leu Gln Arg Glu
1               5                   10                  15

Met Val Gln Ser Leu Glu Gln Gln Leu Val Leu Glu Lys Glu Lys Leu
            20                  25                  30

Ser Ala Met Gln Ala His Leu Ala Gly
        35                  40

<210> SEQ ID NO 27
<211> LENGTH: 33
<212> TYPE: PRT
<213> ORGANISM: Artificial sequence
<220> FEATURE:
<223> OTHER INFORMATION: Synthetic

<400> SEQUENCE: 27

Lys Gly Arg Ala Gln Cys Leu Leu Gln Arg Glu Met Val Gln Ser Leu
1               5                   10                  15

Glu Gln Gln Leu Val Leu Glu Lys Glu Lys Leu Ser Ala Met Gln Ala
            20                  25                  30

His

<210> SEQ ID NO 28
<211> LENGTH: 33
<212> TYPE: PRT
<213> ORGANISM: Artificial sequence
<220> FEATURE:
<223> OTHER INFORMATION: Synthetic
```

<400> SEQUENCE: 28

Lys Gly Arg Ala Gln Cys Leu Leu Gln Arg Glu Met Val Gln Ser Leu
1               5                   10                  15

Glu Gln Gln Leu Val Leu Glu Lys Glu Lys Leu Ser Ala Met Gln Ala
            20                  25                  30

His

<210> SEQ ID NO 29
<211> LENGTH: 40
<212> TYPE: PRT
<213> ORGANISM: Artificial sequence
<220> FEATURE:
<223> OTHER INFORMATION: Synthetic

<400> SEQUENCE: 29

Phe Leu Lys His Cys Gln Ala Asp His Leu Leu Asp Glu Lys Gly Arg
1               5                   10                  15

Ala Gln Cys Leu Leu Gln Arg Glu Met Val Gln Ser Leu Glu Gln Gln
            20                  25                  30

Leu Val Leu Glu Lys Glu Lys Leu
        35                  40

<210> SEQ ID NO 30
<211> LENGTH: 40
<212> TYPE: PRT
<213> ORGANISM: Artificial sequence
<220> FEATURE:
<223> OTHER INFORMATION: Synthetic

<400> SEQUENCE: 30

Phe Leu Lys His Cys Gln Ala Asp His Leu Leu Asp Glu Lys Gly Arg
1               5                   10                  15

Ala Gln Cys Leu Leu Gln Arg Glu Met Val Gln Ser Leu Glu Gln Gln
            20                  25                  30

Leu Val Leu Glu Lys Glu Lys Leu
        35                  40

<210> SEQ ID NO 31
<211> LENGTH: 30
<212> TYPE: PRT
<213> ORGANISM: Artificial sequence
<220> FEATURE:
<223> OTHER INFORMATION: Synthetic

<400> SEQUENCE: 31

Leu Leu Asp Glu Lys Gly Arg Ala Gln Cys Leu Leu Gln Arg Glu Met
1               5                   10                  15

Val Gln Ser Leu Glu Gln Gln Leu Val Leu Glu Lys Glu Lys
            20                  25                  30

<210> SEQ ID NO 32
<211> LENGTH: 31
<212> TYPE: PRT
<213> ORGANISM: Artificial sequence
<220> FEATURE:
<223> OTHER INFORMATION: Synthetic

<400> SEQUENCE: 32

Arg Ala Gln Cys Leu Leu Gln Arg Glu Met Val Gln Ser Leu Glu Gln
1               5                   10                  15

Gln Leu Val Leu Glu Lys Glu Lys Leu Ser Ala Met Gln Ala His
            20                  25                  30

```
<210> SEQ ID NO 33
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Amino acid analog with crosslinkable
      sidechain
<220> FEATURE:
<221> NAME/KEY: MISC_FEATURE
<222> LOCATION: (9)..(9)
<223> OTHER INFORMATION: Xaa = Amino acid analog with crosslinkable
      sidechain

<400> SEQUENCE: 33

His Xaa Leu Asp Glu Lys Gly Lys Xaa Gln Cys Leu Leu Gln Arg Glu
1               5                   10                  15

Val Val Gln Ser Leu Glu Gln Gln Leu Glu Leu Glu Lys Glu Lys Leu
                20                  25                  30

Gly Ala Met Gln Ala His Leu Ala Gly
            35                  40

<210> SEQ ID NO 34
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Amino acid analog with crosslinkable
      sidechain
<220> FEATURE:
<221> NAME/KEY: MISC_FEATURE
<222> LOCATION: (20)..(20)
<223> OTHER INFORMATION: Xaa = Amino acid analog with crosslinkable
      sidechain

<400> SEQUENCE: 34

His Leu Leu Asp Glu Lys Gly Lys Ala Gln Cys Leu Xaa Gln Arg Glu
1               5                   10                  15

Val Val Gln Xaa Leu Glu Gln Gln Leu Glu Leu Glu Lys Glu Lys Leu
                20                  25                  30

Gly Ala Met Gln Ala His Leu Ala Gly
            35                  40

<210> SEQ ID NO 35
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (30)..(30)
<223> OTHER INFORMATION: Xaa = Amino acid analog with crosslinkable
      sidechain

<400> SEQUENCE: 35
```

His Leu Leu Asp Glu Lys Gly Lys Ala Gln Cys Leu Leu Gln Arg Glu
1               5                   10                  15

Val Val Gln Ser Leu Glu Xaa Gln Leu Glu Leu Glu Lys Xaa Lys Leu
                20                  25                  30

Gly Ala Met Gln Ala His Leu Ala Gly
            35                  40

<210> SEQ ID NO 36
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Amino acid analog with crosslinkable
      sidechain
<220> FEATURE:
<221> NAME/KEY: MISC_FEATURE
<222> LOCATION: (9)..(9)
<223> OTHER INFORMATION: Xaa = Amino acid analog with crosslinkable
      sidechain

<400> SEQUENCE: 36

His Xaa Leu Asp Glu Lys Gly Arg Xaa Gln Cys Leu Leu Gln Arg Glu
1               5                   10                  15

Met Val Gln Ser Leu Glu Gln Gln Leu Val Leu Glu Lys Glu Lys Leu
                20                  25                  30

Ser Ala Met Gln Ala His Leu Ala Gly
            35                  40

<210> SEQ ID NO 37
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Amino acid analog with crosslinkable
      sidechain
<220> FEATURE:
<221> NAME/KEY: MISC_FEATURE
<222> LOCATION: (20)..(20)
<223> OTHER INFORMATION: Xaa = Amino acid analog with crosslinkable
      sidechain

<400> SEQUENCE: 37

His Leu Leu Asp Glu Lys Gly Arg Ala Gln Cys Leu Xaa Gln Arg Glu
1               5                   10                  15

Met Val Gln Xaa Leu Glu Gln Gln Leu Val Leu Glu Lys Glu Lys Leu
                20                  25                  30

Ser Ala Met Gln Ala His Leu Ala Gly
            35                  40

<210> SEQ ID NO 38
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: Xaa = Amino acid analog with crosslinkable
      sidechain

```
<220> FEATURE:
<221> NAME/KEY: MISC_FEATURE
<222> LOCATION: (30)..(30)
<223> OTHER INFORMATION: Xaa = Amino acid analog with crosslinkable
      sidechain

<400> SEQUENCE: 38

His Leu Leu Asp Glu Lys Gly Arg Ala Gln Cys Leu Leu Gln Arg Glu
1               5                   10                  15

Met Val Gln Ser Leu Glu Xaa Gln Leu Val Leu Glu Lys Xaa Lys Leu
            20                  25                  30

Ser Ala Met Gln Ala His Leu Ala Gly
        35                  40

<210> SEQ ID NO 39
<211> LENGTH: 33
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: Xaa = Amino acid analog with crosslinkable
      sidechain
<220> FEATURE:
<221> NAME/KEY: MISC_FEATURE
<222> LOCATION: (25)..(25)
<223> OTHER INFORMATION: Xaa = Amino acid analog with crosslinkable
      sidechain

<400> SEQUENCE: 39

Lys Gly Arg Ala Gln Cys Leu Leu Gln Arg Glu Met Val Gln Ser Leu
1               5                   10                  15

Glu Xaa Gln Leu Val Leu Glu Lys Xaa Lys Leu Ser Ala Met Gln Ala
            20                  25                  30

His

<210> SEQ ID NO 40
<211> LENGTH: 30
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = Amino acid analog with crosslinkable
      sidechain
<220> FEATURE:
<221> NAME/KEY: MISC_FEATURE
<222> LOCATION: (19)..(19)
<223> OTHER INFORMATION: Xaa = Amino acid analog with crosslinkable
      sidechain

<400> SEQUENCE: 40

Leu Leu Asp Glu Lys Gly Arg Ala Gln Cys Leu Xaa Gln Arg Glu Met
1               5                   10                  15

Val Gln Xaa Leu Glu Gln Gln Leu Val Leu Glu Lys Glu Lys
            20                  25                  30

<210> SEQ ID NO 41
<211> LENGTH: 40
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (2)..(2)
<223> OTHER INFORMATION: Xaa = Amino acid analog with crosslinkable
      sidechain
<220> FEATURE:
<221> NAME/KEY: MISC_FEATURE
<222> LOCATION: (9)..(9)
<223> OTHER INFORMATION: Xaa = Amino acid analog with crosslinkable
      sidechain

<400> SEQUENCE: 41

Phe Xaa Lys His Cys Gln Ala Asp Xaa Leu Leu Asp Glu Lys Gly Arg
1               5                   10                  15

Ala Gln Cys Leu Leu Gln Arg Glu Met Val Gln Ser Leu Glu Gln Gln
            20                  25                  30

Leu Val Leu Glu Lys Glu Lys Leu
        35                  40

<210> SEQ ID NO 42
<211> LENGTH: 40
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa = Amino acid analog with crosslinkable
      sidechain
<220> FEATURE:
<221> NAME/KEY: MISC_FEATURE
<222> LOCATION: (13)..(13)
<223> OTHER INFORMATION: Xaa = Amino acid analog with crosslinkable
      sidechain

<400> SEQUENCE: 42

Phe Leu Lys His Cys Xaa Ala Asp His Leu Leu Asp Xaa Lys Gly Arg
1               5                   10                  15

Ala Gln Cys Leu Leu Gln Arg Glu Met Val Gln Ser Leu Glu Gln Gln
            20                  25                  30

Leu Val Leu Glu Lys Glu Lys Leu
        35                  40

<210> SEQ ID NO 43
<211> LENGTH: 30
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = Amino acid analog with crosslinkable
      sidechain
<220> FEATURE:
<221> NAME/KEY: MISC_FEATURE
<222> LOCATION: (19)..(19)
<223> OTHER INFORMATION: Xaa = Amino acid analog with crosslinkable
      sidechain

<400> SEQUENCE: 43

Leu Leu Asp Glu Lys Gly Arg Ala Gln Cys Leu Xaa Gln Arg Glu Met
1               5                   10                  15

Val Gln Xaa Leu Glu Gln Gln Leu Val Leu Glu Lys Glu Lys
            20                  25                  30

<210> SEQ ID NO 44
<211> LENGTH: 31
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain

<400> SEQUENCE: 44

Arg Ala Gln Cys Leu Leu Gln Arg Glu Met Val Gln Ser Leu Glu Xaa
1               5                   10                  15

Gln Leu Val Leu Glu Lys Xaa Lys Leu Ser Ala Met Gln Ala His
            20                  25                  30

<210> SEQ ID NO 45
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Amino acid analog with crosslinkable
      sidechain
<220> FEATURE:
<221> NAME/KEY: MISC_FEATURE
<222> LOCATION: (9)..(9)
<223> OTHER INFORMATION: Xaa = Amino acid analog with crosslinkable
      sidechain

<400> SEQUENCE: 45

His Xaa Leu Asp Glu Lys Gly Lys Xaa Gln Cys Leu Leu Gln Arg Glu
1               5                   10                  15

Val Val Gln Ser Pro Glu Gln Gln Leu Glu Leu Glu Gln Glu Gln Leu
            20                  25                  30

Gly Ala Met Gln Ala His Leu Ala Gly
        35                  40

<210> SEQ ID NO 46
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Amino acid analog with crosslinkable
      sidechain
<220> FEATURE:
<221> NAME/KEY: MISC_FEATURE
<222> LOCATION: (20)..(20)
<223> OTHER INFORMATION: Xaa = Amino acid analog with crosslinkable
      sidechain

<400> SEQUENCE: 46

His Leu Leu Asp Glu Lys Gly Arg Ala Gln Cys Leu Xaa Gln Arg Glu
1               5                   10                  15

Met Val Gln Xaa Leu Glu Gln Gln Leu Val Leu Glu Gln Glu Gln Leu
            20                  25                  30

Ser Ala Met Gln Ala His Leu Ala Gly
```

<210> SEQ ID NO 47
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (30)..(30)
<223> OTHER INFORMATION: Xaa = Amino acid analog with crosslinkable
      sidechain

<400> SEQUENCE: 47

His Leu Leu Asp Glu Lys Gly Arg Ala Gln Cys Leu Leu Gln Arg Glu
1               5                   10                  15

Met Val Gln Ser Pro Glu Xaa Gln Leu Val Leu Glu Lys Xaa Lys Leu
            20                  25                  30

Ser Ala Met Gln Ala His Leu Ala Gly
        35                  40

<210> SEQ ID NO 48
<211> LENGTH: 33
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: Xaa = Amino acid analog with crosslinkable
      sidechain
<220> FEATURE:
<221> NAME/KEY: MISC_FEATURE
<222> LOCATION: (25)..(25)
<223> OTHER INFORMATION: Xaa = Amino acid analog with crosslinkable
      sidechain

<400> SEQUENCE: 48

Lys Gly Arg Ala Gln Cys Leu Leu Gln Arg Glu Met Val Gln Ser Pro
1               5                   10                  15

Glu Xaa Gln Leu Val Leu Glu Lys Xaa Lys Leu Ser Ala Met Gln Ala
            20                  25                  30

His

<210> SEQ ID NO 49
<211> LENGTH: 30
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = Amino acid analog with crosslinkable
      sidechain
<220> FEATURE:
<221> NAME/KEY: MISC_FEATURE
<222> LOCATION: (19)..(19)
<223> OTHER INFORMATION: Xaa = Amino acid analog with crosslinkable
      sidechain

<400> SEQUENCE: 49

```
Leu Leu Asp Glu Lys Gly Arg Ala Gln Cys Leu Xaa Gln Arg Glu Met
1               5                   10                  15

Val Gln Xaa Leu Glu Gln Gln Leu Val Leu Glu Gln Glu Gln
            20                  25                  30

<210> SEQ ID NO 50
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain

<400> SEQUENCE: 50

Arg Ala Gln Cys Leu Leu Gln Arg Glu Met Val Gln Ser Pro Glu Xaa
1               5                   10                  15

Gln Leu Val Leu Glu Lys Xaa Lys Leu Ser Ala Met Gln Ala His
            20                  25                  30

<210> SEQ ID NO 51
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Amino acid analog with crosslinkable
      sidechain
<220> FEATURE:
<221> NAME/KEY: MISC_FEATURE
<222> LOCATION: (17)..(17)
<223> OTHER INFORMATION: Xaa = norleucine
<220> FEATURE:
<221> NAME/KEY: MISC_FEATURE
<222> LOCATION: (20)..(20)
<223> OTHER INFORMATION: Xaa = Amino acid analog with crosslinkable
      sidechain
<220> FEATURE:
<221> NAME/KEY: MISC_FEATURE
<222> LOCATION: (35)..(35)
<223> OTHER INFORMATION: Xaa = norleucine

<400> SEQUENCE: 51

His Leu Leu Asp Glu Lys Gly Arg Ala Gln Cys Leu Xaa Gln Arg Glu
1               5                   10                  15

Xaa Val Gln Xaa Leu Glu Gln Gln Leu Val Leu Glu Lys Glu Lys Leu
            20                  25                  30

Ser Ala Xaa Gln Ala His Leu Ala Gly
        35                  40

<210> SEQ ID NO 52
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (17)..(17)
```

```
<223> OTHER INFORMATION: Xaa = norleucine
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (30)..(30)
<223> OTHER INFORMATION: Xaa = Amino acid analog with crosslinkable
      sidechain
<220> FEATURE:
<221> NAME/KEY: MISC_FEATURE
<222> LOCATION: (35)..(35)
<223> OTHER INFORMATION: Xaa = norleucine

<400> SEQUENCE: 52

His Leu Leu Asp Glu Lys Gly Arg Ala Gln Cys Leu Leu Gln Arg Glu
1               5                   10                  15

Xaa Val Gln Ser Leu Glu Xaa Gln Leu Val Leu Glu Lys Xaa Lys Leu
            20                  25                  30

Ser Ala Xaa Gln Ala His Leu Ala Gly
            35                  40

<210> SEQ ID NO 53
<211> LENGTH: 33
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = norleucine
<220> FEATURE:
<221> NAME/KEY: MISC_FEATURE
<222> LOCATION: (18)..(18)
<223> OTHER INFORMATION: Xaa = Amino acid analog with crosslinkable
      sidechain
<220> FEATURE:
<221> NAME/KEY: MISC_FEATURE
<222> LOCATION: (25)..(25)
<223> OTHER INFORMATION: Xaa = Amino acid analog with crosslinkable
      sidechain
<220> FEATURE:
<221> NAME/KEY: MISC_FEATURE
<222> LOCATION: (30)..(30)
<223> OTHER INFORMATION: Xaa = norleucine

<400> SEQUENCE: 53

Lys Gly Arg Ala Gln Cys Leu Leu Gln Arg Glu Xaa Val Gln Ser Leu
1               5                   10                  15

Glu Xaa Gln Leu Val Leu Glu Lys Xaa Lys Leu Ser Ala Xaa Gln Ala
            20                  25                  30

His

<210> SEQ ID NO 54
<211> LENGTH: 40
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Amino acid analog with crosslinkable
      sidechain
<220> FEATURE:
<221> NAME/KEY: MISC_FEATURE
<222> LOCATION: (9)..(9)
<223> OTHER INFORMATION: Xaa = Amino acid analog with crosslinkable
```

```
                                 sidechain
<220> FEATURE:
<221> NAME/KEY: MISC_FEATURE
<222> LOCATION: (25)..(25)
<223> OTHER INFORMATION: Xaa = norleucine

<400> SEQUENCE: 54

Phe Xaa Lys His Cys Gln Ala Asp Xaa Leu Leu Asp Glu Lys Gly Arg
1               5                   10                  15

Ala Gln Cys Leu Leu Gln Arg Glu Xaa Val Gln Ser Leu Glu Gln Gln
            20                  25                  30

Leu Val Leu Glu Lys Glu Lys Leu
        35                  40

<210> SEQ ID NO 55
<211> LENGTH: 30
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = Amino acid analog with crosslinkable
      sidechain
<220> FEATURE:
<221> NAME/KEY: MISC_FEATURE
<222> LOCATION: (16)..(16)
<223> OTHER INFORMATION: Xaa = norleucine
<220> FEATURE:
<221> NAME/KEY: MISC_FEATURE
<222> LOCATION: (19)..(19)
<223> OTHER INFORMATION: Xaa = Amino acid analog with crosslinkable
      sidechain

<400> SEQUENCE: 55

Leu Leu Asp Glu Lys Gly Arg Ala Gln Cys Leu Xaa Gln Arg Glu Xaa
1               5                   10                  15

Val Gln Xaa Leu Glu Gln Gln Leu Val Leu Glu Lys Glu Lys
            20                  25                  30

<210> SEQ ID NO 56
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 56

Arg Ala Gln Cys Leu Leu Gln Arg Glu Xaa Val Gln Ser Leu Glu Xaa
1               5                   10                  15

Gln Leu Val Leu Glu Lys Xaa Lys Leu Ser Ala Xaa Gln Ala His
```

20            25            30

<210> SEQ ID NO 57
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 57

Arg Ala Gln Cys Leu Leu Gln Arg Glu Xaa Val Gln Ser Leu Glu Xaa
1               5                   10                  15
Gln Leu Val Leu Glu Lys Xaa Asp Leu Ser Ala Xaa Gln Ala His
            20                  25                  30

<210> SEQ ID NO 58
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa = Amino acid analog with crosslinkable
      sidechain
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (13)..(13)
<223> OTHER INFORMATION: Xaa = Amino acid analog with crosslinkable
      sidechain
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 58

Arg Ala Gln Cys Leu Xaa Gln Arg Glu Xaa Val Gln Xaa Leu Glu Xaa
1               5                   10                  15
Gln Leu Val Leu Glu Lys Xaa Lys Leu Ser Ala Xaa Gln Ala His
            20                  25                  30

```
<210> SEQ ID NO 59
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Amino acid analog with crosslinkable
      sidechain
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (12)..(12)
<223> OTHER INFORMATION: Xaa = Amino acid analog with crosslinkable
      sidechain
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 59

Arg Ala Gln Cys Xaa Leu Gln Arg Glu Xaa Val Xaa Ser Leu Glu Xaa
1               5                   10                  15

Gln Leu Val Leu Glu Lys Xaa Lys Leu Ser Ala Xaa Gln Ala His
            20                  25                  30

<210> SEQ ID NO 60
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa =norleucine
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa =norleucine

<400> SEQUENCE: 60

Arg Ala Gln Ser Leu Leu Gln Arg Glu Xaa Val Gln Ser Leu Glu Xaa
1               5                   10                  15

Gln Leu Val Leu Glu Lys Xaa Lys Leu Ser Ala Xaa Gln Ala His
            20                  25                  30
```

```
<210> SEQ ID NO 61
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 61

Arg Ala Gln Cys Leu Leu Gln Arg Glu Xaa Val Gln Ser Leu Glu Xaa
1               5                   10                  15

Gln Leu Val Leu Glu Lys Xaa Asp Leu Ser Ala Xaa Gln Ala His
            20                  25                  30

<210> SEQ ID NO 62
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa = Amino acid analog with crosslinkable
      sidechain
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (13)..(13)
<223> OTHER INFORMATION: Xaa = Amino acid analog with crosslinkable
      sidechain
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 62

Arg Ala Gln Cys Leu Xaa Gln Arg Glu Xaa Val Gln Xaa Leu Glu Xaa
1               5                   10                  15

Gln Leu Val Leu Glu Lys Xaa Lys Leu Ser Ala Xaa Gln Ala His
            20                  25                  30
```

```
<210> SEQ ID NO 63
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Amino acid analog with crosslinkable
      sidechain
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (12)..(12)
<223> OTHER INFORMATION: Xaa = Amino acid analog with crosslinkable
      sidechain
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 63

Arg Ala Gln Cys Xaa Leu Gln Arg Glu Xaa Val Xaa Ser Leu Glu Xaa
1               5                   10                  15

Gln Leu Val Leu Glu Lys Xaa Lys Leu Ser Ala Xaa Gln Ala His
            20                  25                  30

<210> SEQ ID NO 64
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa = norleucine
<220> FEATURE:
<221> NAME/KEY: MISC_FEATURE
<222> LOCATION: (16)..(16)
<223> OTHER INFORMATION: Xaa = Amino acid analog with crosslinkable
      sidechain
<220> FEATURE:
<221> NAME/KEY: MISC_FEATURE
<222> LOCATION: (23)..(23)
<223> OTHER INFORMATION: Xaa = Amino acid analog with crosslinkable
      sidechain
<220> FEATURE:
<221> NAME/KEY: MISC_FEATURE
<222> LOCATION: (28)..(28)
<223> OTHER INFORMATION: Xaa = norleucine

<400> SEQUENCE: 64

Arg Ala Gln Ser Leu Leu Gln Arg Glu Xaa Val Gln Ser Leu Glu Xaa
1               5                   10                  15

Gln Leu Val Leu Glu Lys Xaa Lys Leu Ser Ala Xaa Gln Ala His
            20                  25                  30

<210> SEQ ID NO 65
```

```
<211> LENGTH: 41
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = His or any amino acid
<220> FEATURE:
<221> NAME/KEY: MISC_FEATURE
<222> LOCATION: (2)..(2)
<223> OTHER INFORMATION: Xaa = Leu or Ala, or a conservative amino acid
      substitution
<220> FEATURE:
<221> NAME/KEY: MISC_FEATURE
<222> LOCATION: (3)..(3)
<223> OTHER INFORMATION: Xaa = Leu or any amino acid
<220> FEATURE:
<221> NAME/KEY: MISC_FEATURE
<222> LOCATION: (4)..(4)
<223> OTHER INFORMATION: Xaa = Asp or a conservative amino acid
      substitution
<220> FEATURE:
<221> NAME/KEY: MISC_FEATURE
<222> LOCATION: (5)..(5)
<223> OTHER INFORMATION: Xaa =Glu, or a conservative amino acid
      substitution
<220> FEATURE:
<221> NAME/KEY: MISC_FEATURE
<222> LOCATION: (6)..(6)
<223> OTHER INFORMATION: Xaa = Lys or Arg, or a conservative amino acid
      substitution
<220> FEATURE:
<221> NAME/KEY: MISC_FEATURE
<222> LOCATION: (7)..(7)
<223> OTHER INFORMATION: Xaa = Gly or Ser, or a conservative amino acid
      substitution
<220> FEATURE:
<221> NAME/KEY: MISC_FEATURE
<222> LOCATION: (8)..(8)
<223> OTHER INFORMATION: Xaa = Arg or Lys or Thr, or any amino acid
<220> FEATURE:
<221> NAME/KEY: MISC_FEATURE
<222> LOCATION: (9)..(9)
<223> OTHER INFORMATION: Xaa = Ala, or a conservative amino acid
      substitution
<220> FEATURE:
<221> NAME/KEY: MISC_FEATURE
<222> LOCATION: (10)..(10)
<223> OTHER INFORMATION: Xaa = Gln, or any amino acid
<220> FEATURE:
<221> NAME/KEY: MISC_FEATURE
<222> LOCATION: (11)..(11)
<223> OTHER INFORMATION: Xaa = Cys, or a conservative amino acid
      substitution
<220> FEATURE:
<221> NAME/KEY: MISC_FEATURE
<222> LOCATION: (12)..(12)
<223> OTHER INFORMATION: Xaa = Leu or Arg, or any amino acid
<220> FEATURE:
<221> NAME/KEY: MISC_FEATURE
<222> LOCATION: (13)..(13)
<223> OTHER INFORMATION: Xaa = Leu or Val, or a conservative amino acid
      substitution,
<220> FEATURE:
<221> NAME/KEY: MISC_FEATURE
<222> LOCATION: (14)..(14)
<223> OTHER INFORMATION: Xaa = Gln, or a conservative amino acid
      substitution
<220> FEATURE:
<221> NAME/KEY: MISC_FEATURE
<222> LOCATION: (15)..(15)
<223> OTHER INFORMATION: Xaa = Arg or Met, or any amino acid
<220> FEATURE:
<221> NAME/KEY: MISC_FEATURE
<222> LOCATION: (16)..(16)
<223> OTHER INFORMATION: Xaa = Glu or Gln, or a conservative amino acid
      substitution
```

```
<220> FEATURE:
<221> NAME/KEY: MISC_FEATURE
<222> LOCATION: (17)..(17)
<223> OTHER INFORMATION: Xaa = Met or Val, or any amino acid,
<220> FEATURE:
<221> NAME/KEY: MISC_FEATURE
<222> LOCATION: (18)..(18)
<223> OTHER INFORMATION: Xaa = Val, or a conservative amino acid
      substitution
<220> FEATURE:
<221> NAME/KEY: MISC_FEATURE
<222> LOCATION: (19)..(19)
<223> OTHER INFORMATION: Xaa = Gln, or any amino acid
<220> FEATURE:
<221> NAME/KEY: MISC_FEATURE
<222> LOCATION: (20)..(20)
<223> OTHER INFORMATION: Xaa = Ser or Gln, or a conservative amino acid
      substitution
<220> FEATURE:
<221> NAME/KEY: MISC_FEATURE
<222> LOCATION: (21)..(21)
<223> OTHER INFORMATION: Xaa = Leu, or a conservative amino acid
      substitution
<220> FEATURE:
<221> NAME/KEY: MISC_FEATURE
<222> LOCATION: (22)..(22)
<223> OTHER INFORMATION: Xaa = Glu, or a conservative amino acid
      substitution
<220> FEATURE:
<221> NAME/KEY: MISC_FEATURE
<222> LOCATION: (23)..(23)
<223> OTHER INFORMATION: Xaa = Gln or Leu, or a conservative amino acid
      substitution
<220> FEATURE:
<221> NAME/KEY: MISC_FEATURE
<222> LOCATION: (24)..(24)
<223> OTHER INFORMATION: Xaa = Gln, or a conservative amino acid
      substitution
<220> FEATURE:
<221> NAME/KEY: MISC_FEATURE
<222> LOCATION: (25)..(25)
<223> OTHER INFORMATION: Xaa = Leu, or a conservative amino acid
      substitution
<220> FEATURE:
<221> NAME/KEY: MISC_FEATURE
<222> LOCATION: (26)..(26)
<223> OTHER INFORMATION: Xaa = Val or Glu or Ala or Ser, or any amino
      acid,
<220> FEATURE:
<221> NAME/KEY: MISC_FEATURE
<222> LOCATION: (27)..(27)
<223> OTHER INFORMATION: Xaa = Leu or Lys, or a conservative amino acid
      substitution
<220> FEATURE:
<221> NAME/KEY: MISC_FEATURE
<222> LOCATION: (28)..(28)
<223> OTHER INFORMATION: Xaa = Glu or Asp, or a conservative amino acid
      substitution
<220> FEATURE:
<221> NAME/KEY: MISC_FEATURE
<222> LOCATION: (29)..(29)
<223> OTHER INFORMATION: Xaa = Lys or Arg, or a conservative amino acid
      substitution
<220> FEATURE:
<221> NAME/KEY: MISC_FEATURE
<222> LOCATION: (30)..(30)
<223> OTHER INFORMATION: Xaa = Glu, or any amino acid
<220> FEATURE:
<221> NAME/KEY: MISC_FEATURE
<222> LOCATION: (31)..(31)
<223> OTHER INFORMATION: Xaa = Lys or Arg, or a conservative amino acid
      substitution
<220> FEATURE:
<221> NAME/KEY: MISC_FEATURE
<222> LOCATION: (32)..(32)
<223> OTHER INFORMATION: Xaa = Leu, or a conservative amino acid
      substitution
<220> FEATURE:
<221> NAME/KEY: MISC_FEATURE
```

```
<222> LOCATION: (33)..(33)
<223> OTHER INFORMATION: Xaa = Ser or Gly or Gln, or any amino acid
<220> FEATURE:
<221> NAME/KEY: MISC_FEATURE
<222> LOCATION: (34)..(34)
<223> OTHER INFORMATION: Xaa = Ala, or any amino acid
<220> FEATURE:
<221> NAME/KEY: MISC_FEATURE
<222> LOCATION: (35)..(35)
<223> OTHER INFORMATION: Xaa = Met, or a conservative amino acid
      substitution,
<220> FEATURE:
<221> NAME/KEY: MISC_FEATURE
<222> LOCATION: (36)..(36)
<223> OTHER INFORMATION: Xaa = Gln or Met, or any amino acid,
<220> FEATURE:
<221> NAME/KEY: MISC_FEATURE
<222> LOCATION: (37)..(37)
<223> OTHER INFORMATION: Xaa = Ala or Thr, or any amino acid
<220> FEATURE:
<221> NAME/KEY: MISC_FEATURE
<222> LOCATION: (38)..(38)
<223> OTHER INFORMATION: Xaa = His, or any amino acid
<220> FEATURE:
<221> NAME/KEY: MISC_FEATURE
<222> LOCATION: (39)..(39)
<223> OTHER INFORMATION: Xaa = Leu, or a conservative amino acid
      substitution
<220> FEATURE:
<221> NAME/KEY: MISC_FEATURE
<222> LOCATION: (40)..(40)
<223> OTHER INFORMATION: Xaa = Ala or His, or any amino acid
<220> FEATURE:
<221> NAME/KEY: MISC_FEATURE
<222> LOCATION: (41)..(41)
<223> OTHER INFORMATION: Xaa = Gly or Val or Met, or any amino acid
<220> FEATURE:
<221> NAME/KEY: MISC_FEATURE
<222> LOCATION: (41)..(41)
<223> OTHER INFORMATION: Xaa = Gly or Val or Met, or any amino acid

<400> SEQUENCE: 65

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa
        35                  40

<210> SEQ ID NO 66
<211> LENGTH: 18
<212> TYPE: PRT
<213> ORGANISM: Artificial sequence
<220> FEATURE:
<223> OTHER INFORMATION: Synthetic

<400> SEQUENCE: 66

Gln Arg Thr Leu Asn Glu Ile Tyr His Trp Phe Thr Arg Asn Phe Ala
1               5                   10                  15

Phe Phe

<210> SEQ ID NO 67
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Amino acid analog with crosslinkable
      sidechain
```

```
<220> FEATURE:
<221> NAME/KEY: MISC_FEATURE
<222> LOCATION: (8)..(8)
<223> OTHER INFORMATION: Xaa = Amino acid analog with crosslinkable
      sidechain

<400> SEQUENCE: 67

Gln Arg Thr Xaa Asn Glu Ile Xaa His Trp Phe Thr Arg Asn Phe Ala
1               5                   10                  15

Phe Phe

<210> SEQ ID NO 68
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Amino acid analog with crosslinkable
      sidechain
<220> FEATURE:
<221> NAME/KEY: MISC_FEATURE
<222> LOCATION: (8)..(8)
<223> OTHER INFORMATION: Xaa = Amino acid analog with crosslinkable
      sidechain

<400> SEQUENCE: 68

Gln Arg Trp Xaa Trp Glu Ile Xaa His Trp Phe Thr Arg Asn Phe Ala
1               5                   10                  15

Phe Phe

<210> SEQ ID NO 69
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Amino acid analog with crosslinkable
      sidechain
<220> FEATURE:
<221> NAME/KEY: MISC_FEATURE
<222> LOCATION: (11)..(11)
<223> OTHER INFORMATION: Xaa = Amino acid analog with crosslinkable
      sidechain

<400> SEQUENCE: 69

Gln Arg Thr Xaa Asn Glu Ile Tyr His Trp Xaa Thr Arg Asn Phe Ala
1               5                   10                  15

Phe Phe

<210> SEQ ID NO 70
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Amino acid analog with crosslinkable
      sidechain
<220> FEATURE:
<221> NAME/KEY: MISC_FEATURE
<222> LOCATION: (11)..(11)
<223> OTHER INFORMATION: Xaa = Amino acid analog with crosslinkable
```

```
                       sidechain

<400> SEQUENCE: 70

Gln Arg Trp Xaa Trp Glu Ile Tyr His Trp Xaa Thr Arg Asn Phe Ala
1               5                   10                  15

Phe Phe

<210> SEQ ID NO 71
<211> LENGTH: 15
<212> TYPE: PRT
<213> ORGANISM: Artificial sequence
<220> FEATURE:
<223> OTHER INFORMATION: Synthetic

<400> SEQUENCE: 71

Arg Ala Gln Cys Leu Leu Gln Arg Glu Met Val Gln Ser Leu Glu
1               5                   10                  15

<210> SEQ ID NO 72
<211> LENGTH: 6
<212> TYPE: PRT
<213> ORGANISM: Artificial sequence
<220> FEATURE:
<223> OTHER INFORMATION: Synthetic

<400> SEQUENCE: 72

Gln Leu Val Leu Glu Lys
1               5

<210> SEQ ID NO 73
<211> LENGTH: 8
<212> TYPE: PRT
<213> ORGANISM: Artificial sequence
<220> FEATURE:
<223> OTHER INFORMATION: Synthetic

<400> SEQUENCE: 73

Lys Leu Ser Ala Met Gln Ala His
1               5

<210> SEQ ID NO 74
<211> LENGTH: 41
<212> TYPE: PRT
<213> ORGANISM: Artificial Sequence
<220> FEATURE:
<223> OTHER INFORMATION: Synthetic

<400> SEQUENCE: 74

Gly Ala Leu His Ala Gln Met Ala Gly Leu Lys Glu Lys Glu Leu Glu
1               5                   10                  15

Leu Gln Gln Glu Leu Ser Gln Val Val Glu Arg Gln Leu Leu Cys Gln
                20                  25                  30

Ala Lys Gly Lys Glu Asp Leu Leu His
            35                  40

<210> SEQ ID NO 75
<211> LENGTH: 41
<212> TYPE: PRT
<213> ORGANISM: Artificial Sequence
<220> FEATURE:
<223> OTHER INFORMATION: Synthetic

<400> SEQUENCE: 75

His Leu Leu Asp Glu Lys Gly Lys Ala Gln Cys Leu Leu Gln Arg Glu
1               5                   10                  15
```

```
Val Val Gln Ser Leu Glu Gln Gln Leu Glu Leu Glu Lys Glu Lys Leu
            20                  25                  30

Gly Ala Met Gln Ala His Leu Ala Gly
            35                  40
```